(12) United States Patent
Dang et al.

(10) Patent No.: US 7,285,543 B2
(45) Date of Patent: Oct. 23, 2007

(54) PURINE INHIBITORS OF FRUCTOSE-1,6-BISPHOSPHATASE

(75) Inventors: Qun Dang, San Diego, CA (US); Mark D. Erion, Del Mar, CA (US); M. Rami Reddy, San Diego, CA (US); Edward D. Robinson, San Diego, CA (US); Srinivas Rao Kasibhatla, San Diego, CA (US); K. Raja Reddy, San Diego, CA (US)

(73) Assignee: Metabasis Therapeutics, Inc., La Jolla, CA (US)

( * ) Notice: Subject to any disclaimer, the term of this patent is extended or adjusted under 35 U.S.C. 154(b) by 0 days.

(21) Appl. No.: 11/101,807

(22) Filed: Apr. 7, 2005

(65) Prior Publication Data

US 2005/0277619 A1    Dec. 15, 2005

Related U.S. Application Data

(60) Continuation of application No. 10/615,563, filed on Jul. 7, 2003, now Pat. No. 6,967,193, which is a continuation of application No. 09/944,096, filed on Aug. 30, 2001, now abandoned, which is a division of application No. 09/036,327, filed on Mar. 6, 1998, now Pat. No. 6,284,748.

(60) Provisional application No. 60/040,623, filed on Mar. 7, 1997.

(51) Int. Cl.
C07F 9/6561 (2006.01)
A61P 3/06 (2006.01)
A61P 3/10 (2006.01)
A61P 9/10 (2006.01)
A61K 31/675 (2006.01)

(52) U.S. Cl. .................................................. 514/81
(58) Field of Classification Search ................ 514/81
See application file for complete search history.

(56) References Cited

U.S. PATENT DOCUMENTS

| | | | |
|---|---|---|---|
| 3,931,206 A | 1/1976 | Bowler et al. | |
| 4,000,305 A | 12/1976 | Bowler et al. | |
| 4,278,791 A | 7/1981 | Botta et al. | |
| 4,939,130 A | 7/1990 | Jaeggi et al. | |
| 4,968,790 A * | 11/1990 | DeVries et al. | 514/23 |
| 5,021,443 A | 6/1991 | Bru-Magniez et al. | |
| 5,124,319 A | 6/1992 | Baudy et al. | |
| 5,294,608 A * | 3/1994 | Lang et al. | 514/108 |
| 5,376,665 A | 12/1994 | Miyata et al. | |
| 5,395,826 A | 3/1995 | Naumann et al. | |
| 5,414,088 A | 5/1995 | Von Der Saal et al. | |
| 5,480,874 A | 1/1996 | Shoji et al. | |
| 5,498,617 A | 3/1996 | Naumann et al. | |
| 5,519,138 A | 5/1996 | Ries et al. | |
| 5,658,889 A * | 8/1997 | Gruber et al. | 514/43 |
| 5,661,174 A | 8/1997 | Naumann et al. | |
| 5,728,704 A | 3/1998 | Mylari et al. | |
| 5,958,904 A | 9/1999 | Cordi et al. | |
| 5,985,856 A | 11/1999 | Stella et al. | |
| 6,054,587 A | 4/2000 | Reddy et al. | |
| 6,110,903 A | 8/2000 | Kasibhatla et al. | |
| 6,284,748 B1 | 9/2001 | Dang et al. | |
| 6,294,672 B1 | 9/2001 | Reddy et al. | |
| 6,312,662 B1 | 11/2001 | Erion et al. | |
| 6,399,782 B1 | 6/2002 | Kasibhatla et al. | |
| 6,489,476 B1 | 12/2002 | Dang et al. | |
| 6,756,360 B1 | 6/2004 | Erion et al. | |
| 6,919,322 B2 | 7/2005 | Bookser et al. | |
| 6,965,033 B2 | 11/2005 | Jiang et al. | |
| 6,967,193 B1 | 11/2005 | Dang et al. | |
| 2003/0073728 A1 | 4/2003 | van Poelje et al. | |
| 2004/0058892 A1 | 3/2004 | Dang et al. | |
| 2004/0167178 A1 | 8/2004 | Erion et al. | |

(Continued)

FOREIGN PATENT DOCUMENTS

CA    1328383    11/1993

(Continued)

OTHER PUBLICATIONS

Azen, S.P., et al., "TRIPOD (TRoglitazone In the Prevention of Diabetes): A Randomized, Placebo-Controlled Trial of Troglitazone in Women with Prior Gestational Diabetes Mellitus," *Controlled Clinical Trials*, vol. 19, Issue 2, pp. 217-231, Elsevier B.V. (Apr. 1998).

(Continued)

Primary Examiner—Mark L. Berch
(74) Attorney, Agent, or Firm—Saliwanchik, Lloyd & Saliwanchik

(57) ABSTRACT

Novel purine compounds of Formula 1, pharmaceutically acceptable prodrugs and salts thereof, and their use as fructose 1,6-bisphosphatase inhibitors

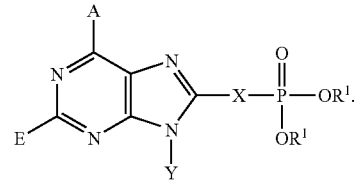

Formula 1

6 Claims, 10 Drawing Sheets

U.S. PATENT DOCUMENTS

| | | |
|---|---|---|
| 2005/0004077 A1 | 1/2005 | Jiang et al. |
| 2005/0176684 A1 | 8/2005 | Bookser et al. |

FOREIGN PATENT DOCUMENTS

| | | |
|---|---|---|
| DE | 28 55 659 | 7/1980 |
| EP | 0 012 909 | 7/1980 |
| EP | 0 73 525 | 3/1983 |
| EP | 0 117 429 | 9/1984 |
| EP | 0 354 322 | 2/1990 |
| EP | 0 354 806 | 2/1990 |
| EP | 0 427 799 | 5/1991 |
| EP | 0 449 196 | 10/1991 |
| EP | 0 604 657 | 7/1994 |
| EP | 0 620 227 | 10/1994 |
| EP | 0 632 048 | 1/1995 |
| EP | 0 753 525 | 1/1997 |
| JP | 51105093 A | 9/1976 |
| JP | 52023094 A | 2/1977 |
| JP | 53044591 A | 4/1978 |
| JP | 05-097883 | 4/1993 |
| WO | WO90/10636 | 9/1990 |
| WO | WO92/13864 | 8/1992 |
| WO | WO94/07867 | 4/1994 |
| WO | WO94/20508 | 9/1994 |
| WO | WO94/22864 | 10/1994 |
| WO | WO96/21644 | 7/1996 |
| WO | WO98/39342 | 9/1998 |
| WO | WO98/39343 | 9/1998 |
| WO | WO99/45016 | 9/1999 |
| WO | WO99/47549 | 9/1999 |
| WO | WO 00/14095 | 3/2000 |
| WO | WO 00/27401 | 5/2000 |
| WO | WO 00/38666 | 7/2000 |
| WO | WO 01/47935 | 7/2001 |
| WO | WO 01/52825 | 7/2001 |
| WO | WO 01/66553 | 9/2001 |
| WO | WO 02/03978 | 1/2002 |
| WO | WO 2006/023515 | 3/2006 |

OTHER PUBLICATIONS

Chiasson, J.-L., et al., "Acarbose for the prevention of Type 2 diabetes, hypertension and cardiovascular disease in subjects with impaired glucose tolerance: facts and interpretations concerning the critical analysis of the STOP-NIDDM Trial data," *Diabetologia*, 47: 969-975, Springer-Verlag (2004).

Delorme, S., et al., "Acarbose in the prevention of cardiovascular disease in subjects with impaired glucose tolerance and type 2 diabetes mellitus," *Current Opinion in Pharmacology*, 5:184-189, Elsevier (2005).

Dickson, J.K. et al., "Orally Active Squalene Synthase Inhibitors: Bis((acyloxy)alkly) Prodrugs of the α-Phosphonosulfonic Acid Moiety" *J. Med. Chem.* 39: 661-664 American Chemical Society (1996).

Egron, D. et al., "Synthesis and Anti-HIV Activity of Some S-Acyl-2-Thioethyl (Sate) Phosphoramidate Derivatives of 3'-Azido-2',3'Dideoxythymidine" *Nucleosides & Nucleotides* 18(4&5): 981-982 Marcel Dekker, Inc. (1999).

Erion, M.D. et al., "Computer-Assisted Scanning of Ligand Interactions: Analysis of the Fructose 1,6-Bisphosphatase-AMP Complex Using Free Energy Calculations" *J. Am. Chem. Soc.* 122: 6114-6115 American Chemical Society (2000).

Erion, M.D. and Reddy, M.R. "Ligand Interaction Scanning Using Free Energy Calculations" *Free Energy Calculations in Rational Drug Design*, Chapter 11, 225-241 Springer-Verlag (2001).

Erion, M.D. et al., "MB06322 (CS-917): A Potent and Selective Inhibitor of Fructose 1,6-Bisphosphatase for Controlling Gluconeogenesis in Type 2 Diabetes" *PNAS* 102(22): 7970-7975 (May 31, 2005).

Fisher, J.S. et al., "Glucose transport rate and glycogen synthase activity both limit skeletal muscle glycogen accumulation," *The American Journal of Physiology Endocrinol. Metab.*, vol. 282, pp. E1214-E1221 American Physiological Society (Jun. 2002).

Fujiwara, T. et al., "Suppression of Hepatic Gluconeogenesis in Long-Term Troglitazone Treated Diabetic KK and C57BL/KsJ-db/db Mice" *Metabolism* 44(4): 486-490 (Apr. 1995).

Gidh-Jain, M. et al., "The Allosteric Site of Human Liver Fructose-1,6-Bisphosphatase" *Journal of Biological Chemistry* 269(44): 27732-27738 The American Society for Biochemistry and Molecular Biology, Inc. (1994).

Holman, R.R. et al., "Assessing the potential for α-glucosidase inhibitors in prediabetic states," *Diabetes Research and Clinical Practice*, vol. 40, Supp. 1, pp. 21-25, Elsevier Ireland Ltd. (Jul. 1998).

Howard, G. et al., "Insulin Sensitivity and Atherosclerosis" *Circulation* 93(10): 1809-1817 (May 15, 1996).

Hulley, S. et al., "Randomized Trial of Estrogen Plus Progestin for Secondary Prevention of Coronary Heart Disease in Postmenopausal Women," *J. of Am. Medical Assoc.*, vol. 280, No. 7, pp. 605-613 (Aug. 19, 1998).

Inzucchi, S.E. et al., "Efficacy and Metabolic Effects of Metformin and Troglitazone in Type II Diabetes Mellitus" *N.E. Journal of Medicine* 338(13): 867-872 Massachusetts Medical Society (Mar. 26, 1998).

Link, J.T. et al., "Pharmacological regulation of hepatic glucose production," *Curr. Opin. Investig. Drugs* 4(4):421-429 (Apr. 2003).

Maggs, D.G. et al., "Metabolic Effects of Troglitazone Monotherapy in Type 2 Diabetes Mellitus" *Annals of Internal Medicine* 128(3): 176-185 American College of Physicians (Feb. 1, 1998).

Okuno, A. et al., "CS-917, a Fructose 1,6-Bisphosphatase (FBPase) Inhibitor, Suppresses Gluconeogenesis In Vitro and In Vivo by a Different Mechanism than Metformin" poster presented at The American Diabetes Association 66th Scientific Session, Washington, DC (Jun. 2006).

Pickavance, L. et al., "The Development of Overt Diabetes in Young Zucker Diabetic Fatty (ZDF) Rats and the Effects of Chronic MCC-555 Treatment" *British Journal of Pharmacology*, 125: 767-770 Stockton Press (1998).

Potter, S.C. et al., "Effect of MB06322, a Potent and Selective Inhibitor of Fructose 1,6-Bisphosphatase, on Gluconeogenesis in the ZDF Rat as Assessed by the Deuterated Water Technique" *DIAEAZ* 52(5): A364, Journal of the American Diabetes Association Abstract No. 1516-P, American Diabetes Association (Jun. 2004).

Potter, S.C., "Evidence Implicating Gluconeogenesis Inhibition as the Mechanism by Which MB06322 Lowers Blood Glucose In Vivo" *DIAEAZ* 52(2): A364, Journal of the American Diabetes Association Abstract No. 1517-P, American Diabetes Association (Jun. 2004).

Prisant, L.M., "Preventing Type II Mellitus," *J. Clin. Pharmacol.*, 44:406-413, American College of Clinical Pharmacology (2004).

Reddy, M.R. and Erion, M.D. "Computer Aided Drug Design Strategies Used in the Discovery of Fructose 1,6-Bisphosphatase Inhibitors" *Current Pharmaceutical Design* 11:283-294 Bentham Science Publishers Ltd. (2005).

Reddy, K.R. et al., "Discovery of 2-Aminopyridine Inhibitors of FBPase" abstract for the 230th National American Chemical Society (ACS) Meeting, Washington, DC, Aug./Sep. 2005, ACSMEDI Program and Abstract Book Archivese, pp. 197-198, MEDI 323, obtained from http://oasys.acs.org/acs/230nm/medi/staff/separates.cgi Aug. 8, 2005.

Reddy, M.R. and Erion, M.D. "Fructose 1,6-Bisphosphatase: Use of Free Energy Calculations in the Design and Optimization of AMP Mimetics" *Free Energy Calculations in Rational Drug Design*, Chapter 14, 285-297 Springer-Verlag (2001).

Riddle, M.C. "New Tactics for Type 2 Diabetes: Regimens Based on Intermediate-Acting Insulin Taken at Bedtime" *The Lancet* 192-195 (Jan. 26, 1985).

Sathyaprakash, R. et al., "Preventing Diabetes by Treating Aspects of the Metabolic Syndrome," *Current Diabetes Reports*, 2:416-422, Current Science, Inc. (2002).

Scheen, A.J. and Lefebvre, P.J. "Oral Antidiabetic Agents A Guide to Selection" *Drugs* 55(2): 225-236 Adis International Limited (Feb. 1998).

Sreenan, S. et al., "Prevention of Hyperglycemia in the Zucker Diabetic Fatty Rat by Treatment with Metformin or Troglitazone" *Am. J. Physiol.* 271 (*Endorcinol. Metab.* 34): E742-E747 American Physiological Society (1996).

Srivastva, D.N. and Farquhar, D. "Bioreversible Phosphate Protective Groups: Synthesis and Stability of Model Acyloxymethyl Phosphates" *Bioorganic Chemistry* 12: 118-129 Academic Press, Inc. (1984).

Torlone, E. et al., "Improved Insulin Action and Glycemic Control After Long-Term Angiotensin-Converting Enzyme Inhibition in Subjects with Arterial Hypertension and Type II Diabetes" *Diabetes Care* 16(10): 1347-1355 (Oct. 1993).

Torres, T., et al., "Inhibition of glycogen phosphorylase suppresses basal and glucagon-induced glucose production and increases glucose uptake in the liver of conscious dogs" (Integrated Physiology—Liver 1484-P), *Diabetes*, vol. 52 i6, p. A343, American Diabetes Association (Jun. 2003).

Triscari, J. et al., "Multiple Ascending Doses of CS-917, a Novel Fructose 1,6-Bisphosphatase (FBPase) Inhibitor, in Subjects with Type 2 Diabetes Treated for 14 Days" poster presented at The American Diabetes Association 66th Scientific Session, Washington, DC (Jun. 2006).

Turnbull, A. et al., "Pharmacological inhibition of glycogen phosphorylase (GP) lowers plasma glucose in rat models of type 2 diabetes. (Integrated Physiology—Liver 1485-P)," *Diabetes*, vol. 52 i6, p. A343, American Diabetes Association (Jun. 2003).

Van Poelje, P.D. et al., "Characterization of the Mechanism of Action and Antidiabetic Activity of MB06322, a Potent and Selective Inhibitor of Fructose 1,6-Bisphophatase" *DIAEAZ* 52(2): A368, Journal of the American Diabetes Association Abstract No. 1523-P, American Diabetes Association (Jun. 2004).

Van Poelje, P.D. et al., "Comparative Metabolic Effects of a Novel Fructose 1,6-Bisphosphatase Inhibitor and Metformin in the Female ZDF Rat", Abstracts of the 41st Annual Meeting of The European Association for the Study of Diabetes, Athens, Greece *Diabetologia* 48(1): A278 Abstract No. 765 Springer-Verlag (Aug. 2005).

Van Poelje, P.D. et al., "Inhibition of Fructose 1,6-Bisphosphatase Reduces Excessive Endogenous Glucose Production and Attenuates Hyperglycemia in Zucker Diabetic Fatty Rats" *Diabetes* 55: 1747-1754, American Diabetes Association (Jun. 2006).

Van Poelje, P.D. et al., "MB06322 (CS-917) Lowers Blood Glucose in Rodents by Inhibiting Both Hepatic and Renal Gluconeogenesis" *DIAEAZ* 55(1): A137, Journal of the American Diabetes Association Abstract No. 575-P, American Diabetes Association (Jun. 2006).

Van Poelje, P.D. et al., "Fructose 1,6-Bisphosphatase Inhibition Enhances the Antidiabetic Activity of Insulin Sensitizers in the ZDF Rat" *DIAEAZ* 52(2): A 366, Journal of the American Diabetes Association Abstract No. 1524-P, American Diabetes Association (Jun. 2004).

Van Poelje, P.D. "MB06322, a Potent Inhibitor of Gluconeogenesis, Attenuates Hyperglycemia without Causing Weight Gain or Hypoglycemia in Female Zucker Diabetic Fatty Rats" *DIAEAZ* 54(1): A124, Journal of the American Diabetes Assocation Abstract No. 503-P, American Diabetes Association (Jun. 2005).

Walker, J. et al., "Safety and Tolerability of Single Doses of CS-917, A Novel Gluconeogenesis Inhibitor, in Normal Male Volunteers" *DIAEAZ* 55(1): A463, Journal of the American Diabetes Association Abstract No. 2002-PO, American Diabetes Association (Jun. 2006).

Walker, J. et al., "Safety, Tolerability and Pharmacodynamics of Multiple Doses of CS-917 in Normal Volunteers" *DIAEAZ* 55(1): A464, Journal of the American Diabetes Association Abstract No. 2003-PO, American Diabetes Association (Jun. 2006).

Yoshida, T. et al., "Comparison of Acute and Chronic Glucose-Lowering Effect of CS-917, a Fructose 1,6-Bisphosphatase (FBPase) Inhibitor, and Metformin in Rat Models of Type 2 Diabetes" poster presented at The American Diabetes Association 66th Scientific Session, Washington, DC (Jun. 2006).

Yoshida, T. et al., "CS-917, a Fructose 1,6-Bisphosphatase Inhibitor, Has Glucose-Lowering Effects in Cynomolgus Monkeys and Improves Postprandial Hyperglycemia in Goto-Kakizaki (GK) Rats" *DIAEAZ* 54(1): A116-A117, Journal of the American Diabetes Association Abstract No. 472-P, American Diabetes Association (Jun. 2005).

Curran, et al. "Thermolysis of Bis[2-[(trimethylsilyl)oxy] prop-2-yl]furoxan 9TOP-furoxan). The First Practical Method for Intermolecular Cylcoaddition of an in Situ Generated Nitrile Oxide with 1,2-Di-and Trisubstituted Olefins", *J. Am. Chem. Soc.*, 1985, pp. 6023-6028, vol. 107.

Maryanoff, et al. "Steroselective Synthesis and Biological Activity of β-and α-D-Arabinose 1,5-Diphosphate: Analogues of a Potent Metabolic Regulator", *J. Am. Chem. Soc.*, 1984, pp. 7851-7853, vol. 106.

Fresenius, "Organic Chemical Nomenclature" (E. Horwood, Ltd. Chichester) p. 29 & 1st index page, 1989.

Hawley, "Condensed Chemical Dictionary", 9th Ed. (Van Norstrand Reinhold Co. NY) p. 25, 1977.

Grant, "Grant and Hack's Chemical Dictionary" (McGraw Hill, NY) p. 22, 1987.

Garuti et al. "Synthesis and Biological Evaluation of Some New Phosphates", *Pharmazie*, 1992, pp. 295-297, vol. 47.

Yoshino et al. "Organic Phosphorus Compounds. 2. Synthesis and Coronary Vasodilator Activity of (Benzothiazolylbenzy) Phosphonate Derivatives", *J. Med. Chem.*, 1989, pp. 1528-1532, vol. 32.

Turner, R.C. et al. "U.K. Prospective Diabetes Study 16: Overview of 6 Years' Therapy of Type II Diabetes, a Progressive Disease. (U.K. Prospective Diabetes Study Group)" *Diabetes*, Nov. 1995, pp. 1-11, vol. 44, No. 11 p. 1249(10), American Diabetes Association. Unverified English-language translation of Japanese Patent Publication No. 05-097883 (17 pages).

* cited by examiner

Effect of Compound 2.7 on Gluconeogenesis from Dihydroxyacetone in Rat Hepatocytes Time, minutes

24h fasted ZDF Rats + COMPOUND 2.7

PURINE INHIBITORS OF FRUCTOSE-1,6-BISPHOSPHATASE

RELATED APPLICATIONS

This application is a continuation of U.S. application Ser. No. 10/615,563, filed Jul. 7, 2003, which was a continuation of U.S. application Ser. No. 09/944,096, filed Aug. 30, 2001, now abandoned which was a divisional application of U.S. application Ser. No. 09/036,327, filed Mar. 6, 1998, now U.S. Pat. No. 6,284,748, issued Sep. 4, 2001, which claims the benefit of U.S. Provisional Application No. 60/040,623 filed Mar. 7, 1997.

FIELD OF THE INVENTION

This invention relates to novel purine compounds that are inhibitors of Fructose-1,6-bisphosphatase at the AMP site. The invention also relates to the preparation and use of these purine analogs in the treatment of diabetes, and other diseases where the inhibition of gluconeogenesis, control of blood glucose levels, reduction in glycogen stores, or reduction in insulin levels is beneficial.

BACKGROUND AND INTRODUCTION TO THE INVENTION

Diabetes mellitus (or diabetes) is one of the most prevalent diseases in the world today. Diabetes patients have been divided into two classes, namely type I or insulin-dependent diabetes mellitus and type II or non-insulin dependent diabetes mellitus (NIDDM). Non-insulin-dependent diabetes mellitus (NIDDM) accounts for approximately 90% of all diabetics and is estimated to affect 12-14 million adults in the U.S. alone (6.6% of the population). NIDDM is characterized by both fasting hyperglycemia and exaggerated postprandial increases in plasma glucose levels. NIDDM is associated with a variety of long-term complications, including microvascular diseases such as retinopathy, nephropathy and neuropathy, and macrovascular diseases such as coronary heart disease. Numerous studies in animal models demonstrate a causal relationship between long term complications and hyperglycemia. Recent results from the Diabetes Control and Complications Trial (DCCT) and the Stockholm Prospective Study demonstrate this relationship for the first time in man by showing that insulin-dependent diabetics with tighter glycemic control are at substantially lower risk for development and progression of these complications. Tighter control is also expected to benefit NIDDM patients.

Current therapies used to treat NIDDM patients entail both controlling lifestyle risk factors and pharmaceutical intervention. First-line therapy for NIDDM is typically a tightly-controlled regimen of diet and exercise since an overwhelming number of NIDDM patients are overweight or obese (~67%) and since weight loss can improve insulin secretion, insulin sensitivity and lead to normoglycemia. Normalization of blood glucose occurs in less than 30% of these patients due to poor compliance and poor response. Patients with hyperglycemia not controlled by diet alone are subsequently treated with oral hypoglycemics or insulin. Until recently, the sulfonylureas were the only class of oral hypoglycemic agents available for NIDDM. Treatment with sulfonylureas leads to effective blood glucose lowering in only 70% of patients and only 40% after 10 years of therapy. Patients that fail to respond to diet and sulfonylureas are subsequently treated with daily insulin injections to gain adequate glycemic control.

Although the sulfonylureas represent a major therapy for NIDDM patients, four factors limit their overall success. First, as mentioned above, a large segment of the NIDDM population do not respond adequately to sulfonylurea therapy (i.e. primary failures) or become resistant (i.e. secondary failures). This is particularly true in NIDDM patients with advanced NIDDM since these patients have severely impaired insulin secretion. Second, sulfonylurea therapy is associated with an increased risk of severe hypoglycemic episodes. Third, chronic hyperinsulinemia has been associated with increased cardiovascular disease although this relationship is considered controversial and unproven. Last, sulfonylureas are associated with weight gain, which leads to worsening of peripheral insulin sensitivity and thereby can accelerate the progression of the disease.

Recent results from the U.K. Diabetes prospective study also showed that patients undergoing maximal therapy of a sulfonylurea, metformin, or a combination of the two, were unable to maintain normal fasting glycemia over the six year period of the study. U.K. Prospective Diabetes Study 16. *Diabetes*, 44:1249-158 (1995). These results further illustrate the great need for alternative therapies. Three therapeutic strategies that could provide additional health benefits to NIDDM patients beyond the currently available therapies, include drugs that would: (i)prevent the onset of NIDDM; (ii) prevent diabetic complications by blocking detrimental events precipitated by chronic hyperglycemia; or (iii) normalize glucose levels or at least decrease glucose levels below the threshold reported for microvascular and macrovascular diseases.

Hyperglycemia in NIDDM is associated with two biochemical abnormalities, namely insulin resistance and impaired insulin secretion. The relative roles of these metabolic abnormalities in the pathogenesis of NIDDM has been the subject of numerous studies over the past several decades. Studies of offspring and siblings of NIDDM patients, mono- and dizygotic twins, and ethnic populations with high incidence of NIDDM (e.g. Pima Indians) strongly support the inheritable nature of the disease.

Despite the presence of insulin resistance and impaired insulin secretion, fasting blood glucose (FBG) levels remain normal in pre-diabetic patients due to a state of compensatory hyperinsulinemia. Eventually, however, insulin secretion is inadequate and fasting hyperglycemia ensues. With time insulin levels decline. Progression of the disease is characterized by increasing FBG levels and declining insulin levels.

Numerous clinical studies have attempted to define the primary defect that accounts for the progressive increase in FBG. Results from these studies indicate that excessive hepatic glucose output (HGO) is the primary reason for the elevation in FBG with a significant correlation found for HGO and FBG once FBG exceeds 140 mg/dL. Kolterman, et al., *J. Clin. Invest.* 68:957, (1981); DeFronzo *Diabetes* 37:667 (1988).

HGO comprises glucose derived from breakdown of hepatic glycogen (glycogenolysis) and glucose synthesized from 3-carbon precursors (gluconeogenesis). A number of radioisotope studies and several studies using $^{13}$C-NMR spectroscopy have shown that gluconeogenesis contributes between 50-100% of the glucose produced by the liver in the postabsorptive state and that gluconeogenesis flux is excessive (2- to 3-fold) in NIDDM patients. Magnusson, et al. *J. Clin. Invest.* 90:1323-1327 (1992); Rothman, et al., *Science* 254: 573-76 (1991); Consoli, et a 1. *Diabetes* 38:550-557 (1989).

Gluconeogenesis from pyruvate is a highly regulated biosynthetic pathway requiring eleven enzymes (FIG. 1). Seven enzymes catalyze reversible reactions and are common to both gluconeogenesis and glycolysis. Four enzymes catalyze reactions unique to gluconeogenesis, namely pyruvate carboxylase, phosphoenolpyruvate carboxykinase, fructose-1,6-bisphosphatase and glucose-6-phosphatase. Overall flux through the pathway is controlled by the specific activities of these enzymes, the enzymes that catalyzed the corresponding steps in the glycolytic direction, and by substrate availability. Dietary factors (glucose, fat) and hormones (insulin, glucagon, glucocorticoids, epinephrine) coordinatively regulate enzyme activities in the gluconeogenesis and glycolysis pathways through gene expression and post-translational mechanisms.

Of the four enzymes specific to gluconeogenesis, fructose-1,6-bisphosphatase (hereinafter "FBPase") is the most suitable target for a gluconeogenesis inhibitor based on efficacy and safety considerations. Studies indicate that nature uses the FBPase/PFK cycle as a major control point (metabolic switch) responsible for determining whether metabolic flux proceeds in the direction of glycolysis or gluconeogenesis. Claus, et al., *Mechanisms of Insulin Action*, Belfrage, P. editor, pp. 305-321, Elsevier Science 1992; Regen, et al. *J. Theor. Biol.*, 111:635-658 (1984); Pilkis, et al. *Annu. Rev. Biochem*, 57:755-783 (1988). FBPase is inhibited by fructose-2,6-bisphosphate in the cell. Fructose-2,6-bisphosphate binds to the substrate site of the enzyme. AMP binds to an allosteric site on the enzyme.

Synthetic inhibitors of FBPase have also been reported. McNiel reported that fructose-2,6-bisphosphate analogs inhibit FBPase by binding to the substrate site. *J. Med. Chem.*, 106:7851 (1984); U.S. Pat. No. 4,968,790 (1984). These compounds, however, were relatively weak and did not inhibit glucose production in hepatocytes presumably due to poor cell penetration.

Gruber reported that some nucleosides can lower blood glucose in the whole animal through inhibition of FBPase. These compounds exert their activity by first undergoing phosphorylation to the corresponding monophosphate. EP 0 427 799 B 1.

Gruber et al. U.S. Pat. No. 5,658,889 described the use of inhibitors of the AMP site of FBPase to treat diabetes.

European patent application EP 0 632 048 A1 discloses certain ethyl phosphonates of purine derivatives for use as antiviral and antineoplastic agents. These structures differ from the claimed compounds because they have no substitution on the C-8 of the purine. There is no suggestion that these compounds are inhibitors of FBPase.

SUMMARY OF THE INVENTION

Figure 1:
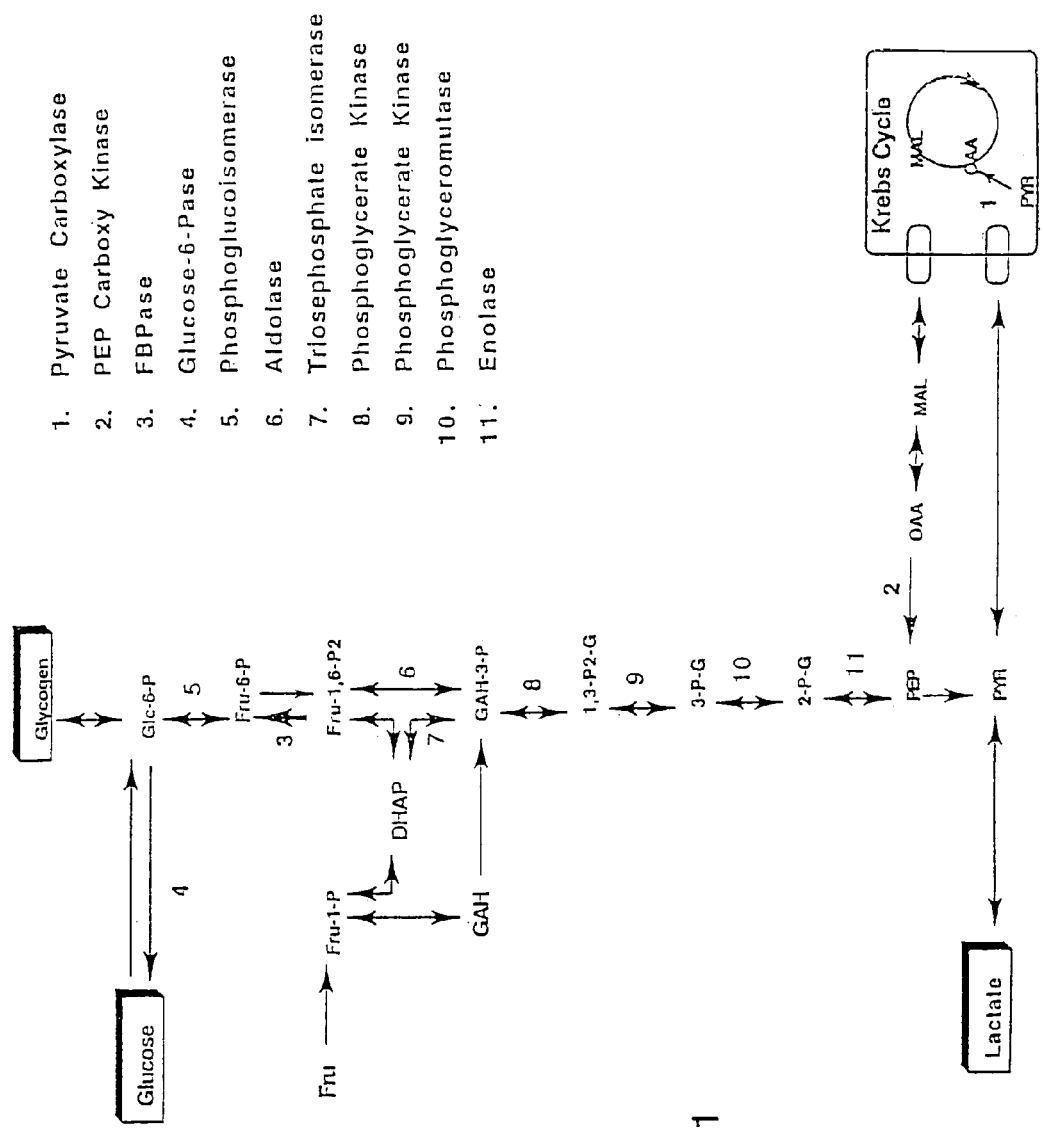
FIG. 1 is a scheme depicting the eleven enzymes of the gluconeogenesis pathway.

The present invention is directed towards novel purine compounds which bind the AMP site and are potent FBPase inhibitors. In another aspect, the present invention is directed to the preparation of these novel purine compounds and to the in vitro and in vivo FBPase inhibitory activity of these compounds. Another aspect of the present invention is directed to the clinical use of the novel FBPase inhibitors as a method of treatment or prevention of diseases responsive to inhibition of gluconeogenesis and in diseases responsive to lowered blood glucose levels.

Gruber et al. U.S. patent application Ser. No. 08/355,836 (allowed) described the use of inhibitors of the AMP site of FBPase to treat diabetes.

The compounds are also useful in treating or preventing excess glycogen storage diseases and insulin dependent diseases such as cardiovascular diseases including atherosclerosis.

The invention comprises the novel purine analogs as specified below in formula 1. Also included in the scope of the present invention are prodrugs of the compounds of formula 1.

Formula 1

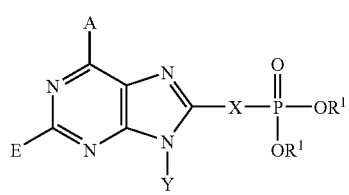

Since these compounds may have asymmetric centers, the present invention is directed not only to racemic mixtures of these compounds, but also to individual stereoisomers. The present invention also includes pharmaceutically acceptable and/or useful salts of the compounds of formula 1, including acid addition salts and basic salts. The present inventions also encompass prodrugs of compounds of formula 1.

Definitions

In accordance with the present invention and as used herein, the following terms are defined with the following meanings, unless explicitly stated otherwise.

The term "aryl" refers to aromatic groups which have at least one ring having a conjugated pi electron system and includes carbocyclic aryl, heterocyclic aryl and biaryl groups, all of which may be optionally substituted.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl groups are groups having from 1 to 4 heteroatoms as ring atoms in the aromatic ring and the remainder of the ring atoms being carbon atoms. Suitable heteroatoms include oxygen, sulfur, and nitrogen. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups containing more than one aromatic ring including both fused ring systems and aryl groups substituted with other aryl groups.

The term "alicyclic" means compounds which combine the properties of aliphatic and cyclic compounds and include but are not limited to aromatic, cycloalkyl and bridged cycloalkyl compounds. The cyclic compound includes heterocycles. Cyclohexenylethyl, cyclohexanylethyl, and norbornyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, halogen, lower alkylthio, oxa, ketone, carboxy esters, carboxyl, carboxamido, nitro, acyloxy, alkylamino, aminoalkyl, alkylaminoaryl, alkylaryl, alkylaminoalkyl, alkoxyaryl, arylamino, aralkylamino, phosphonate, sulfonate, carboxamidoalkylaryl, carboxamidoaryl, hydroxyalkyl, haloalkyl, alkylaminoalkylcarboxy, aminocarboxamidoalkyl, cyano, lower alkoxyalkyl, and lower perhaloalkyl.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl and aryl.

The term "carboxy esters" refers to —C(O)OR where R is alkyl, aryl, aralkyl, and alicyclic, all optionally substituted.

The term "oxa" refers to =O in an alkyl group.

The term "alkylamino" refers to —NRR' where R and R' are independently selected from hydrogen or alkyl.

The term "carbonylamine" or "carbonylamino" refers to —CONR$_2$ where each R is independently hydrogen or alkyl.

The term "halogen" or "halo" refers to —F, —Cl, —Br and —I.

The term "oxyalkylamino" refers to —O-alk-NR—, where "alk" is an alkylene group and R is H or alkyl.

The term "alkylsulfonate" refers to the group -alk-S(O)$_2$—O— where "alk" is an alkylene group.

The term "alkylaminoalkylcarboxy" refers to the group -alk-NR-alk-C(O)—O— where "alk" is an alkylene group, and R is a H or lower alkyl.

The term "alkylaminocarbonyl" refers to the group -alk-NR—C(O)— where "alk" is an alkylene group, and R is a H or lower alkyl.

The term "oxyalkyl" refers to the group —O-alk- where "alk" is an alkylene group.

The term "alkylcarboxyalkyl" refers to the group -alk-C(O)—O-alkyl where each alk is independently an alkylene group.

The term "alkyl" refers to saturated aliphatic groups including straight-chain, branched chain and cyclic groups. Alkyl groups may be optionally substituted.

The term "bidentate" refers to an alkyl group that is attached by its terminal ends to the same atom to form a cyclic group. For example, propylene imine contains a bidentate propylene group.

The term "cyclic alkyl" refers to alkyl groups that are cyclic.

The term "heterocyclic" and "heterocyclic alkyl" refer to cyclic alkyl groups containing at least one heteroatom. Suitable heteroatoms include oxygen, sulfur, and nitrogen. Heterocyclic groups may be attached through a heteroatom or through a carbon atom in the ring.

The term "alkenyl" refers to unsaturated groups which contain at least one carbon-carbon double bond and includes straight-chain, branched-chain and cyclic groups. Alkene groups may be optionally substituted.

The term "alkynyl" refers to unsaturated groups which contain at least one carbon-carbon triple bond and includes straight-chain, branched-chain and cyclic groups. Alkyne groups may be optionally substituted.

The term "alkylene" refers to a divalent straight chain, branched chain or cyclic saturated aliphatic radical.

The term "acyloxy" refers to the ester group —O—C(O) R, where R is H, alkyl, alkenyl, alkynyl, aryl, aralkyl, or alicyclic.

The term "alkylaryl" refers to the group -alk-aryl- where "alk" is an alkylene group. "Lower alkylaryl" refers to such groups where alkylene is lower alkyl.

The term "alkylamino" refers to the group -alk-NR- wherein "alk" is an alkylene group.

The term "alkyl(carboxyl)" refers to carboxyl substituted off the alkyl chain. Similarly, "alkyl(hydroxy)", "alkyl(phosphonate)", and "alkyl(sulfonate)" refers to substituents off the alkyl chain.

The term "alkylaminoalkyl" refers to the group -alk-NR-alk- wherein each "alk" is an independently selected alkylene, and R is H or lower alkyl. "Lower alkylaminoalkyl" refers to groups where each alkylene group is lower alkyl.

The term "alkylaminoaryl" refers to the group -alk-NR-aryl- wherein "alk" is an alkylene group. In "lower alkylaminoaryl", the alkylene group is lower alkyl.

The term "alkyloxyaryl" refers to an alkylene group substituted with an aryloxy group. In "lower alkyloxyaryl", the alkylene group is lower alkyl.

The term "alkylacylamino" refers to the group -alk-N—(COR)— wherein alk is alkylene and R is lower alkyl. In "lower alkylacylamino", the alkylene group is lower alkyl.

The term "alkoxyalkylaryl" refers to the group -alk-O-alk-aryl- wherein each "alk" is independently an alkylene group. "Lower alkoxyalkylaryl" refers to such groups where the alkylene group is lower alkyl.

The term "alkylacylaminoalkyl refers to the group -alk-N—(COR)-alk- where each alk is an independently selected alkylene group. In "lower alkylacylaminoalkyl" the alkylene groups are lower alkyl.

The term "alkoxy" refers to the group -alk-O— wherein alk is an alkylene group.

The term "alkoxyalkyl" refers to the group -alk-O-alk- wherein each alk is an independently selected alkylene group. In "lower alkoxyalkyl", each alkylene is lower alkyl.

The term "alkylthio" refers to the group -alk-S— wherein alk is alkylene group.

The term "alkylthioalkyl" refers to the group -alk-S-alk- wherein each alk is an independently selected alkylene group. In "lower alkylthioalkyl" each alkylene is lower alkylene.

The term "aralkylamino" refers to an amine substituted with an aralkyl group.

The term "alkylcarboxamido" refers to the group -alk-C(O)N(R)— wherein alk is an alkylene group and R is H or lower alkyl.

The term "alkylcarboxamidoalkyl" refers to the group -alk-C(O)N(R)-alk- wherein each alk is an independently selected alkylene group and R is lower alkyl. In "lower alkylcarboxamidoalkyl" each alkylene is lower alkyl.

The term "alkylcarboxamidoalkylaryl" refers to the group -alk$_1$-C(O)—NH-alk$_2$Ar— wherein alk$_1$ and alk$_2$ are independently selected alkylene groups and alk$_2$ is substituted with an aryl group, Ar. In "lower alkylcarboxamidoalkylaryl", each alkylene is lower alkyl.

The term "heteroalicyclic" refers to an alicyclic group having 1 to 4 heteroatoms selected from nitrogen, sulfur, phosphorus and oxygen.

The term "aminocarboxamidoalkyl" refers to the group —NH—C(O)—N(R)—R wherein each R is an independently selected alkyl group. "Lower aminocarboxamidoalkyl" refers to such groups wherein each R is lower alkyl.

The term "heteroarylalkyl" refers to an alkyl group substituted with a heteroaryl group.

The term "perhalo" refers to groups wherein every C—H bond has been replaced with a C-halo bond on an aliphatic or aryl group. Suitable perhaloalkyl groups include —CF$_3$ and —CFCl$_2$.

The term "guanidine" refers to both —NR—C(NR)—NR$_2$ as well as —N=C(NR$_2$)$_2$ where each R group is independently selected from the group of —H, alkyl, alkenyl, alkynyl, aryl, and alicyclic, all optionally substituted.

The term "amidine" refers to —C(NR)—NR$_2$ where each R group is independently selected from the group of —H, alkyl, alkenyl, alkynyl, aryl, and alicyclic, all optionally substituted.

The term "pharmaceutically acceptable salt" includes salts of compounds of formula 1 and its prodrugs derived from the combination of a compound of this invention and an organic or inorganic acid or base.

The term "prodrug" as used herein refers to any compound that when administered to a biological system generates the "drug" substance either as a result of spontaneous chemical reaction(s) or by enzyme catalyzed or metabolic reaction(s). Reference is made to various prodrugs such as acyl esters, carbonates, and carbamates, included herein. The groups illustrated are exemplary, not exhaustive, and one skilled in the art could prepare other known varieties of prodrugs. Such prodrugs of the compounds of formula 1, fall within the scope of the present invention.

The term "prodrug ester" as employed herein includes, but is not limited to, the following groups and combinations of these groups:

[1] Acyloxyalkyl esters which are well described in the literature (Farquhar et al., *J. Pharm. Sci.* 72, 324-325 (1983)) and are represented by formula A

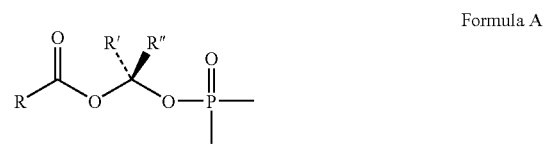

Formula A wherein R, R', and R" are independently H, alkyl, aryl, alkylaryl, and alicyclic; (see WO 90/08155; WO 90/10636).

[2] Other acyloxyalkyl esters are possible in which an alicyclic ring is formed such as shown in formula B. These esters have been shown to generate phosphorus-containing nucleotides inside cells through a postulated sequence of reactions beginning with deesterification and followed by a series of elimination reactions (e.g. Freed et al., *Biochem. Pharm.* 38: 3193-3198 (1989)).

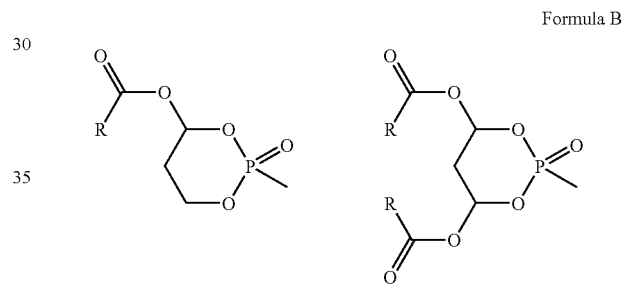

Formula B wherein R is —H, alkyl, aryl, alkylaryl, alkoxy, aryloxy, alkylthio, arylthio, alkylamino, arylamino, cycloalkyl, or alicyclic.

[3] Another class of these double esters known as alkyloxycarbonyloxymethyl esters, as shown in formula A, where R is alkoxy, aryloxy, alkylthio, arylthio, alkylamino, and arylamino; R', and R" are independently H, alkyl, aryl, alkylaryl, and alicyclic, have been studied in the area of β-lactam antibiotics (Tatsuo Nishimura et al. *J. Antibiotics,* 1987, 40(1), 81-90; for a review see Ferres, H., *Drugs of Today,* 1983,19, 499.). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

[4] Aryl esters have also been used as phosphonate prodrugs (e.g. Erion, DeLambert et al., *J. Med. Chem.* 37: 498, 1994; Serafinowska et al., *J. Med. Chem.* 38: 1372, 1995). Phenyl as well as mono and poly-substituted phenyl phosphonate ester prodrugs have generated the parent phosphonic acid in studies conducted in animals and in man (Formula C). Another approach has been described where Y is a carboxylic ester ortho to the phosphate. Khamnei and Torrence, *J. Med. Chem.;* 39:4109-4115 (1996).

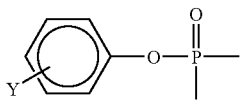

Formula C wherein Y is H, alkyl, aryl, alkylaryl, alkoxy, acetoxy, halogen, amino, alkoxycarbonyl, hydroxy, cyano, alkylamino, and alicyclic.

[5] Benzyl esters have also been reported to generate the parent phosphonic acid. In some cases, using substituents at the para-position can accelerate the hydrolysis. Benzyl analogs with 4-acyloxy or 4-alkyloxy group [Formula D, X=H, OR or O(CO)R or O(CO)OR] can generate the 4-hydroxy compound more readily through the action of enzymes, e.g. oxidases, esterases, etc. Examples of this class of prodrugs are described by Mitchell et al., *J. Chem. Soc. Perkin Trans. I* 2345 (1992); Brook, et al. WO 91/19721.

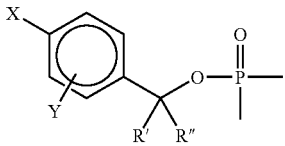

Formula D wherein X and Y are independently H, alkyl, aryl, alkylaryl, alkoxy, acetoxy, hydroxy, cyano, nitro, perhaloalkyl, halo, or alkyloxycarbonyl; and
R' and R" are independently H, alkyl, aryl, alkylaryl, halogen, and alicyclic.

[6] Thio-containing phosphonate phosphonate ester prodrugs have been described that are useful in the delivery of FBPase inhibitors to hepatocytes. These phosphonate ester prodrugs contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., *Antiviral Res.,* 22: 155-174 (1993)). Thioesters will also generate free thiolates after esterase-mediated hydrolysis. Benzaria, et al., *J. Med. Chem.,* 39:4958 (1996). Cyclic analogs are also possible and were shown to liberate phosphonate in isolated rat hepatocytes. The cyclic disulfide shown below has not been previously described and is novel.

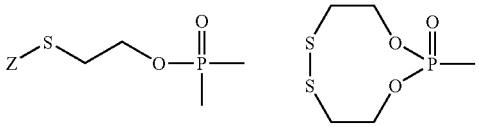

Formula E wherein Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al. (*J. Med. Chem.* 38, 1372 (1995)); Starrett et al. (*J. Med. Chem.* 37, 1857 (1994)); Martin et al. *J. Pharm. Sci.* 76, 180 (1987); Alexander et al., *Collect. Czech. Chem. Commun,* 59, 1853 (1994)); and EPO patent application 0 632 048 A1. Some of the structural classes described are optionally substituted, including fused lactones attached at the omega position and optionally substituted 2-oxo-1,3-dioxolenes attached through a methylene to the phosphorus oxygen such as:

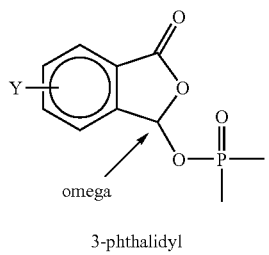 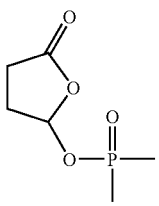

omega 3-phthalidyl      2-oxotetrahydrofuran-5-yl

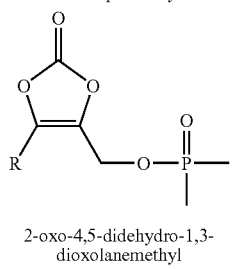

2-oxo-4,5-didehydro-1,3-dioxolanemethyl wherein R is —H, alkyl, cycloalkyl, or alicyclic; and
wherein Y is —H, alkyl, aryl, alkylaryl, cyano, alkoxy, acetoxy, halogen, amino, alkylamino, alicyclic, and alkoxycarbonyl.

[7] Propyl phosphonate ester prodrugs can also be used to deliver FBPase inhibitors into hepatocytes. These phosphonate ester prodrugs may contain a hydroxyl and hydroxyl group derivatives at the 3-position of the propyl group as shown in formula F. The R and X groups can form a cyclic ring system as shown in formula F. One or more of the oxygens of the phosphonate can be esterified.

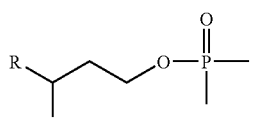

Formula F

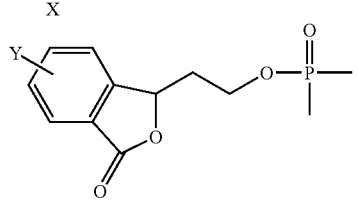

wherein R is alkyl, aryl; heteroaryl;
X is hydrogen, alkylcarbonyloxy, alkyloxycarbonyloxy; and
Y is alkyl, aryl, heteroaryl, alkoxy, alkylamino, alkylthio, halogen, hydrogen, hydroxy, acetoxy, amino.

[8] The cyclic propyl phosphonate esters as in Formula G are shown to activate to phosphonic acids. The activation of prodrug can be mechanistically explained by in vivo oxidation and elimination steps. These prodrugs inhibit glucose production in isolated rat hepatocytes and are also shown to deliver FBPase inhibitors to the liver following oral administration.

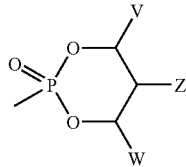

Formula G wherein

V and W are independently selected from the group consisting of hydrogen, aryl, substituted aryl, heteroaryl, substituted heteroaryl, 1-alkenyl, 1-alkynyl, and —$R^9$; or together V and Z are connected to form a cyclic group containing 3-5 atoms, optionally 1 heteroatom, substituted with hydroxy, acyloxy, alkoxycarboxy, or aryloxycarboxy attached to a carbon atom that, is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —$CH_2OH$, —$CH_2OCOR^3$, —$CH_2OC(O)SR^3$, —$CH_2OCO_2R^3$, —$SR^3$, —$S(O)R^3$, —$CH_2N_3$, —$CH_2NR^2{}_2$, —$CH_2Ar$, —$CH(Ar)OH$, —$CH(CH=CR^2R^2)OH$, —$CH(C=CR^2)OH$, and —$R^2$;

with the provisos that:
a) V, Z, W are not all —H; and
b) when Z is —$R^2$, then at least one of V and W is not —H or —$R^9$;

$R^2$ is selected from the group consisting of $R^3$ and —H;

$R^3$ is selected from the group consisting of alkyl, aryl, alicyclic, and aralkyl; and $R^9$ is selected from the group consisting of alkyl, aralkyl, and alicyclic.

[9] Phosphoramidate derivatives have been explored as potential phosphonate prodrugs (e.g. McGuigan et al., *Antiviral Res.* 1990, 14: 345; 1991, 15: 255. Serafinowska et al., *J. Med. Chem.*, 1995, 38, 1372). Most phosphoramidates are unstable under aqueous acidic conditions and are hydrolyzed to the corresponding phosphonic acids. Cyclic phosphoramidates have also been studied as phosphonate prodrugs because of their potential for greater stability compared to non cyclic phosphoramidates (e.g. Starrett et al., *J. Med. Chem.*, 1994, 37: 1857).

Other prodrugs are possible based on literature reports such as substituted ethyls for example, bis(trichloroethyl) esters as disclosed by McGuigan, et al. *Bioorg Med. Chem. Lett.*, 3:1207-1210 (1993), and the phenyl and benzyl combined nucleotide esters reported by Meier, C. et al. *Bioorg. Med. Chem. Lett.*, 7:99-104 (1997).

X group nomenclature as used herein in formula 1 describes the group attached to the phosphonate and ends with the group attached to the 2-position of the benzimidazole ring. For example, when X is alkylamino, the following structure is intended:

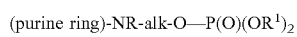

(purine ring)-NR-alk-O—P(O)(OR$^1$)$_2$

Y group nomenclature likewise ends with the group attached to the ring.

DETAILED DESCRIPTION OF THE INVENTION

Novel Purine Compounds

Preferred compounds of the present invention are inhibitors of the AMP site of FBPase of the following formula (1):

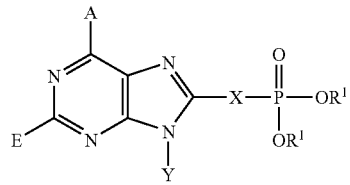

wherein

A is selected from the group consisting of —$NR^8{}_2$, $NHSO_2R^3$, —$OR^5$, —$SR^5$, halogen, lower alkyl, —$CON(R^4)_2$, guanidine, amidine, —H, and perhaloalkyl;

E is selected from the group consisting of —H, halogen, lower alkylthio, lower perhaloalkyl, lower alkyl, lower alkenyl, lower alkynyl, lower alkoxy, —CN, and —$NR^7{}_2$;

X is selected from the group consisting of alkylamino, alkyl, alkenyl, alkynyl, alkyl(carboxyl), alkyl(hydroxy), alkyl(phosphonate), alkyl(sulfonate), aryl, alkylaminoalkyl, alkoxyalkyl, alkylthioalkyl, alkylthio, alicyclic, 1,1-dihaloalkyl, carbonylalkyl, aminocarbonylamino, alkylaminocarbonyl, alkylcarbonylamino, aralkyl, and alkylaryl, all optionally substituted; or together with Y forms a cyclic group including cyclic alkyl, heterocyclic, and aryl;

Y is selected from the group consisting of —H, alkyl, alkenyl, alkynyl, aryl, alicyclic, aralkyl, aryloxyalkyl, alkoxyalkyl, —$C(O)R^3$, —$S(O)_2R^3$, —$C(O)$—$OR^3$, —$CONHR^3$, —$NR^2{}_2$, and —$OR^3$, all except H are optionally substituted; or together with X forms a cyclic group including aryl, cyclic alkyl, and heterocyclic;

$R^1$ is independently selected from the group consisting of —H, alkyl, aryl, alicyclic where the cyclic moiety contains a carbonate or thiocarbonate, —$C(R^2)_2$-aryl, alkylaryl, —$C(R^2)_2OC(O)NR^2{}_2$, —$NR^2$—$C(O)$—$R^3$, —$C(R^2)_2$—OC(O)$R^3$, $C(R^2)_2$—O—$C(O)OR^3$, —$C(R^2)_2OC(O)SR^3$, alkyl-S—$C(O)R^3$, alkyl-S—S-alkylhydroxy, and alkyl-S—S-alkylhydroxy, or together $R^1$ and $R^1$ are -alkyl-S—S-alkyl to form a cyclic group, or together $R^1$ and $R^1$ are

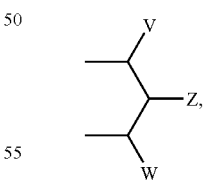

wherein

V and W are independently selected from the group consisting of hydrogen, aryl, substituted aryl, heteroaryl, substituted heteroaryl, 1-alkenyl, 1-alkynyl, and —$R^9$; or together V and Z are connected to form a cyclic group containing 3-5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from, an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2$$_2$, —CH$_2$Ar, —CH(Ar)OH, —CH(CH═CR$^2$R$^2$)OH, —CH(C≡CR$^2$)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;
R$^3$ is selected from the group consisting of alkyl, aryl, alicyclic, and aralkyl;
R$^4$ is independently selected from the group consisting of —H, lower alkyl, lower alicyclic, lower aralkyl, and lower aryl;
R$^5$ is selected from the group consisting of lower alkyl, lower aryl, lower aralkyl, and lower alicyclic;
R$^6$ is independently selected from the group consisting of —H, and lower alkyl
R$^7$ is independently selected from the group consisting of —H, lower alkyl lower alicyclic, lower aralkyl, lower aryl, and —C(O)R$^{10}$;
R$^8$ is independently selected from the group consisting of —H, lower alkyl, lower aralkyl, lower aryl, lower alicyclic, —C(O)R$^{10}$, or together they form a bidendate alkyl;
R$^9$ is selected from the group consisting of alkyl, aralkyl, and alicyclic;
R$^{10}$ is selected from the group consisting of —H, lower alkyl, —NH$_2$, lower aryl, and lower perhaloalkyl;
R$^{11}$ is selected from the group consisting of alkyl, aryl, —OH, —NH$_2$ and —OR$^3$; and pharmaceutically acceptable prodrugs and salts thereof.

Preferred Compounds of Formula 1

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 5 heteroatoms, preferably independently selected from nitrogen, oxygen, phosphorous, and sulfur. Suitable heteroalicyclic groups include groups having from 2 to about twenty carbon atoms and from 1 to 5 heteroatoms, preferably independently selected from nitrogen, oxygen, phosphorous, and sulfur.

Preferred A groups include —NR$^8$$_2$, lower alkyl, lower perhaloalkyl, lower alkoxy, and halogen. Particularly preferred are —NR$^8$$_2$, and halogen. Especially preferred is —NR$^8$$_2$. Most preferred is —NH$_2$.

Preferred E groups include —H, halogen, lower perhaloalkyl, —CN, lower alkyl, lower alkoxy, and lower alkylthio. Particularly preferred E groups include —H, —SMe, —Et, and —Cl. Especially preferred is —H and —SCH$_3$.

Preferred X groups include alkylamino, alkyl, alkynyl, alkoxyalkyl, alkylthio, aryl, 1,1-dihaloalkyl, carbonylalkyl, heteroaryl, alkylcarbonylamino, and alkylaminocarbonyl. Particularly preferred is alkyl substituted with 1 to 3 substituents selected from halogen, phosphonate, —CO$_2$H, —SO$_3$H, and —OH. Particularly preferred are alkylaminocarbonyl, alkoxyalkyl, and heteroaryl. Preferred alkoxyalkyl groups include methoxymethyl. Preferred heteroaryl groups include furanyl, optionally substituted.

Preferred Y groups include aralkyl, alicyclic, alkyl, and aryl, all optionally substituted. Particularly preferred is lower alkyl. Particularly preferred Y groups include (2-naphthyl)methyl, cyclohexylethyl, phenylethyl, nonyl, cyclohexylpropyl, ethyl, cyclopropylmethyl, cyclobutylmethylphenyl, (2-methyl)propyl, neopentyl, cyclopropyl, cyclopentyl, (1-imidozolyl)propyl, 2-ethoxybenzyl, 1-hydroxy-2,2-dimethylpropyl, 1-chloro-2,2-dimethylpropyl, 2,2-dimethylbutyl, 2-(spiro-3',3'-dimethylcyclohex-4-enyl)propyl, and 1-methylneopentyl. Especially preferred is neopentyl and isobutyl.

Preferred R$^4$ and R$^7$ groups are —H, and lower alkyl. Particularly preferred are —H, and methyl.

Preferred R$^1$ groups include —H, alkyl, aryl, alicyclic where the cyclic moiety contains a carbonate or thiocarbonate, —C(R$^2$)$_2$-aryl, alkylaryl, —C(R$^2$)$_2$OC(O)NR$^2$$_2$, —NR$^2$—C(O)—R$^3$, —C(R$^2$)$_2$—OC(O)R$^3$, C(R$^2$)$_2$—O—C(O)OR$^3$, —C(R$^2$)$_2$OC(O)SR$^3$, alkyl-S—C(O)R$^3$, alkyl-S—S-alkylhydroxy, and alkyl-S—S—S-alkylhydroxy, or together R$^1$ and R$^1$ are -alkyl-S—S-alkyl to form a cyclic group, or together R$^1$ and R$^1$ are

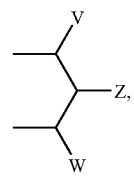

wherein

V and W are independently selected from the group consisting of hydrogen, aryl, substituted aryl, heteroaryl, substituted heteroaryl, 1-alkenyl, 1-alkynyl, and —R$^9$; or together V and Z are connected to form a cyclic group containing 3-5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2$$_2$, —CH$_2$Ar, —CH(Ar)OH, —CH(CH═CR$^2$R$^2$)OH, —CH(C≡CR$^2$)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;
R$^3$ is selected from the group consisting of alkyl, aryl, alicyclic, and aralkyl; and R$^9$ is selected from the group consisting of alkyl, aralkyl, and alicyclic.

Preferred R¹ groups include —H, alkylaryl, aryl, —C(R²)₂-aryl, and —C(R²)₂—OC(O)R³. Preferred such R¹ groups include optionally substituted phenyl, optionally substituted benzyl, —H, —C(R²)₂OC(O)OR³, and —C(R²)₂OC(O)R³. Preferably, said alkyl groups are greater than 4 carbon atoms. Another preferred aspect is Where at least one R¹ is aryl or —C(R²)₂-aryl. Also particularly preferred are compounds where R¹ is alicyclic where the cyclic moiety contains carbonate or thiocarbonate. Another preferred aspect is when at least one R¹ is —C(R²)₂—OC(O)R³, —C(R²)₂—OC(O)OR³ or —C(R²)₂—OC(O)SR³. Also particularly preferred is when R¹ and R¹ together are optionally substituted, including fused, lactone attached at the omega position or are optionally substituted 2-oxo-1,3-dioxolenes attached through a methylene to the phosphorus oxygen. Also preferred is when at least one R¹ is -alkyl-S—S-alkylhydroxyl, -alkyl-S—C(O)R³, and -alkyl-S—S—S-alkylhydroxy, or together R¹ and R¹ are -alkyl-S—S-alkyl- to form a cyclic group. Also preferred is where R¹ and R¹ together are

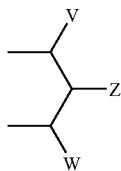

to form a cyclic group, wherein

V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3-5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH=CR²R²)OH, —CH(C≡CR²)OH, and —R²;

with the provisos that:
a) V, Z, W are not all —H; and
b) when Z is —R², then at least one of V and W is not —H or —R⁹;

R² is selected from the group consisting of R³ and —H;
R³ is selected from the group consisting of alkyl, aryl, alicyclic, and aralkyl; and
R⁹ is selected from the group consisting of alkyl, aralkyl, and alicyclic.

Particularly preferred are such groups wherein V and W both form a 6-membered carbocyclic ring substituted with 0-4 groups, selected from the group consisting of hydroxy, acyloxy, alkoxycarbonyl, and alkoxy; and Z is R². Also particularly preferred are such groups wherein V and W are hydrogen; and Z is selected from the group consisting of hydroxyalkyl, acyloxyalkyl, alkyloxyalkyl, and alkoxycarboxyalkyl. Also particularly preferred are such groups wherein V and W are independently selected from the group consisting of hydrogen, optionally substituted aryl, and optionally substituted heteroaryl, with the proviso that at least one of V and W is optionally substituted aryl or optionally substituted heteroaryl.

In one preferred aspect, R¹ is not lower alkyl of 1-4 carbon atoms.

In another preferred aspect, A is —NR⁸₂ or halogen, E is —H, halogen, —CN, lower alkyl, lower perhaloalkyl, lower alkoxy, or lower alkylthio, X is alkylamino, alkyl, alkoxyalkyl, alkynyl, 1,1-dihaloalkyl, carbonylalkyl, alkyl(OH), alkyl(sulfonate), alkylcarbonylamino, alkylaminocarbonyl, alkylthio, aryl, or heteroaryl, and R⁴ and R⁷ is —H or lower alkyl. Particularly preferred are such compounds where. Y is aralkyl, aryl, alicyclic, or alkyl. Especially preferred are such compounds where R¹ and R¹ together are

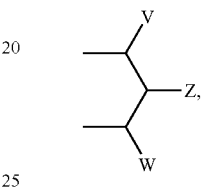

wherein

V and W are independently selected from the group consisting of hydrogen, aryl, substituted aryl, heteroaryl, substituted heteroaryl, 1-alkenyl, 1-alkynyl, and —R⁹; or together V and Z are connected to form a cyclic group containing 3-5 atoms, optionally 1 heteroatom, substituted with hydroxy, acyloxy, alkoxycarboxy, or aryloxycarboxy attached to a carbon atom that is three atoms from an oxygen attached to the phosphorus; or together V and W are connected to form a cyclic group containing 3 carbon atoms substituted with hydroxy, acyloxy, alkoxycarboxy, alkylthiocarboxy, hydroxymethyl, and aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH=CR²R²)OH, —CH(C≡CR²)OH, and —R²;

with the provisos that:
a) V, Z, W are not all —H; and
b) when Z is —R², then at least one of V and W is not —H or —R⁹;

R² is selected from the group consisting of R³ and —H;
R³ is selected from the group consisting of alkyl, aryl, alicyclic, and aralkyl; and
R⁹ is selected from the group consisting of alkyl, aralkyl, and alicyclic.

In another preferred aspect, A is —NR⁸₂, E is —H, Cl—, or methylthio, and X is optionally substituted furanyl, or alkoxyalkyl. Particularly preferred are such compounds where A is —NH₂, X is 2,5-furanyl, or methoxymethyl, and Y is lower alkyl. Most preferred are such compounds where E is H, X is 2,5-furanyl, and Y is neopentyl; those where E is —SCH₃, X is 2,5-furanyl, and Y is isobutyl; and those where E is —H, X is 2,5-furanyl, and Y is 1-(3-chloro-2,2-dimethyl)-propyl. Especially preferred are such compounds where R¹ is —CH₂O—C(O)—C(CH₃)₃.

In the following examples of preferred compounds, the following prodrugs are preferred:

Acyloxyalkyl esters;
Alkoxycarbonyloxyalkyl esters;
Aryl esters;
Benzyl and substituted benzyl esters;
Disulfide containing esters;
Substituted (1,3-dioxolen-2-one)methyl esters;
Substituted 3-phthalidyl esters;
Cyclic-[2'-hydroxymethyl]-1,3-propanyl diesters and hydroxy protected forms;
Lactone type esters; and all mixed esters resulted from possible combinations of above esters.
Bis-pivaloyloxymethyl esters;
Bis-isobutyryloxymethyl esters;
Cyclic-[2'-hydroxymethyl]-1,3-propanyl diester;
Cyclic-[2'-acetoxymethyl]-1,3-propanyl diester;
Cyclic-[2'-methyloxycarbonyloxymethyl]-1,3-propanyl diester;
Bis-benzoylthiomethyl esters;
Bis-benzoylthioethyl esters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(4-methoxyphenyl) esters;
Bis-(2-methoxyphenyl) esters;
Bis-(2-ethoxyphenyl) esters;
Mono-(2-ethoxyphenyl) esters;
Bis-(4-acetamidophenyl) esters;
Bis-(4-aceyloxyphenyl) esters;
Bis-(4-hydroxyphenyl) esters;
Bis-(2-acetoxyphenyl) esters;
Bis-(3-acetoxyphenyl) esters;
Bis-(4-morpholinophenyl) esters;
Bis-[4-(1-triazolophenyl) esters;
Bis-(3-N,N-dimethylaminophenyl) esters;
Bis-(2-tetrahydronapthyl) esters;
Bis-(3-chloro-4-methoxy)benzyl esters;
Bis-(3-bromo-4-methoxy)benzyl esters;
Bis-(3-cyano-4-methoxy)benzyl esters
Bis-(3-chloro-4-acetoxy)benzyl esters;
Bis-(3-bromo-4-acetoxy)benzyl esters;
Bis-(3-cyano-4-acetoxy)benzyl esters;
Bis-(4-chloro)benzyl esters;
Bis-(4-acetoxy)benzyl esters;
Bis-(3,5-dimethoxy-4-acetoxy)benzyl esters;
Bis-(3-methyl-4-acetoxy)benzyl esters;
Bis-(benzyl)esters;
Bis-(3-methoxy-4-acetoxy)benzyl esters;
Bis-(3-chloro-4-acetoxy)benzyl esters;
cyclic-(2,2-dimethylpropyl)phosphonoamidate;
cyclic-(2-hydroxymethylpropyl) ester;
Bis-(6'-hydroxy-3',4'-disulfide)hexyl esters;
Bis-(6'-acetoxy-3',4'-disulfide)hexyl esters;
(3',4'-Dithia)cyclononane esters;
Bis-(5-methyl-1,3-dioxolen-2-one-4-yl)methyl esters;
Bis-(5-ethyl-1,3-dioxolen-2-one-4-yl)methyl esters;
Bis-(5-tert-butyl-1,3-dioxolen-2-one-4-yl)methyl esters;
Bis-3-(5,6,7-trimethoxy)phthalidyl esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenyloxycarbonyloxymethyl) esters;
Bis-(m-methoxyphenyloxycarbonyloxymethyl) esters;
Bis-(o-methoxyphenyloxycarbonyloxymethyl) esters;
Bis-(o-methylphenyloxycarbonyloxymethyl) esters;
Bis-(p-chlorophenyloxycarbonyloxymethyl) esters;
Bis-(1,4-biphenyloxycarbonyloxymethyl) esters;
Bis-[(2-phthalimidoethyl)oxycarbonyloxymethyl]esters;
Bis-(N-Phenyl, N-methylcarbamoyloxymethyl) esters;
Bis-(2-trichloroethyl) esters;
Bis-(2-bromoethyl) esters;
Bis-(2-iodoethyl) esters;
Bis-(2-azidoethyl) esters;
Bis-(2-acetoxyethyl) esters;
Bis-(2-aminoethyl) esters;
Bis-(2-N,N-diaminoethyl) esters;
Bis-(2-aminoethyl) esters;
Bis-(methoxycarbonylmethyl) esters;
Bis-(2-aminoethyl) esters;
Bis-[N,N-di(2-hydroxyethyl)]amidomethylesters;
Bis-(2-aminoethyl) esters;
Bis-(2-methyl-5-thiozolomethyl) esters;
Bis-(bis-2-hydroxyethylamidomethyl) esters.
Most preferred are the following:
Bis-pivaloyloxymethyl esters;
Bis-isobutyryloxymethyl esters;
cyclic-(2-hydroxymethylpropyl) ester;
cyclic-(2-acetoxymethylpropyl) ester;
cyclic-(2-methyloxycarbonyloxymethylpropyl) ester;
cyclic-(2-cyclohexylcarbonyloxymethylpropyl)ester;
cyclic-(2-aminomethylpropyl)ester;
cyclic-(2-azidomethylpropyl)ester;
Bis-benzoylthiomethyl esters;
Bis-benzoylthioethylesters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(2-methyl)phenyl esters;
Bis-(2-methoxy)phenyl esters;
Bis-(2-ethoxy)phenyl esters;
Bis-(4-methoxy)phenyl esters;
Bis-(3-bromo-4-methoxy)benzyl esters;
Bis-(4-acetoxy)benzyl esters;
Bis-(3,5-dimethoxy-4-acetoxy)benzyl esters;
Bis-(3-methyl-4-acetoxy)benzyl esters;
Bis-(3-methoxy-4-acetoxy)benzyl esters;
Bis-(3-chloro-4-acetoxy)benzyl esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenyloxycarbonyloxymethyl) esters;
Bis-(m-methoxyphenyloxycarbonyloxymethyl) esters;
Bis-(o-methoxyphenyloxycarbonyloxymethyl) esters;
Bis-(o-methylphenyloxycarbonyloxymethyl) esters;
Bis-(p-chlorophenyloxycarbonyloxymethyl) esters;

Bis-(1,4-biphenyloxycarbonyloxymethyl) esters;
Bis-[(2-phthalimidoethyl)oxycarbonyloxymethyl]esters;
Bis-(6'-hydroxy-3',4'-disulfide)hexyl esters; and
(3',4'-Disulfide)cyclononane esters.
Bis-(2-bromoethyl) esters;

Bis-(2-aminoethyl) esters;
Bis-(2-N,N-diaminoethyl) esters;

Examples of preferred compounds include, but are not limited to those described in Table 1 including salts and prodrugs thereof:

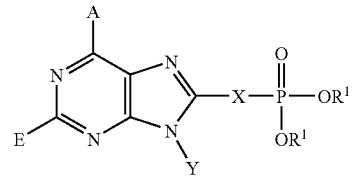

| Table Compound No. | Synthetic Example No. | A | E | Y | X |
|---|---|---|---|---|---|
| 1 | 2.7 | NH2 | H | neopentyl | 2,5-furanyl |
| 2 | | H | H | neopentyl | 2,5-furanyl |
| 3 | | Me | H | neopentyl | 2,5-furanyl |
| 4 | | Et | H | neopentyl | 2,5-furanyl |
| 5 | | Pr | H | neopentyl | 2,5-furanyl |
| 6 | | I | H | neopentyl | 2,5-furanyl |
| 7 | | Br | H | neopentyl | 2,5-furanyl |
| 8 | | Cl | H | neopentyl | 2,5-furanyl |
| 9 | | F | H | neopentyl | 2,5-furanyl |
| 10 | | OMe | H | neopentyl | 2,5-furanyl |
| 11 | | OEt | H | neopentyl | 2,5-furanyl |
| 12 | | OPr | H | neopentyl | 2,5-furanyl |
| 13 | | SMe | H | neopentyl | 2,5-furanyl |
| 14 | | SEt | H | neopentyl | 2,5-furanyl |
| 15 | | SPr | H | neopentyl | 2,5-furanyl |
| 16 | | SBn | H | neopentyl | 2,5-furanyl |
| 17 | | OBn | H | neopentyl | 2,5-furanyl |
| 18 | | NHMe | H | neopentyl | 2,5-furanyl |
| 19 | | NHEt | H | neopentyl | 2,5-furanyl |
| 20 | | NH-cPr | H | neopentyl | 2,5-furanyl |
| 21 | | NHOH | H | neopentyl | 2,5-furanyl |
| 22 | | NHNH2 | H | neopentyl | 2,5-furanyl |
| 23 | | NHCHO | H | neopentyl | 2,5-furanyl |
| 24 | | NHAc | H | neopentyl | 2,5-furanyl |
| 25 | | NHCOCF3 | H | neopentyl | 2,5-furanyl |
| 26 | | NHSO2Me | H | neopentyl | 2,5-furanyl |
| 27 | | CONH2 | H | neopentyl | 2,5-furanyl |
| 28 | | ONH2 | H | neopentyl | 2,5-furanyl |
| 29 | 22.2 | NH2 | SMe | neopentyl | 2,5-furanyl |
| 30 | | H | SMe | neopentyl | 2,5-furanyl |
| 31 | | Me | SMe | neopentyl | 2,5-furanyl |
| 32 | | Et | SMe | neopentyl | 2,5-furanyl |
| 33 | | Pr | SMe | neopentyl | 2,5-furanyl |
| 34 | | I | SMe | neopentyl | 2,5-furanyl |
| 35 | | Br | SMe | neopentyl | 2,5-furanyl |
| 36 | | Cl | SMe | neopentyl | 2,5-furanyl |
| 37 | | F | SMe | neopentyl | 2,5-furanyl |
| 38 | | OMe | SMe | neopentyl | 2,5-furanyl |
| 39 | | OEt | SMe | neopentyl | 2,5-furanyl |
| 40 | | OPr | SMe | neopentyl | 2,5-furanyl |
| 41 | | SMe | SMe | neopentyl | 2,5-furanyl |
| 42 | | SEt | SMe | neopentyl | 2,5-furanyl |
| 43 | | SPr | SMe | neopentyl | 2,5-furanyl |
| 44 | | SBn | SMe | neopenryl | 2,5-furanyl |
| 45 | | OBn | SMe | neopentyl | 2,5-furanyl |
| 46 | | NHMe | SMe | neopentyl | 2,5-furanyl |
| 47 | | NHEt | SMe | neopentyl | 2,5-furanyl |
| 48 | | NH-cPr | SMe | neopentyl | 2,5-furanyl |
| 49 | | NHOH | SMe | neopentyl | 2,5-furanyl |
| 50 | | NHNH2 | SMe | neopentyl | 2,5-furanyl |
| 51 | | NHCHO | SMe | neopentyl | 2,5-furanyl |
| 52 | | NHAc | SMe | neopentyl | 2,5-furanyl |
| 53 | | NHCOCF3 | SMe | neopentyl | 2,5-furanyl |
| 54 | | NHSO2Me | SMe | neopentyl | 2,5-furanyl |
| 55 | | CONH2 | SMe | neopentyl | 2,5-furanyl |
| 56 | | ONH2 | SMe | neopentyl | 2,5-furanyl |
| 57 | | NH2 | H | isobutyl | 2,5-furanyl |
| 58 | 2.6 | NH2 | H | isopropyl | 2,5-furanyl |
| 59 | 2.5 | NH2 | H | ethyl | 2,5-furanyl |
| 60 | | NH2 | H | methyl | 2,5-furanyl |
| 61 | 2.9 | NH2 | H | cyclopropyl | 2,5-furanyl |

-continued

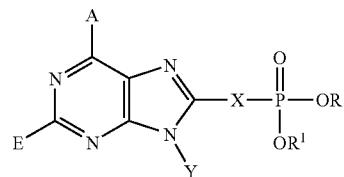

| Table Compound No. | Synthetic Example No. | A | E | Y | X |
|---|---|---|---|---|---|
| 62 |  | NH2 | H | cyclobutyl | 2,5-furanyl |
| 63 | 2.10 | NH2 | H | cyclopentyl | 2,5-furanyl |
| 64 |  | NH2 | H | cyclohexyl | 2,5-furanyl |
| 65 |  | NH2 | H | cycloheptanyl | 2,5-furanyl |
| 66 |  | NH2 | H | cyclopropylmethyl | 2,5-furanyl |
| 67 |  | NH2 | H | cyclobutylmethyl | 2,5-furanyl |
| 68 |  | NH2 | H | cyclopentylmethyl | 2,5-furanyl |
| 69 |  | NH2 | H | 2-cyclopropylethyl | 2,5-furanyl |
| 70 |  | NH2 | H | 2-cyclobutylethyl | 2,5-furanyl |
| 71 |  | NH2 | H | 2-cyclopentylethyl | 2,5-furanyl |
| 72 | 2.2 | NH2 | H | 2-cyclohexylethyl | 2,5-furanyl |
| 73 | 2.1 | NH2 | H | 2-phenylethyl | 2,5-furanyl |
| 74 |  | NH2 | H | benzyl | 2,5-furanyl |
| 75 |  | NH2 | H | phenyl | 2,5-furanyl |
| 76 |  | NH2 | H | D-ribosyl | 2,5-furanyl |
| 77 |  | NH2 | H | H | 2,5-furanyl |
| 78 |  | NH2 | H | 1-naphthylmethyl | 2,5-furanyl |
| 79 | 2.3 | NH2 | H | 2-naphthylmethyl | 2,5-furanyl |
| 80 |  | NH2 | H | 3-cyclopropylpropyl | 2,5-furanyl |
| 81 |  | NH2 | H | 3-cyclobutylpropyl | 2,5-furanyl |
| 82 |  | NH2 | H | 3-cyclopentylpropyl | 2,5-furanyl |
| 83 |  | NH2 | H | 3-cyclohexylpropyl | 2,5-furanyl |
| 84 | 2.4 | NH2 | H | 2,2-diphenylethyl | 2,5-furanyl |
| 85 | 2.8 | NH2 | H | adamentylmethyl | 2,5-furanyl |
| 86 | 2.11 | NH2 | H | 2-ethoxybenzyl | 2,5-furanyl |
| 87 | 2.13 | NH2 | H | 2,2-dimethyl-3-hydroxy-1-propyl | 2,5-furanyl |
| 88 | 2.12 | NH2 | H | 2,2-dimethyl-3-dimethylamino-1-propyl | 2,5-furanyl |
| 89 | 2.14 | NH2 | H | 2,2-dimethyl-3-chloro-1-propyl | 2,5-furanyl |
| 90 | 2.15 | NH2 | H | 3,3-dimethyl-1-butyl | 2,5-furanyl |
| 91 | 2.17 | NH2 | H | 1,2,2-trimethyl-1-propyl | 2,5-furanyl |
| 92 | 2.16 | NH2 | H | 1,5,5-trimethyl-3-ene-1-cyclohexylmethyl | 2,5-furanyl |
| 93 |  | NH2 | H | 4-pyrimidylmethyl | 2,5-furanyl |
| 94 |  | NH2 | H | 2-(4-pyrimidyl)ethyl | 2,5-furanyl |
| 95 |  | NH2 | H | 5-pyrimidylmethyl | 2,5-furanyl |
| 96 |  | NH2 | H | 2-(5-pyrimidyl)ethyl | 2,5-furanyl |
| 97 |  | NH2 | H | 2-pyrimidylmethyl | 2,5-furanyl |
| 98 |  | NH2 | H | 2-(2-pyrimidyl)ethyl | 2,5-furanyl |
| 99 |  | NH2 | H | 2-pyridylmethyl | 2,5-furanyl |
| 100 |  | NH2 | H | 2-(2-pyridyl)ethyl | 2,5-furanyl |
| 101 |  | NH2 | H | 3-pyridylmethyl | 2,5-furanyl |
| 102 |  | NH2 | H | 2-(3-pyridyl)ethyl | 2,5-furanyl |
| 103 |  | NH2 | H | 4-pyridylmethyl | 2,5-furanyl |
| 104 |  | NH2 | H | 2-(4-pyridyl)ethyl | 2,5-furanyl |
| 105 |  | NH2 | H | 2-carbamoylethyl | 2,5-furanyl |
| 106 |  | NH2 | H | 1-(2-carbamoyl)propyl | 2,5-furanyl |
| 107 |  | NH2 | H | neopentyl | CONHCH2 |
| 108 |  | NH2 | H | neopentyl | CONHCH2CH2 |
| 109 |  | NH2 | H | neopentyl | CH2CH2CH2 |
| 110 |  | NH2 | H | neopentyl | CH2CH2CF2 |
| 111 | 5.5 | NH2 | H | neopentyl | CH2OCH2 |
| 112 |  | NH2 | H | neopentyl | CH2OCF2 |
| 113 |  | NH2 | H | neopentyl | CF2CF2CF2 |
| 114 |  | NH2 | H | neopentyl | acetylene |
| 115 |  | NH2 | H | neopentyl | SCH2 |

-continued

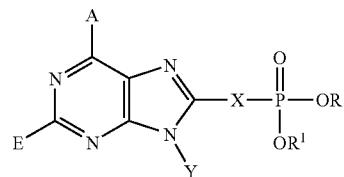

| Table Compound No. | Synthetic Example No. | A | E | Y | X |
|---|---|---|---|---|---|
| 116 | | NH2 | H | neopentyl | SCH2CH2 |
| 117 | | NH2 | H | neopentyl | CH2SCH2 |
| 118 | | NH2 | H | neopentyl | NHCH2CH2 |
| 119 | | NH2 | H | neopentyl | N(Ac)CH2CH2 |
| 120 | | NH2 | H | neopentyl | N(Bz)CH2CH2 |
| 121 | | NH2 | H | neopentyl | N(Me)CH2CH2 |
| 122 | | NH2 | H | neopentyl | N(Bn)CH2CH2 |
| 123 | | NH2 | H | neopentyl | NHCOCH2 |
| 124 | | NH2 | H | neopentyl | NHCOCH2CH2 |
| 125 | | NH2 | H | neopentyl | NHCOCF2 |
| 126 | | NH2 | H | neopentyl | NHSO2CH2 |
| 127 | | NH2 | H | neopentyl | N(Me)COCH2 |
| 128 | | NH2 | H | neopentyl | N(Bn)COCH2 |
| 129 | | NH2 | H | neopentyl | NHOCH2 |
| 130 | | NH2 | H | neopentyl | CH2CH2CH(OH) |
| 131 | | NH2 | H | neopentyl | CH2CH2CH(CO2H) |
| 132 | | NH2 | H | neopentyl | CH2CH2CH(SO3H) |
| 133 | | NH2 | H | neopentyl | CH2CH2CH(PO3H2) |
| 134 | 20.1 | NH2 | H | neopentyl | CH2-(1,2-imidazyl) |
| 135 | | NH2 | H | neopentyl | CH2-(1,2-pyrrolyl) |
| 136 | | NH2 | H | neopentyl | CSNHCH2 |
| 137 | | NH2 | H | neopentyl | 2,5-tetrahydrofuranyl |
| 138 | | NH2 | H | neopentyl | 2,5-pyrrolidinyl |
| 139 | | NH2 | H | neopentyl | 3,4-dihydroxy-2,5-terrahydrofuranyl |
| 140 | | NH2 | H | neopentyl | 2,4-furanyl |
| 141 | | NH2 | H | neopentyl | 4,2-furanyl |
| 142 | | NH2 | H | neopentyl | 2,5-thienyl |
| 143 | | NH2 | H | neopentyl | 2,4-thienyl |
| 144 | | NH2 | H | neopentyl | 4,2-thienyl |
| 145 | | NH2 | H | neopentyl | 2,5-pyrroly1 |
| 146 | | NH2 | H | neopentyl | 2,5-imidazyl |
| 147 | | NH2 | H | neopentyl | 5,2-imidazyl |
| 148 | | NH2 | H | neopentyl | 2,5-oxazyl |
| 149 | | NH2 | H | neopentyl | 5,2-oxazyl |
| 150 | 12.1 | NH2 | H | neopentyl | 3,4-dichloro-2,5-furanyl |
| 151 | | NH2 | H | neopentyl | 3-chloro-2,5-furanyl |
| 152 | | NH2 | H | neopentyl | 4-chloro-2,5-furanyl |
| 153 | | NH2 | H | neopentyl | 3,4-fluoro-2,5-furanyl |
| 154 | | NH2 | H | neopentyl | 3-fluoro-2,5-furanyl |
| 155 | | NH2 | H | neopentyl | 4-fluoro-2,5-furanyl |
| 156 | | NH2 | H | neopentyl | CONHCH(CO2H) |
| 157 | | NH2 | Me | neopentyl | 2,5-furanyl |
| 158 | | NH2 | Et | neopentyl | 2,5-furanyl |
| 159 | | NH2 | Pr | neopentyl | 2,5-furanyl |
| 160 | | NH2 | vinyl | neopentyl | 2,5-furanyl |
| 161 | | NH2 | acetylenyl | neopentyl | 2,5-furanyl |
| 162 | | NH2 | allyl | neopentyl | 2,5-furanyl |
| 163 | | NH2 | 2-furanyl | neopentyl | 2,5-furanyl |
| 164 | | NH2 | 3-furanyl | neopentyl | 2,5-furanyl |
| 165 | | NH2 | 2-thienyl | neopentyl | 2,5-furanyl |
| 166 | | NH2 | 3-thienyl | neopentyl | 2,5-furanyl |
| 167 | | NH2 | Ph | neopentyl | 2,5-furanyl |
| 168 | 22.1 | NH2 | NH2 | neopentyl | 2,5-furanyl |
| 169 | | NH2 | NHMe | neopentyl | 2,5-furanyl |
| 170 | | NH2 | N(Me)2 | neopentyl | 2,5-furanyl |
| 171 | | NH2 | NHBn | neopentyl | 2,5-furanyl |
| 172 | | NH2 | I | neopentyl | 2,5-furanyl |
| 173 | | NH2 | Br | neopentyl | 2,5-furanyl |

-continued

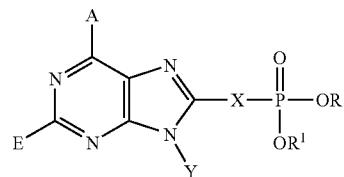

| Table Compound No. | Synthetic Example No. | A | E | Y | X |
|---|---|---|---|---|---|
| 174 | | NH2 | Cl | neopentyl | 2,5-furanyl |
| 175 | | NH2 | F | neopentyl | 2,5-furanyl |
| 176 | | NH2 | OMe | neopentyl | 2,5-furanyl |
| 177 | | NH2 | OEt | neopentyl | 2,5-furanyl |
| 178 | | NH2 | OPr | neopentyl | 2,5-furanyl |
| 179 | | NH2 | SO2Me | neopentyl | 2,5-furanyl |
| 180 | | NH2 | SEt | neopentyl | 2,5-furanyl |
| 181 | | NH2 | SPr | neopentyl | 2,5-furanyl |
| 182 | | NH2 | SBu | neopentyl | 2,5-furanyl |
| 183 | | NH2 | ON | neopentyl | 2,5-furanyl |
| 184 | | NH2 | CONH2 | neopentyl | 2,5-furanyl |
| 185 | | NH2 | 2-pyridyl | neopentyl | 2,5-furanyl |
| 186 | | NH2 | 3-pyridyl | neopentyl | 2,5-furanyl |
| 187 | | NH2 | 4-pyridyl | neopentyl | 2,5-furanyl |
| 188 | 5.4 | NH2 | H | 1-(3-cyclohexyl)propyl | CH2OCH2 |
| 189 | 5.3 | NH2 | H | 1-nonyl | CH2OCH2 |
| 190 | 5.2 | NH2 | H | 2-cyclohexylethyl | CH2OCH2 |
| 191 | 5.1 | NH2 | H | 2-phenethyl | CH2OCH2 |
| 192 | 10.2 | NHMe | H | 2-phenethyl | 2,5-furanyl |
| 193 | 10.1 | N(Me)2 | H | 2-phenethyl | 2,5-furanyl |
| 194 | 9.1 | Cl | H | 2-phenethyl | 2,5-furanyl |
| 195 | 11.1 | NH2 | SMe | isobutyl | 2,5-furanyl |
| 196 | 11.2 | NH2 | SO2Me | isobutyl | 2,5-furanyl |
| 197 | 4.1 | NH2 | H | D-ribosyl | NHCH2CH2 |
| 198 | 4.2 | NH2 | H | 5'-deoxy-D-ribosyl | NHCH2CH2 |
| 199 | | NH2 | H | H | NHCH2CH2 |
| 200 | 3.1 | NH2 | H | benzyl | NHCH2CH2 |
| 201 | 3.2 | NH2 | H | 2-phenethyl | NHCH2CH2 |
| 202 | 3.3 | NH2 | H | 2-naphthylmethyl | NHCH2CH2 |
| 203 | 6.2 | NH2 | H | 2-phenethyl | CH2CH2CH2 |
| 204 | 3.4 | NH2 | H | 2-cyclohexylethyl | NHCH2CH2 |
| 205 | 6.1 | NH2 | H | 2-cyclohexylethyl | CH2CH2CH2 |
| 206 | 8.1 | NH2 | H | 2-cyclohexylerhyl | SCH2 |
| 207 | 7.1 | NH2 | H | 2-phenethyl | 2,5-thienyl |
| 208 | | NH2 | Me | isobutyl | 2,5-furanyl |
| 209 | | NH2 | Et | isobutyl | 2,5-furanyl |
| 210 | | NH2 | SEt | isobutyl | 2,5-furanyl |
| 211 | | NH2 | SPr | isobutyl | 2,5-furanyl |
| 212 | | NH2 | 2-furanyl | isobutyl | 2,5-furanyl |
| 213 | | NH2 | 2-thienyl | isobutyl | 2,5-furanyl |
| 214 | | NH2 | Pr | isobutyl | 2,5-furanyl |
| 215 | | NH2 | F | isobutyl | 2,5-furanyl |
| 216 | | NH2 | Cl | isobutyl | 2,5-furanyl |
| 217 | | NH2 | Br | isobutyl | 2,5-furanyl |
| 218 | | NH2 | H | isobutyl | 2,5-furanyl |
| 219 | | NH2 | Et | isobutyl | CONHCH2 |
| 220 | | NH2 | SEt | isobutyl | CONHCH2 |
| 221 | | NH2 | SPr | isobutyl | CONHCH2 |
| 222 | | NH2 | 2-furanyl | isobutyl | CONHCH2 |
| 223 | | NH2 | 2-thienyl | isobutyl | CONHCH2 |
| 224 | | NH2 | Pr | isobutyl | CONHCH2 |
| 225 | | NH2 | F | isobutyl | CONHCH2 |
| 226 | | NH2 | Cl | isobutyl | CONHCH2 |
| 227 | | NH2 | Br | isobutyl | CONHCH2 |
| 228 | | NH2 | Me | isobutyl | CONHCH2 |
| 229 | | NH2 | H | isobutyl | CONHCH2 |
| 230 | | NH2 | Et | neopentyl | acetylene |
| 231 | | NH2 | SEt | neopentyl | acetylene |
| 232 | | NH2 | SPr | neopentyl | acetylene |
| 233 | | NH2 | 2-furanyl | neopentyl | acetylene |
| 234 | | NH2 | 2-thienyl | neopentyl | acetylene |
| 235 | | NH2 | Pr | neopentyl | acetylene |
| 236 | | NH2 | F | neopentyl | acetylene |
| 237 | | NH2 | Cl | neopentyl | acetylene |
| 238 | | NH2 | Br | neopentyl | acetylene |
| 239 | | NH2 | Me | neopentyl | acetylene |
| 240 | | NH2 | Et | neopentyl | NHCOCH2 |
| 241 | | NH2 | SEt | neopentyl | NHCOCH2 |

-continued

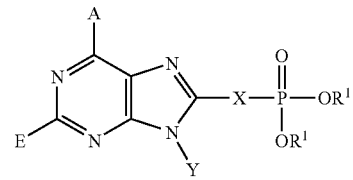

| Compound No. | Synthetic Example No. | A | E | Y | |
|---|---|---|---|---|---|
| 242 | | NH2 | SPr | neopentyl | NHCOCH2 |
| 243 | | NH2 | 2-furanyl | neopentyl | NHCOCH2 |
| 244 | | NH2 | 2-thienyl | neopentyl | NHCOCH2 |
| 245 | | NH2 | Pr | neopentyl | NHCOCH2 |
| 246 | | NH2 | F | neopentyl | NHCOCH2 |
| 247 | | NH2 | Cl | neopentyl | NHCOCH2 |
| 248 | | NH2 | Br | neopentyl | NHCOCH2 |
| 249 | | NH2 | Me | neopentyl | NHCOCH2 |
| 250 | | NH2 | Et | neopentyl | CH2OCH2 |
| 251 | | NH2 | SEt | neopentyl | CH2OCH2 |
| 252 | | NH2 | SPr | neopentyl | CH2OCH2 |
| 253 | | NH2 | 2-furanyl | neopentyl | CH2OCH2 |
| 254 | | NH2 | 2-thienyl | neopentyl | CH2OCH2 |
| 255 | | NH2 | Pr | neopentyl | CH2OCH2 |
| 256 | | NH2 | F | neopentyl | CH2OCH2 |
| 257 | | NH2 | Cl | neopentyl | CH2OCH2 |
| 258 | | NH2 | Br | neopentyl | CH2OCH2 |
| 259 | | NH2 | Me | neopentyl | CH2OCH2 |
| 260 | | NHBn | H | neopentyl | 2,5-furanyl |
| 261 | | NHPh | H | neopentyl | 2,5-furanyl |
| 262 | | NHBn | SMe | neopentyl | 2,5-furanyl |
| 263 | | NHPh | SMe | neopentyl | 2,5-furanyl |
| 264 | | NHPh-4-F | H | neopentyl | 2,5-furanyl |
| 265 | | NHPh-4-F | SMe | neopentyl | 2,5-furanyl |
| 266 | | NHNH2 | F | neopentyl | 2,5-furanyl |
| 267 | | NH2 | Me | cyclopropylmethyl | 2,5-furanyl |
| 268 | | NH2 | SMe | cyclopropylmethyl | 2,5-furanyl |
| 269 | | NH2 | F | cyclopropylmethyl | 2,5-furanyl |
| 270 | | NH2 | Cl | cycloprylmethy | 2,5-furanyl |
| 271 | | NH2 | Br | cyclopropylmethyl | 2,5-furanyl |
| 272 | | NH2 | Et | cyclopropylmethyl | 2,5-furanyl |
| 273 | | NH2 | CN | cyclopropylmethyl | 2,5-furanyl |
| 274 | | NH2 | Me | cyclopropylmethyl | CONHCH2 |
| 275 | | NH2 | SMe | cyclopropylmethyl | CONHCH2 |
| 276 | | NH2 | F | cyclopropylmethyl | CONHCH2 |
| 277 | | NH2 | Cl | cycloprylmethyl | CONHCH2 |
| 278 | | NH2 | Br | cyclopropylmethyl | CONHCH2 |
| 279 | | NH2 | Et | cyclopropylmethyl | CONHCH2 |
| 280 | | NH2 | CN | cyclopropylmethyl | CONHCH2 |
| 281 | | NH2 | Me | cyclopropylmethyl | NHCOCH2 |
| 282 | | NH2 | SMe | cyclopropylmethyl | NHCOCH2 |
| 283 | | NH2 | F | cycloprylmethyl | NHCOCH2 |
| 284 | | NH2 | Cl | cyclopropylmethyl | NHCOCH2 |
| 285 | | NH2 | Br | cyclopropylmethyl | NHCOCH2 |
| 286 | | NH2 | Et | cyclopropylmethyl | NHCOCH2 |
| 287 | | NH2 | CN | cyclopropylmethyl | NHCOCH2 |
| 288 | 2.18 | NH2 | H | 3-(1-imidazolylpropyl) | 2,5-furanyl |
| 289 | 19.1 | NH2 | H | neopentyl | 1,2-C6H4-O- |
| 290 | 21.1 | NH2 | H | 2-phenethyl | CONHCH2 |

More preferred are the following compounds from Table 1 including salts and prodrugs thereof:

1, 21, 22, 23, 29, 50, 57, 61, 62, 63, 66, 67, 72, 73, 89, 90, 107, 110, 111, 112, 113, 114, 115, 119, 123, 125, 126, 129, 130, 131, 132, 133, 134, 136, 137, 145, 148, 149, 151, 152, 153, 154, 155, 156, 158, 159, 163, 165, 173, 174, 175, 180, 181, 182, 183, 209, 210, 212, 215, 216, 217, 219, 220, 221, 230, 231, 234, 236, 237, 238, 240, 241, 246, 247, 248, 250, 251, 256, 257, 258, 266, 268, 269, and 272.

Most preferred are the following compounds and their salts and prodrugs:

$N^9$-neopentyl-2-methylthio-8-phosphonomethylaminocarbonyladenine;

$N^9$-neopentyl-2-methylthio-8-(2-(5-phosphono)furanyl)adenine;

$N^9$-neopentyl-8-(2-(5-phosphono)furanyl)adenine;

$N^9$-isobutyl-2-methylthio-8-(2-(5-phosphono)furanyl)adenine;

$N^9$-isobutyl-8-(2-(5-phosphono)furanyl)adenine;

$N^9$-cyclopropyl-8-(2-(5-phosphono)furanyl)adenine;

$N^9$-(2-cyclohexyl)ethyl-8-(2-(5-phosphono)furanyl)adenine;

$N^9$-(1-(2,2-dimethyl-3-chloro)propyl)-8-(2-(5-phosphono)furanyl)adenine;

$N^9$-(1-(3,3-dimethyl)butyl)-8-(2-(5-phosphono)furanyl)adenine;

9'-(1,5,5-trimethyl-3-cyclohexen-1-yl)methyl-8-(2-(5-phosphono)furanyl)adenine;

$N^9$-neopentyl-8-(2-phosphonoacetylene-1-yl)adenine;

$N^9$-neopentyl-8-(1-(3-phosphono-3-sulfuryl)propyl)adenine;

$N^9$-neopentyl-8-(1-(3-phosphono-3-carboxyl)propyl)adenine;

$N^9$-neopentyl-8-(1-(3,3-diphosphono)propyl)adenine;

$N^9$-neopentyl-2-chloro-8-(2-(5-phosphono)furanyl)adenine;

2-Ethyl-$N^9$-neopentyl-8-(2-(5-phosphono)furanyl)adenine;

2-Methylthio-$N^9$-isobutyl-8-(2-(5-phosphono)furanyl)adenine; and

2-Methylthio-$N^9$-isobutyl-8-(phosphonomethoxymethyl)adenine.

Synthesis of Compounds of Formula 1

Synthesis of compounds encompassed by the present invention typically includes some or all of the following general steps: (1) preparation of phosphonate prodrug; (2) deprotection of phosphonate ester; (3) modification of C-8-substituted purine intermediates; (4) modification of purine at positions other than C-8; (5) construction of the purine ring system; and (6) preparation of 4,5-diaminopyrimidine and other coupling partners.

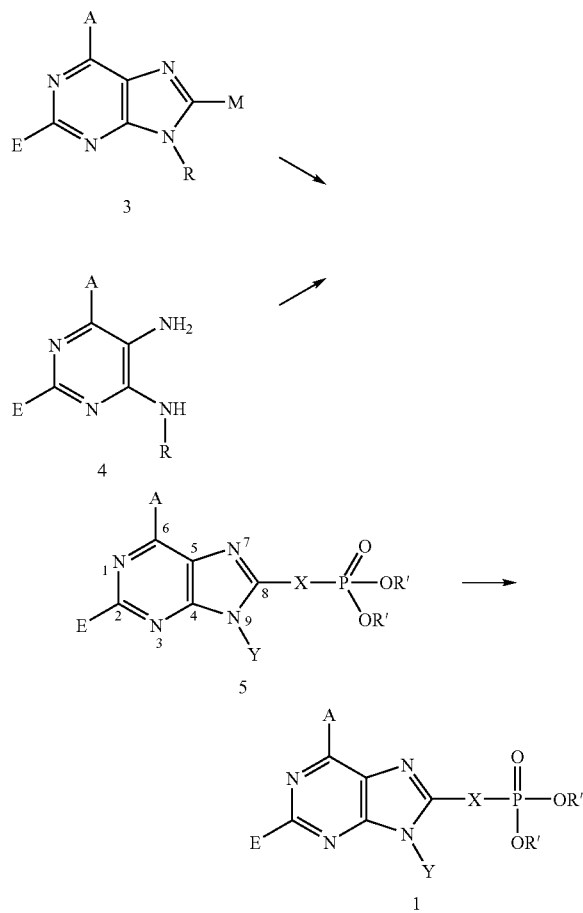

(1) Preparation of Phosphonate Prodrugs

Prodrug esters can be introduced at different stages of the synthesis. Because of their lability, prodrugs are often prepared from compounds of formula 1 where $R^1$ is H. Advantageously, these prodrug esters can be introduced at an early stage, provided that it can withstand the reaction conditions of the subsequent steps.

Compounds of formula 5 where $R^1$ is H, can be alkylated with electrophiles (such as alkyl halides, alkyl sulfonates etc) under nucleophilic substitution reaction conditions to give phosphonate esters. For example prodrugs of formula 1, where $R^1$ is acyloxymethyl group can be synthesized through direct alkylation of the free phosphonic acid of formula 5, with the desired acyloxymethyl halide (e.g. Cl, Br, I; Elhaddadi, et al *Phosphorus Sulfur,* 1990, 54(1-4): 143; Hoffmann, *Synthesis,* 1988, 62) in presence of base e.g. N,N'-dicyclohexyl-4-morpholinecarboxamidine, Hunigs base etc. in polar aprotic solvents such as DMF (Starrett, et al, *J. Med. Chem.,* 1994, 1857). These carboxylates include but not limited to acetate, propylate, isobutyrate, pivalate, benzoate, and other carboxylates. Alternately, these acyloxymethylphosphonate esters can also be synthesized by treatment of the nitrophosphonic acid (A is $NO_2$ in formula 5; Dickson, et al, *J. Med. Chem.,* 1996, 39: 661; Iyer, et al, *Tetrahedron Lett.,* 1989, 30: 7141; Srivastva, et al, *Bioorg. Chem.,* 1984, 12: 118). This can be extended to many other types of prodrugs, such as compounds of formula 1 where $R^1$ is 3-phthalidyl, 2-oxo-4,5-didehydro-1,3-dioxolanemethyl, and 2-oxotetrahydrofuran-5-yl groups, etc. (Biller and Magrin (U.S. Pat. No. 5,157,027); Serafinowska et al. (*J. Med. Chem.* 38: 1372 (1995)); Starrett et al. (*J. Med. Chem.* 37: 1857 (1994)); Martin et al. *J. Pharm. Sci.* 76: 180 (1987); Alexander et al., *Collect. Czech. Chem. Commun,* 59: 1853 (1994)); and EPO 0632048A1). N,N-Dimethylformamide dialkyl acetals can also be used to alkylate phosphonic acids (Alexander, P., et al *Collect. Czech. Chem. Commun.,* 1994, 59, 1853).

Alternatively, these phosphonate prodrugs or phosphoramidates can also be synthesized, by reaction of the corresponding dichlorophosphonates and an alcohol or an amine (Alexander, et al, *Collect. Czech. Chem. Commun.,* 1994, 59: 1853). For example, the reaction of dichlorophosphonate with phenols and benzyl alcohols in the presence of base (such as pyridine, triethylamine, etc) yields compounds of formula 1 where $R^1$ is aryl (Khamnei, S., et al *J. Med. Chem.,* 1996, 39: 4109; Serafinowska, H. T., et al *J. Med. Chem.,* 1995, 38: 1372; De Lombaert, S., et al *J. Med. Chem.,* 1994, 37: 498) or benzyl (Mitchell, A. G., et al *J. Chem. Soc. Perkin Trans.* 1, 1992, 38: 2345). The disulfide-containing prodrugs, reported by Puech et al., *Antiviral Res.,* 1993, 22: 155, can also be prepared from dichlorophosphonate and 2-hydroxyethyl disulfide under the standard conditions.

Such reactive dichlorophosphonate intermediates, can be prepared from the corresponding phosphonic acids and the chlorinating agents e.g. thionyl chloride (Starrett, et al, *J. Med. Chem.,* 1994, 1857), oxalyl chloride (Stowell, et al, *Tetrahedron Lett.,* 1990, 31: 3261), and phosphorus pentachloride (Quast, et al, *Synthesis,* 1974, 490). Alternatively, these dichlorophosphonates can also be generated from disilyl phosphonate esters (Bhongle, et al, *Synth. Commun.,* 1987, 17: 1071) and dialkyl phosphonate esters (Still, et al, *Tetrahedron Lett.,* 1983, 24: 4405; Patois, et al, *Bull. Soc. Chim. Fr.,* 1993, 130: 485).

Furthermore, these prodrugs can be prepared from Mitsunobu reactions (Mitsunobu, *Synthesis,* 1981, 1; Campbell, *J. Org. Chem.,* 1992, 52: 6331), and other acid coupling reagents include, but not limited to, carbodiimides (Alexander, et al, *Collect. Czech. Chem. Commun.,* 1994, 59: 1853; Casara, et al, *Bioorg. Med. Chem. Lett.,* 1992, 2: 145; Ohashi, et al, *Tetrahedron Lett.,* 1988, 29: 1189), and benzotriazolyloxytris-(dimethylamino)phosphonium salts (Campagne, et al, *Tetrahedron Lett.*, 1993, 34: 6743). The prodrugs of formula 1 where R¹ is the cyclic carbonate or lactone or phthalidyl can also be synthesized by direct alkylation of free phosphonic acid with desired halides in the presence of base such as NaH or diisopropylethylamine (Biller and Magnin U.S. Pat. No. 5,157,027; Serafinowska et al. *J. Med. Chem.* 38: 1372 (1995); Starrett et al. *J. Med. Chem.* 37: 1857 (1994); Martin et al. *J. Pharm. Sci.* 76: 180 (1987); Alexander et al., *Collect. Czech. Chem. Commun*, 59: 1853 (1994); and EPO 0632048A1).

R¹ can also be introduced at an early stage of synthesis, when feasible. For example, compounds of formula 1 where R¹ is phenyl can be prepared by phosphorylation of 2-furanylpurines via strong base treatment (e.g. LDA) followed by chlorodiphenylphosphonate, as shown in the following scheme. Alternatively, such compounds can be prepared by cyclization of 5-diphenylphosphono-2-furaldehyde with 4,5-diaminopyrimidines as described in section 5.

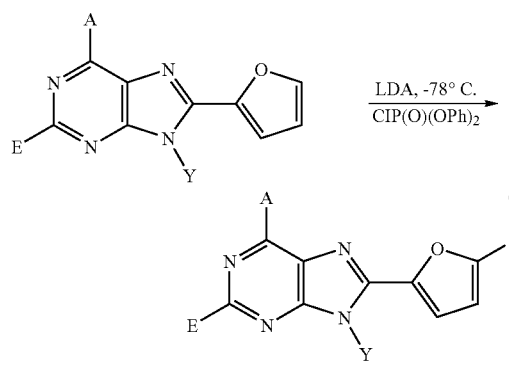

It is envisioned that compounds of formula 1 can be mixed phosphonate esters phenyl acyloxyalkyl phosphonate esters, etc.). For example, the chemically combined phenylbenzyl prodrugs are reported by Meier et al. *Bioorg. Med. Chem. Lett.*, 1997, 7: 99.

The substituted cyclic propyl phosphonate esters of formula 5, can be synthesized by reaction of the corresponding dichlorophosphonate and the substituted 1,3-propanediol. The following are some of the methods to prepare the substituted 1,3-propanediols.

Synthesis of the 1,3-Propanediols Used in the Preparation of Certain Prodrugs

The discussion of this step includes various synthetic methods for the preparation of the following types of propane-1,3-diols: i) 1-substituted; ii) 2-substituted; and iii) 1,2- or 1,3-annulated. Different groups on the prodrug part of the molecule i.e., on the propanediol moiety can be introduced or modified either during the synthesis of the diols or after the synthesis of the prodrugs.

i) 1-Substituted 1,3-Propanediols

Propane-1,3-diols can be synthesized by several well known methods in the literature. Aryl Grignard additions to 1-hydroxypropan-3-al gives 1-aryl-substituted propane-1,3-diols (path a). This method will enable conversion of various substituted aryl halides to 1-arylsubstituted-1,3-propanediols (Coppi, et. al., *J. Org. Chem.*, 1988, 53, 911). Aryl halides can also be used to synthesize 1-substituted propanediols by Heck coupling of 1,3-diox-4-ene followed by reduction and hydrolysis (Sakamoto, et. al., *Tetrahedron Lett.*, 1992, 33, 6845). A variety of aromatic aldehydes can be converted to 1-substituted-1,3-propanediols by vinyl Grignard addition followed by hydroboration (path b). Substituted aromatic aldehydes are also utilized by lithium-t-butylacetate addition followed by ester reduction (path e) (Turner., *J. Org. Chem.*, 1990, 55 4744). In another method, commercially available cinnamyl alcohols can be converted to epoxy alcohols under catalytic asymmetric epoxidation conditions. These epoxy alcohols are reduced by Red-Al to result in enantiomerically pure propane-1,3-diols (path c). Alternatively, enantiomerically pure 1,3-diols can be obtained by chiral borane reduction of hydroxyethyl aryl ketone derivatives (Ramachandran, et. al., *Tetrahedron Lett.*, 1997, 38 761). Pyridyl, quinoline, and isoquinoline propan-3-ol derivatives can be oxygenated to 1-substituted propan-1,3-diols by N-oxide formation followed by rearrangement under acetic anhydride conditions (path d) (Yamamoto, et. al., *Tetrahedron*, 1981, 37, 1871).

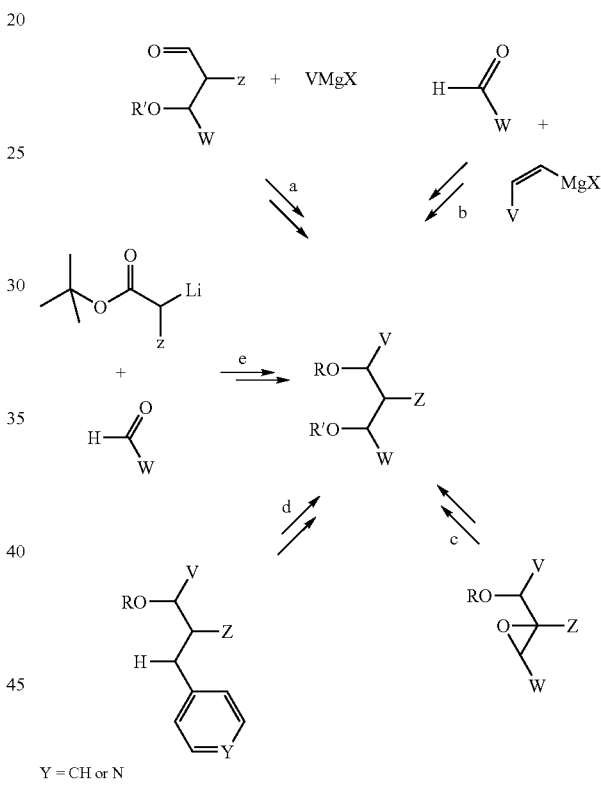

Y = CH or N ii) 2-Substituted 1,3-Propanediols:

Various 2-substituted propane-1,3-diols can be made from commercially available 2-(hydroxymethyl)-1,3-propanediol. Triethyl methanetricarboxylate can be converted to the triol by complete reduction (path a) or diol-monocarboxylic acid derivatives can be obtained by partial hydrolysis and diester reduction (Larock, *Comprehensive Organic Transformations*, VCH, New York, 1989). Nitrotriol is also known to give the triol by reductive elimination (path b) (Latour, et. al., *Synthesis*, 1987, 8, 742). The triol can be derivatized as a mono acetate or carbonate by treatment with alkanoyl chloride, or alkylchloroformate, respectively (path d) (Greene and Wuts, *Protective Groups in Organic Synthesis*, John Wiley, New York, 1990). Aryl substitution can be made by oxidation to the aldehyde followed by aryl Grignard additions (path c) and the aldehyde can also be converted to substituted amines by reductive animation reactions (path e).

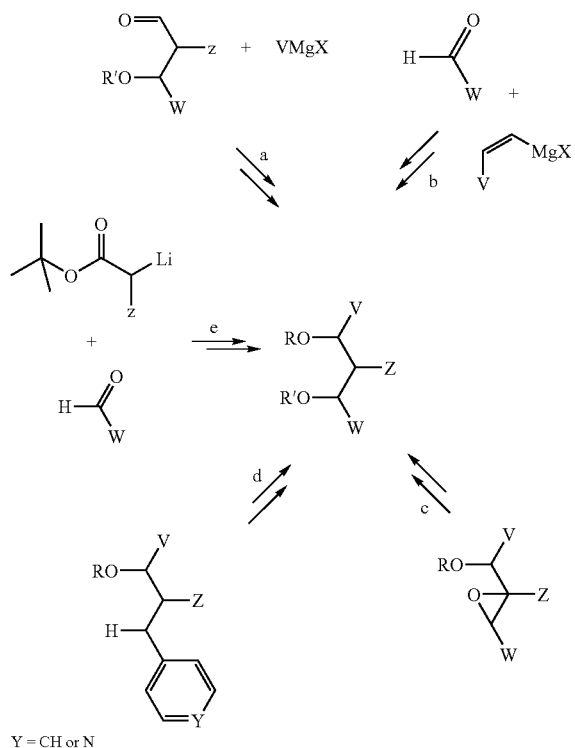

Y = CH or N iii) Annulated 1,3-Propanediols:

Prodrugs of formula 1 where V-Z or V-W are fused by three carbons are made from cyclohexanediol derivatives. Commercially available cis, cis-1,3,5-cyclohexanetriol can be used for prodrug formation. This cyclohexanetriol can also be modified as described in the case of 2-substituted propane-1,3-diols to give various analogues. These modifications can either be made before or after formation of prodrugs. Various 1,3-cyclohexanediols can be made by Diels-Alder methodology using pyrone as the diene (Posner, et. al., *Tetrahedron Lett.*, 1991, 32, 5295). Cyclohexyl diol derivatives are also made by nitrile oxide olefin-additions (Curran, et. al., *J. Am. Chem. Soc.*, 1985, 107, 6023). Alternatively, cyclohexyl precursors can be made from quinic acid (Rao, et. al., *Tetrahedron Lett.*, 1991, 32, 547.)

(2) Deprotection of Phosphonate Esters

Compounds of formula 1 where $R^1$ is H may be prepared from phosphonate esters using known phosphate and phosphonate ester cleavage conditions. For example, alkyl phosphonate esters are generally cleaved by reaction with silyl halides followed by hydrolysis of the intermediate silyl phosphonate esters. Depending on the stability of the products, these reactions are usually accomplished in the presence of acid scavengers such as 1,1,1,3,3,3-hexamethyldisilazane, 2,6-lutidine, etc. Various silyl halides can be used for this transformation, such as chlorotrimethylsilane (Rabinowitz *J. Org. Chem.*, 1963, 28: 2975), bromotrimethylsilane (McKenna et al. *Tetrahedron Lett.*, 1977, 155), iodotrimethylsilane (Blackburn et al. *J. Chem. Soc., Chem. Commun.*, 1978, 870). Phosphonate esters can also be cleaved under strong acid conditions, such as hydrogen halides in acetic acid or water, and metal halides (Moffatt et al. U.S. Pat. No. 3,524,846, 1970). Phosphonate esters can also be converted to dichlorophosphonates with halogenating agents (e.g. $PCl_5$, $SOCl_2$, $BBr_3$, etc. Pelchowicz et al. *J. Chem. Soc.*, 1961, 238) and subsequently hydrolyzed to give phosphonic acids. Reductive reactions are useful in cleaving aryl and benzyl phosphonate esters. For example, aryl and benzyl phosphonate esters can be cleaved under hydrogenolysis conditions (Lejczak et al. *Synthesis*, 1982, 412; Elliott et al. *J. Med. Chem.*, 1985, 28: 1208.) or dissolving metal reduction conditions (Shafer et al. *J. Am. Chem. Soc.*, 1977, 99: 5118). (Elliott et al. *J. Med. Chem.*, 1985, 28: 1208). Electrochemical (Shono et al. *J. Org. Chem.*, 1979, 44: 4508) and pyrolysis (Gupta et al. *Synth. Commun.*, 1980, 10: 299) conditions have also been used to cleave various phosphonate esters.

(3) Modification of C-8-Substituted Purine Intermediates

8-Substituted purines are useful intermediates in the preparation of compounds of formula 1. 8-Halopurines, which are particularly useful intermediates, are readily prepared using chemistry well described in the literature. For example, $N^9$-alkyladenines are halogenated at the C-8 position using known halogenating agents (e.g. $Br_2$, NBS). 8-Alkylpurine can be prepared through direct lithiation of purine followed by trapping with electrophiles (e.g. alkyl halides, Barton et al. *Tetrahedron Lett.*, 1979, 5877).

Functionalization of 8-halopurines can be accomplished under substitution reaction conditions with nucleophiles such as amines, alcohols, azides, sulfides, and alkylthiols. It is advantageous to have the phosphonate moiety as part of the nucleophiles. For example, substitution of 8-bromopurine with aminoalkylphosphonates gives compounds of formula 1 where X is alkylamino.

8-Halopurines can also be transformed into other 8-substituted purines using palladium catalyzed reactions (Heck *Palladium Reagents in Organic Synthesis*; Academic Press: San Diego, 1985). For example, palladium catalyzed carbonylation reactions of 8-bromopurine in the presence of alcohol gives 8-alkoxycarbonylpurines. Using known chemistry, the 8-carboxylate group can be converted into other functional groups, such as hydroxymethyl, halomethyl, formyl, carboxylic acid, carbamoyl, and thiocarbonyl groups. These functional groups are useful intermediates for the synthesis of compounds of formula 1. For example, 8-alkyl and 8-arylpurines can be prepared from 8-halopurines via palladium catalyzed coupling reactions with organotin (Moriarty et al. *Tetrahedron Lett.*, 1990, 41: 5877), organoborane (Yatagai, *Bull. Chem. Soc. Jpn.*, 1980, 53: 1670), and other reagents known to couple with aryl halides. When the coupling reagents contain the dialkylphosphonate group, the reaction is useful for preparation of compounds of formula 5 where X is alkyl, alkenyl, alkynyl, and aryl. For example, 8-bromopurine can be coupled with diethyl 1-tributylstannyl-3-allylphosphonate to give compounds of formula 5 where X is —CH=CHCH$_2$—. Subsequent hydrogenation reaction gives compounds of formula 5 where X is —CH$_2$CH$_2$CH$_2$—.

The phosphonate group can also be introduced by further modification of the 8-substituents. Substitutions of 8-haloalkyl or 8-sulfonylalkylpurine with nucleophiles containing the phosphonate group are useful for the preparation of compounds of formula 5 where X is alkylaminoalkyl, alkoxyalkyl, and alkylthioalkyl. For example, compounds of formula 5 where X is —CH$_2$OCH$_2$— can be prepared from 8-bromomethylpurine using hydroxymethylphosphonate esters and a suitable base. It is possible to reverse the nature of the nucleophiles and electrophiles for the substitution reactions, i.e. haloalkyl- and/or sulfonylalkylphosphonate esters can be substituted with purines containing a nucleophile at the C-8 position (such as 8-hydroxyalkyl, 8-thioalkyl, and 8-aminoalkylpurines). For example, diethyl phosphonomethyltriflate can be substituted by alcohols such as 8-hydroxymethylpurine to give compounds of formula 5 where X is —CH$_2$OCH$_2$— (Phillion et al. *Tetrahedron Lett.* 1986, 27: 1477). Known amide formation reactions are useful for the synthesis of compounds of formula 5 where X is alkylaminocarbonyl, alkoxycarbonyl, alkoxythiocarbonyl, and alkylthiocarbonyl. For example, coupling of 8-purinecarboxylic acids with aminoalkylphosphonate esters gives compounds of formula 5 where X is alkylaminocarbonyl. For compounds of formula 5 where X is alkyl, the phosphonate group can also be introduced using other common phosphonate formation methods, such as Michaelis-Arbuzov reaction (Bhattacharya et al. *Chem. Rev.*, 1981, 81: 415), Michaelis-Becker reaction (Blackburn et al. *J. Organomet. Chem.*, 1988, 348: 55), addition reactions of phosphorus to electrophiles (such as aldehydes, ketones, acyl halides, imines and other carbonyl derivatives).

8-Azidopurines are useful for the preparation for compounds of formula 5 where X is alkylamino and alkylcarbonylamino groups. For example, carboxylic acids (e.g. (RO)$_2$P(O)-alkyl-CO$_2$H) can be directly coupled to 8-azidopurines to give 8-alkylcarbonylaminopurines (Urpi et al. *Tetrahedron Lett.*, 1986, 27: 4623). Alternatively, 8-azidopurines can also be converted to 8-aminopurines under reductive conditions, and subsequently converted to 8-alkylaminocarbonyl- and 8-alkylaminopurines using known chemistry.

(4) Modification of Purines at Positions Other than C-8

Compounds of formula 5 can be further modified to give intermediates useful for the synthesis of compounds of formula 1. For example, substitution reactions of 6-chloropurine by ammonia or alkylamines are useful for the preparations of compounds of formula 5 where A is amino and alkylamino groups.

E groups can be introduced by modifying existing 2-substituents of purine. For example, 2-halopurines, readily accessible from 2-aminopurines via chemistry well described in the literature, can be converted to other 2-substituted purines by, for example, nucleophilic substitution reactions; transition metal catalyzed reactions, etc. (*J. Med. Chem.*, 1993, 36: 2938; *Heterocycles*, 1990, 30: 435).

E groups can also be introduced via metalation (e.g. lithiation, *J. Org. Chem.*, 1997, 62(20), 6833) of the C-2-position and followed by addition of electrophiles which can be the desired E group or a substituent (e.g. tributylstannyl group) which can be converted to the desired E group using conventional chemistry.

It is envisioned that N$^9$-substituted purines can be readily prepared from compounds of formula 5 where Y is H using, for example, standard alkylation reactions (with alkyl halide, or sulfonate), or Mitsunobu reactions. Further elaborations of substituents on Y are also possible.

More importantly, combinatorial methods have been developed for synthesis of 2- and N-9-substituted purines on solid-phase which conceivably can be applied for the synthesis of purine FBPase inhibitors (Schultz, et al, *Tetrahedron Lett.*, 1997, 38(7), 1161; *J. Am. Chem. Soc.*, 1996, 118, 7430).

(5) Construction of the Purine Ring System

The purine ring system of compounds of formula 1 can be constructed using 4,5-diaminopyrimidines and carboxylates or their derivatives (such as aldehydes, amides, nitriles, ortho esters, imidates, etc.) (Townsend *Chemistry of Nucleosides and Nucleotides*, Vol 1; Plenum Press, New York and London, page 156-158). For example, alkyl and aryl aldehydes can be cyclized with 4,5-diaminopyrimidines as shown below.

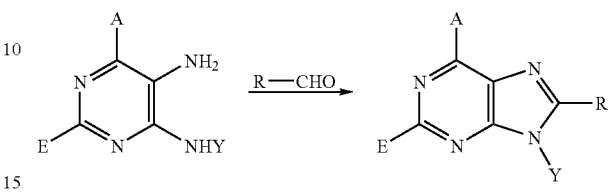

Intramolecular cyclization reactions of pyrimidine derivatives can also be used to construct the purine ring system. For example, 5-acylamino-4-alkylaminopyrimidines are treated with phosphorus oxychloride and cyclized under basic conditions to give purine derivatives. This transformation can also be achieved using other reagents (e.g. SiCl$_4$-Et$_3$N, Desaubry et al. *Tetrahedron Lett.*, 1995, 36: 4249). Imidazole derivatives are also useful for the construction of purine ring system via cyclization reactions to form the pyrimidine ring (Townsend *Chemistry of Nucleosides and Nucleotides*, Vol 1; Plenum Press, New York and London, page 148-156).

(6) Preparation of Diaminopyrimidine and Other Coupling Partners

Compounds of formula 4 are useful for the construction of purine ring systems, and such compounds can be readily synthesized using known chemistry. For example, the Y group can be introduced using a nucleophilic substitution reaction involving an amine and 4-halopyrimidines (*Tetrahedron*, 1984, 40: 1433). Alternatively, palladium catalyzed reactions (Wolfe et al. *J. Am. Chem. Soc.*, 1996, 118: 7215) can also be used. Reductive amination reactions (*Synthesis*, 1975, 135) and alkylation with electrophiles (such as halides, sulfonates) are useful for the preparation of compounds of formula 4 from 4-aminopyrimidines. The 5-amino group can be introduced using amine formation reactions such as nitration followed by reduction (Dhainant et al. *J. Med. Chem.*, 1996, 39: 4099), arylazo compound formation followed by reduction (Lopez et al. *Nucleosides & Nucleotides*, 1996, 15: 1335), azide formation followed by reduction, or by rearrangement of carboxylic acid derivatives (e.g. Schmidt, Curtius, and Beckmann reactions).

Coupling of aromatic or aliphatic aldehydes, and carboxylic acid derivatives with attached phosphonate esters are particularly suited for the preparation of compounds of formula 1 as described in section 5. Such phosphonate esters are prepared by lithiation of the aromatic ring using methods well described in literature (Gschwend *Org. React.* 1979, 26: 1) followed by addition of phosphorylating agents (e.g. ClPO$_3$R$_2$). Phosphonate esters can also be introduced by Arbuzov-Michaelis reaction (Brill *Chem Rev.*, 1984, 84: 577) and transition metal catalyzed reaction with alkyl halides and aryl halides or triflates (Balthazar et al. *J. Org. Chem.*, 1980, 45: 5425; Petrakis et al. *J. Am. Chem. Soc.*, 1987, 109: 2831; Lu et al. *Synthesis*, 1987, 726). Alternatively, aryl phosphonate esters can be prepared from aryl phosphates under anionic rearrangement conditions (Melvin *Tetrahedron Lett.*, 1981, 22: 3375; Casteel et al. *Synthesis*, 1991, 691). Aryl phosphate esters can also be used to prepare compounds of Formula 1 where X is an oxyaryl group.

N-Alkoxy aryl salts with alkali metal derivatives of dialkyl phosphonate can be used to synthesize heteroaryl-2-phosphonate esters (Redmore *J. Org. Chem.,* 1970, 35: 4114).

A second lithiation step can be used to incorporate the aldehyde functionality, although other methods known to generate aromatic aldehydes can be envisioned as well (e.g. Vilsmeier-Hack reaction, Reimar-Teimann reaction etc.). In the second lithiation step, the lithiated aromatic ring is treated with reagents that either directly generate an aldehyde (e.g. DMF, $HCO_2R$, etc.) or with reagents that lead to a group that subsequently is transformed into an aldehyde group using known chemistry (e.g. alcohol, ester, cyano, alkene, etc.). It is also envisioned that the sequence of these reactions can be reversed, i.e. the aldehyde moiety can be incorporated first followed by the phosphorylation reaction. The order of the reaction will depend on the reaction conditions and the protecting groups. Prior to the phosphorylation, it is also envisioned that it may be advantageous to protect the aldehydes using a number of well-known steps (hemiacetal, hemiaminal, etc.,). The aldehyde is then unmasked after phosphorylation. (*Protective groups in Organic Synthesis, Greene,* T. W., 1991, Wiley, N.Y.).

Formulations

Compounds of the invention are administered orally in a total daily dose of about 0.1 mg/kg/dose to about 100 mg/kg/dose, preferably from about 0.3 mg/kg/dose to about 30 mg/kg/dose. The most preferred dose range is from 0.5 to 10 mg/kg (approximately 1 to 20 nmoles/kg/dose). The use of time-release preparations to control the rate of release of the active ingredient maybe preferred. The dose may be administered in as many divided doses as is convenient. When other methods are used (e.g. intravenous administration), compounds are administered to the affected tissue at a rate from 0.3 to 300 nmol/kg/min, preferably from 3 to 100 nmoles/kg/min. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as, sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 20 to 2000 µmol (approximately 10 to 1000 mg) of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 0.05 to about 50 µmol (approximately 0.025 to 25 mg) of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a fructose 1,6-bisphosphatase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Utility

FBPase inhibitors at the AMP site may be used to treat diabetes mellitus, lower blood glucose levels, and inhibit gluconeogenesis.

FBPase inhibitors at the AMP site may also be used to treat excess glycogen storage diseases. Excessive hepatic glycogen stores are found in patients with some glycogen storage diseases. Since the indirect pathway contributes significantly to glycogen synthesis (Shulman, G. I. *Phys. Rev.* 1992. 72, 1019-1035), inhibition of the indirect pathway (gluconeogenesis flux) is expected to decrease glycogen overproduction.

FBPase inhibitors at the AMP site may also be used to treat or prevent diseases associated with increased insulin levels.

Increased insulin levels are associated with an increased risk of cardiovascular complications and atherosclerosis (Folsom, et al., *Stroke,* 1994, 25, 66-73; Howard, G. et al., *Circulation* 1996, 93, 1809-1817). FBPase inhibitors are expected to decrease postprandial glucose levels by enhancing hepatic glucose uptake. This effect is postulated to occur in individuals that are non-diabetic (or pre-diabetic, i.e. without elevated HGO or fasting blood glucose levels). Increased hepatic glucose uptake will decrease insulin secretion and thereby decrease the risk of diseases or complications that arise from elevated insulin levels.

The compounds of this invention and their preparation can be understood further by the examples which illustrate some of the processes by which these compounds are prepared. These examples should not, however, be construed as specifically limiting the invention and variations of the invention, now known or later developed, are considered to fall within the scope of the present invention as hereinafter claimed.

EXAMPLES

Example 1

Preparation of 5-diethylphosphono-2-furaldehyde (1).

Step A. A solution of 2-furaldehyde diethyl acetal (1 mmol) in THF was treated with nBuLi (1 mmol) at −78° C. After 1 h, diethyl chlorophosphate (1.2 mmol) was added and the reaction was stirred for 40 min. Extraction and evaporation gave a brown oil.

Step B. The resulting brown oil was treated with 80% acetic acid at 90° C. for 4 h. Extraction and chromatography gave compound 1 as a clear yellow oil.

Alternatively This Aldehyde Can Be Prepared From Furan As Described Below.

Step C. A solution of furan (1 mmol) in diethyl ether was, treated with TMEDA (N,N,N'N'-tetramethylethylenediamine) (1 mmol) and nBuLi (2 mmol) at −78° C. The solution was stirred for 0.5 h. at −78° C. and diethyl chlorophosphate was added and stirred for another 1 h. Extraction and distillation produced diethyl 2-furanphosphonate as a clear oil.

Step D. A solution of diethyl 2-furanphosphonate (1 mmol) in THF (tetrahydrofuran) was treated with LDA (1.12 mmol, lithium N,N-diisopropylamide) at −78° C. for 20 min. Methyl formate (1.5 mmol) was added and the reaction was stirred for 1 h. Extraction. and chromatography gave compound 1 as a clear yellow oil.

Preferably this aldehyde can be prepared from 2-furaldehyde as described below.

Step E. A solution of 2-furaldehyde (1 mmol) and N,N'-dimethylethylene diamine (1 mmol) in toluene was refluxed with a Dean-Stark trap to collect the resulting, water. After 2 h the solvent was removed in vacuo and the residue was distilled to give furan-2-(N,N'-dimethylimidazolidine) as a clear colorless oil, bp 59-61° C. (3 mm Hg).

Step F. A solution of furan-2-(N,N'-dimethylimidazolidine) (1 mmol) and TMEDA (1 mmol) in THF was treated with nBuLi (1.3 mmol) at −40 to −48° C. The reaction was stirred at 0° C. for 1.5 h and then cooled to −55° C. and treated with a solution of diethylchlorophosphate (1.1 mmol) in THF. After stirring at 25° C. for 12 h the reaction mixture was evaporated and subjected to extraction to give 5-diethylphosphono-furan-2-(N,N'-dimethylimidazolidine) as a brown oil.

Step G. A solution of 5-diethylphosphonofuran-2-(N,N'-dimethyl-imidazolidine) (1 mmol) in water was treated with concentrated sulfuric acid until pH=1. Extraction and chromatography gave compound 1 as a clear yellow oil.

Example 2

Preparation of $N^9$-substituted-8-(2-(5-phosphono)furanyl)adenines

The preparation of $N^9$-(2-phenethyl)-8-(2-(5-phosphono)furanyl)adenine is given as an example:

Step A. A solution of 5-amino-4,6-dichloropyrimidine (1 mmol) in nBuOH was treated with $Et_3N$ (1.2 mmol) and phenethylamine (1.05 mmol) at 80° C. After 12 h, the cooled reaction mixture was evaporated under vacuum and the residue was chromatographed to give 6-chloro-5-amino-4-(phenethylamino)-pyrimidine as a yellow solid. mp 156-157° C.; TLC: $R_f$=0.41, 50% EtOAc-hexane.

Step B. The 6-chloro-5-amino-4-(2-phenethylamino)pyrimidine (1 mmol) in DMSO was treated with 2-furaldehyde (1.5 mmol) and $FeCl_3$-silica (2.0 mmol) at 80° C. After 12 h, the cooled reaction mixture was filtered and the filtrate was evaporated under vacuum. Chromatography afforded 6-chloro-$N^9$-(2-phenethyl)-8-(2-furanyl)purine as a yellow solid. TLC: Rf=0.62, 50% EtOAc-hexane. Anal. calcd. for $C_{17}H_{13}N_4OCl$: C: 62.87; H: 4.03; N: 17.25. Found: C: 62.66; H: 3.96; N: 17.07.

Step C. The 6-chloro-$N^9$-(2-phenethyl)-8-(2-furanyl)purine (1 mmol) in THF was treated with LDA (1.5 mmol) at −78° C. After 1 h, diethyl chlorophosphate (5 mmol) was added and the reaction was stirred at −78° C. for 2 h and then quenched with saturated $NH_4Cl$. Extraction and chromatography gave 6-chloro-$N^9$-(2-phenethyl)-8-( 2-(5-diethylphosphono)-furanyl)purine as a yellow solid. TLC: Rf=0.34, 100% EtOAc.

Alternatively this type of compound can be prepared as follows:

Step D. A solution of 6-chloro-5-amino-4-(2-phenethylamino)pyrimidine (1 mmol) in DMSO was treated with 5-diethylphosphono-2-furaldehyde (1, 1.5 mmol), and $FeCl_3$-silica (2.0 mmol) at 80° C. After 12 h., the cooled reaction mixture was filtered and the filtrate was evaporated under vacuum. Chromatography afforded 6-chloro-$N^9$-(2-phenethyl)-8-(2-(5-diethyl-phosphono)furanyl)purine as a yellow solid. TLC: Rf=0.34, 100% EtOAc.

Step E. 6-Chloro-$N^9$-(2-phenethyl)-8-(2-(5-diethylphosphono)furanyl)-purine (1 mmol) in THF-DMSO was treated with liquid ammonia (2 mL) in a steel bomb. After 12 h, the reaction was evaporated under vacuum and the residue was purified through chromatography to give $N^9$-(2-phenethyl)-8-(2-(5-diethylphosphono)furanyl)adenine as a yellow solid. TLC: Rf=0.12, 5% MeOH—$CH_2Cl_2$.

Step F. A solution of $N^9$-(2-phenethyl)-8-(2-(5-diethylphosphono)furanyl)-adenine (1 mmol) in acetonitrile was treated with bromotrimethylsilane (10 mmol). After 12 h, the reaction was evaporated under vacuum and the residue was treated with a mixture of water and acetonitrile. The solid was collected through filtration to give $N^9$-(2-phenethyl)-8-(2-(5-phosphono)furanyl)adenine (2.1). mp 242-244° C.; Anal. calcd. for $C_{17}H_{16}N_5O_4P+1.37H_2O$: C: 50.16; H: 4.64; N: 17.21. Found: C: 48.95; H: 4.59; N: 16.80.

The following compounds were prepared according to above procedures:

2.2: $N^9$-(2-cyclohexylethyl)-8-(2-(5-phosphono)furanyl)adenine. mp 194-195° C.; Anal. calcd. for $C_{17}H_{22}N_5O_4P+1 H_2O$: C: 49.90; H: 5.90; N: 17.10. Found: C: 50.20; H: 5.70; N: 17.10.

2.3: $N^9$-(2-naphthylmethyl)-8-(2-(5-phosphono)furanyl)adenine. mp 255-256° C.;
Anal. calcd. for $C_{20}H_{16}N_5O_4P+1 H_2O$: C: 54.70; H: 4.10; N: 15.90. Found: C: 54.30; H: 4.20; N: 15.90.

2.4: $N^9$-(1-(2,2-diphenyl)ethyl)-8-(2-(5-phosphono)furanyl)adenine. mp 220-221° C.; Anal. calcd. for $C_{23}H_{20}N_5O_4P+0.25 H_2O$: C: 59.29; H: 4.43; N: 15.03. Found: C: 59.35; H: 4.25; N: 14.83.

2.5: $N^9$-ethyl-8-(2-(5-phosphono)furanyl)adenine. mp>230° C.; Anal. calcd. for $C_{11}H_{12}N_5O_4P+1 H_2O$: C: 40.38; H: 4.31; N: 21.40. Found: C: 40.45; H: 4.18; N: 21.44.

2.6: $N^9$-isobutyl-8-(2-(5-phosphono)furanyl)adenine. mp>230° C.; Anal. calcd. for $C_{13}H_{16}N_5O_4P$: C: 46.30; H: 4.78; N: 20.76. Found: C: 46.00; H: 4.61; N: 20.49.

2.7: $N^9$-neopentyl-8-(2-(5-phosphono)furanyl)adenine. mp>230° C.; Anal. calcd. for $C_{14}H_{18}N_5O_4P$: C: 47.87; H: 5.16; N: 19.94. Found: C: 47.59; H: 4.92; N: 19.53.

2.8: $N^9$-adamentanemethyl-8-(2-(5-phosphono)furanyl)adenine. mp>250° C.; Anal. calcd. for $C_{20}H_{24}N_5O_4P+0.5 H_2O+0.25 MeOH$: C: 54.48; H: 5.87; N: 15.69. Found: C: 54.62; H: 5.52; N: 15.36.

2.9: $N^9$-cyclopropyl-8-(2-(5-phosphono)furanyl)adenine. mp>250° C.; MS (M+H) calcd for $C_{12}H_{13}N_5O_4P$: 322. found: 322.

2.10: $N^9$-cyclopentyl-8-(2-(5-phosphono)furanyl)adenine. mp 220° C. (decomp); Anal. calcd. for $C_{14}H_{16}N_5O_4P+1 H_2O$: C: 45.78; H: 4.94; N: 19.07. Found: C: 45.40; H: 4.79; N: 18.73.

2.11: $N^9$-((2-ethoxy)phenyl)methyl-8-(2-(5-phosphono)furanyl)-adenine. mp>230° C.; Anal. calcd. for $C_{18}H_{18}N_5O_5P+2 H_2O$: C: 47.90; H: 4.91; N: 15.52. Found: C: 48.03; H: 4.53; N: 15.25.

2.12: $N^9$-(1-(3-N,N-dimethylamino-2,2-dimethyl)propyl)-8-(2-(5-phosphono)-furanyl)adenine. mp>230° C.; Anal. calcd. for $C_{16}H_{23}N_6O_4P+3 H_2O+0.5 HOAc+0.75 Na$: C: 41.19; H: 6.30; N: 16.95. Found: C: 41.35; H: 6.04; N: 16.57.

2.13: $N^9$-(1-(3-hydroxyl-2,2-dimethyl)propyl)-8-(2-(5-phosphono)-furanyl)adenine. mp>230° C.; Anal. calcd. for $C_{14}H_{18}N_5O_5P+0.25 H_2O$: C: 45.23; H: 5.02; N: 18.83. Found: C: 45.40; H: 5.02; N: 18.44.

2.14: $N^9$-(1-(3-chloro-2,2-dimethyl)propyl)-8-(2-(5-phosphono)-furanyl)adenine. mp>230° C.; Anal. calcd. for $C_{14}H_{17}N_5O_4PCl+0.125 CHCl_3+0.06 AcOEt$: C: 42.50; H: 4.37; N: 17.25. Found: C: 42.62; H: 3.99; N: 16.87.

2.15: $N^9$-(1-(3,3-dimethyl)butyl)-8-(2-(5-phosphono)furanyl)-adenine. mp 230° C.; Anal. calcd. for $C_{15}H_{20}N_5O_4P+1.25H_2O+0.13 AcOEt$: C: 46.68; H: 5.94; N: 17.56. Found: C: 46.67; H: 5.78; N: 17.35.

2.16: $N^9$-(1,5,5-trimethyl-3-cyclohexenyl)methyl-8-(2-(5-phosphono)furanyl)-adenine. mp>230° C.; Anal. calcd. for $C_{19}H_{24}N_5O_4P+0.5 H_2O+0.13 AcOEt$: C: 53.54; H: 5.99; N: 16.01. Found: C: 53.67; H: 5.69; N: 15.75.

2.17: $N^9$-(1-(1,2,2-trimethyl)propyl)-8-(2-(5-phosphono)-furanyl)adenine. mp>250° C.; Anal. calcd. for $C_{15}H_{20}N_5O_4P+0.67 H_2O+0.13 AcO Et$: C: 47.74; H: 5.70; N: 18.56. Found: C: 47.99; H: 5.39; N: 18.49.

2.18: 6-Amino-9-(3-(1-imidazolyl)propyl)-8-(2-(5-phosphono)furanyl)purine. mp 182-186° C.; Mass calcd. for $C_{15}H_{16}N_7O_4P$: 389. Found: $M+H^+$=390.

Examples 3

Preparation of $N^9$-substituted-8-(2-phosphonoethylamino)adenines.

Step A. Adenine (1 mmol) in DMF was treated with sodium hydride (1.2 mmol) followed by benzyl bromide (1.2 mmol) at room temperature under nitrogen. The resulting mixture was warmed at 100° C. for 2 h. The cooled reaction mixture was evaporated to dryness. Extraction and chromatography afforded $N^9$-benzyladenine.

Step B. A solution of $N^9$-benzyladenine (1 mmol) in acetic acid buffer (pH=4) was treated with bromine (1 mmol) at room temperature for 12 h. The reaction was quenched with 10% sodium sulfite solution and extracted with dichloromethane. The combined extracts were dried ($Na_2SO_4$) and evaporated to dryness. Chromatography afforded $N^9$-benzyl-8-bromoadenine.

Step C. A mixture of $N^9$-benzyl-8-bromoadenine (1 mmol), aminoethylphosphonate (2 mmol), and sodium hydroxide (2 mmol) in ethanol-water in a sealed tube was warmed at 110° C. under nitrogen. After 24 h the cooled reaction mixture was purified through preparative HPLC to give $N^9$-benzyl-8-(2-phosphonoethylamino)adenine (3.1). Exact mass calculated for $C_{14}H_{17}N_6O_3P+H^+$: 349.1178. Found: 349.1180.

The following compounds were prepared according to this procedure:

3.2: $N^9$-phenethyl-87(2-phosphonoethylamino)adenine. mp 159-160° C.; Anal. calcd. for $C_{15}H_{19}N_6O_3P+1.25 H_2O$: C: 46.81; H: 5.63; N: 21.84. Found: C: 47.05; H: 5.63; N: 21.48.

3.3: $N^9$-(2-naphthylmethyl)-8-(2-phosphonoethylamino)adenine. mp 189-190° C.; Anal. calcd. for $C_{18}H_{19}N_6O_3P+1.5 H_2O$: C: 50.82; H: 5.21; N: 19.76. Found: C: 50.71; H: 5.25; N: 19.54.

3.4: $N^9$-cyclohexylethyl-8-(2-phosphonoethylamino)adenine. mp>250° C.; Anal. calcd. for $C_{15}H_{25}N_6O_3P+0.33 H_2O$: C: 48.12; H: 6.91; N: 22.44. Found: C: 48.12; H: 6.78; N: 22.15.

Example 4

Preparation of 8-(2-phosphonoethylamino)adenosines

A mixture of 8-bromoadenosine (1 mmol), aminoethylphosphonate (2 mmol), and sodium hydroxide (2 mmol) in ethanol-water in a sealed tube was warmed at 110° C. under nitrogen. After 24 h the cooled reaction mixture was purified through preparative HPLC to give 8-(2-phosphonoethylamino)-adenosine (4.1). mp 175° C.;

Anal. calcd. for $C_{12}H_{19}N_6O_7P+0.5 H_2O$: C: 36.10; H: 5.05; N: 21.05; P: 7.76. Found: C: 36.08; H: 4.83; N: 20.36; P: 7.86.

The following compound was prepared in this manner:

4.2: 8-(2-Phosphonoethylamino)-5-deoxyadenosine as a white solid. mp 220° C.;

Anal. calcd. for $C_{12}H_{19}N_6O_6P+1.5 H_2O$: C: 35.92; H: 5.53; N: 20.94. Found: C: 36.15; H: 5.12; N: 20.53.

Examples 5

Preparation of $N^9$-alkyl-8-(phosphonomethoxymethyl)adenines

Step A. A mixture of $N^9$-phenethyl-8-bromoadenine (1 mmol), tetrakis (triphenylphosphine)palladium (0.05 mmol), and triethylamine (5 mmol) in DMF in a sealed tube was warmed at 110° C. under 50 psi of carbon monoxide. After 24 h the cooled reaction mixture was evaporated and purified through chromatography to gave $N^9$-phenethyl-8-methoxycarbonyladenine as a yellow solid. TLC: Rf=0.12, 5% MeOH—$CH_2Cl_2$.

Step B. A solution of $N^9$-phenethyl-8-methoxycarbonyladenine (1 mmol) in tetrahydrofuran was treated with lithium aluminum hydride (1 mmol) at 0° C. for 1 h. Extraction and chromatography gave $N^9$-phenethyl-8-hydroxymethyl-adenine as a white solid. TLC: Rf=0.31, 10% MeOH—$CH_2Cl_2$.

Step C. A solution of $N^9$-phenethyl-8-hydroxymethyladenine (1 mmol) in methylene chloride was treated with phosphorus tribromide (1 mmol) at 25° C. for 1 h. Extraction and chromatography gave $N^9$phenethyl-8-bromomethyl-adenine as a white solid. TLC: $R_f$=0.31, 10% MeOH—$CH_2Cl_2$.

Step D. A solution of $N^9$-phenethyl-8-bromomethyladenine (1 mmol) in DMF was treated with a solution of diethyl hydroxymethylphosphonate sodium salt (1 mmol) in DMF at 25° C. for 1 h. Extraction and chromatography gave $N^9$-phenethyl-8-diethylphosphonomethoxymethyladenine as a white solid. TLC: $R_f$=0.31, 10% MeOH—$CH_2Cl_2$.

$N^9$-phenethyl-8-diethylphosphonomethoxymethyladenine was subjected to Step F in Example 2 to give $N^9$-(2-phenethyl)-8-(phosphonomethoxymethyl)-adenine (5.1) as a white solid. mp>250° C. ; Anal. calcd. for $C_{19}H_{22}N_5O_4P$+0.75 $H_2O$: C: 56.93; H: 5.91; N: 10.48. Found: C: 56.97; H: 5.63; N: 10.28.

The following compounds were prepared according to this procedure:

5.2: $N^9$-(2-cyclohexylethyl)-8-(phosphonomethoxymethyl) adenine. mp>250° C.; Anal. calcd. for $C_{15}H_{24}N_5O_4P$+1 $H_2O$: C: 46.51; H: 6.76; N: 18.08. Found: C: 46.47; H: 6.71; N: 17.91.

5.3: $N^9$-(1-nanonyl)-8-(phosphonomethoxymethyl)adenine. mp 195-210° C.; Anal. calcd. for $C_{16}H_{28}N_5O_4P$+1 $H_2O$: C: 47.64; H: 7.50; N: 17.36. Found: C: 47.33; H: 7.34; N: 16.99.

5.4: $N^9$-(3-cyclohexylpropyl)-8-(phosphonomethoxymethyl)adenine. mp 230-250° C.; Anal. calcd. for $C_{19}H_{22}N_5O_4P$+0.9 $H_2O$+0.3 HBr: C: 45.34; H: 6.68; N: 1,6.52. Found: C: 45.74; H: 6.39; N: 16.18.

Alternatively this type of compound can also be prepared according to the following procedure:

Step E. A solution of 6-chloro-5-amino-4-(neopentylamino)pyrimidine (1 mmol) in diethyl ether was treated with pyridine (3 mmol), and acetoxyacetyl chloride (1.2 mmol) at 25° C. for 12 h. Extraction and chromatography afforded 6-chloro-5-acetoxyacetyl-amino-4-neopentylaminopyrimidine as a yellow solid. TLC: $R_f$=0.18, 30% EtOAc-hexane.

Step F. A solution of 6-chloro-5-acetoxyacetylamino-4-neopentyl-aminopyrimidine (1 mmol) in phosphorus oxychloride was heated at reflux for 6 h. The cooled reaction mixture was evaporated to dryness and the residue was dissolved in pyridine and stirred at 25° C. for 20 h. Evaporation and chromatography afforded 6-chloro-8-acetoxymethyl-$N^9$-neopentylpurine as a yellow solid. TLC: $R_f$=0.51, 50% EtOAc-hexane.

Step G. A solution of 6-chloro-8-acetoxymethyl-$N^9$-neopentylpurine (1 mmol) in THF-water was treated with aqueous sodium hydroxide (1.5 mmol) at 0° C. for 0.5 h. Extraction and chromatography afforded 6-chloro-8-hydroxymethyl-$N^9$-neopentylpurine as a yellow gel. TLC: $R_f$=0.38, 33% EtOAc-hexane.

Step H. A solution of 6-chloro-8-hydroxymethyl-$N^9$-neopentylpurine (1 mmol) in methylene chloride was treated with phosphorus tribromide (1 mmol) at 25° C. for 6 h. Extraction and chromatography afforded 6-chloro-8-bromomethyl-$N^9$-neopentylpurine as a white solid. TLC: $R_f$=0.64, 25% EtOAc-hexane.

Step I. A solution of 6-chloro-8-bromomethyl-$N^9$-neopentylpurine (1 mmol) in DMF was treated with a solution of sodium diethylphosphono-methoxide (1=mmol) at 25° C. for 6 h. Extraction and chromatography afforded 6-chloro-8-diethyl-phosphonomethoxymethyl-$N^9$-neopentylpurine as a white solid. TLC: $R_f$=0.31, 50% EtOAc-hexane.

Step J. A solution of 6-chloro-8-diethylphosphonomethoxymethyl-$N^9$-neopentylpurine (1 mmol) in THF-DMSO was treated with liquid ammonia (10 mmol) at 25° C. for 6 h. Extraction and chromatography afforded 8-diethylphosphonomethoxymethyl-$N^9$-neopentyladenine as a white solid. TLC: $R_f$=0.44, 25% MeOH-EtOAc.

8-Diethylphosphonomethoxymethyl-$N^9$-neopentyladenine was subjected to Step F in Example 2 to give $N^9$-neopentyl-8-(phosphonomethoxymethyl)-adenine (5.5) as a white solid. mp>250° C. ; Anal. calcd. for $C_{12}H_{20}N_5O_4P$+1.5 $H_2O$: C: 40.45; H: 6.51; N: 19.65. Found: C: 40.68; H: 6.35; N: 19.40.

Examples 6

Preparation of $N^9$-substituted-8-(1-(3-phosphono) propyl)adenines

Step A. A mixture of diethyl propargylphosphonate (1 mmol, prepared according to J. Org. Chem., 1993, 58(24), 6531.), tributyltin hydride (1.05 mmol), and AIBN (0.005 mmol) was heated at 60° C. for 18 h. The cooled reaction mixture was purified through chromatography to give dimethyl (1-tributylstannyl)allyl-3-phosphonate as a yellow oil.

Step B. A solution of $N^9$-(2-cyclohexylethyl)-8-bromoadenine (1 mmol), tetrakis(triphenylphosphine)palladium (0.1 mmol), and dimethyl (1-tributylstannyl)allyl-3-phosphonate (5 mmol) in DMF was warmed at 90° C. under nitrogen. After 2 h the cooled reaction mixture was evaporated and purified through chromatography to give $N^9$-(2-cyclohexylethyl)-8-(3-dimethylphosphonopropene-1-yl)adenine as a yellow solid. TLC: $R_f$=0.48, 10% MeOH—$CH_2Cl_2$.

Step C. A solution of $N^9$-(2-cyclohexylethyl)-8-(3-dimethylphosphono-propene-1-yl)adenine in methanol-acetic acid was stirred at room temperature under 50 psi of $H_2$ for 12 h. Filtration and chromatography afforded $N^9$-(2-cyclohexylethyl)-8-(1-(3-dimethylphosphono)propyl)adenine as a yellow solid. TLC: $R_f$=0.26, 10% MeOH—$CH_2Cl_2$.

$N^9$-(2-cyclohexylethyl)-8-(1-(3-dimethylphosphono)propyl)adenine was subjected to Step F in Example 2 to give $N^9$-(2-cyclohexylethyl)-8-(1-(3-phosphono)propyl)adenine (6.1) as a white solid: mp 122-125° C. ; Anal. calcd. for $C_{16}H_{26}N_5O_3P$+0.25 AcOH: C: 51.83; H: 7.12; N: 18.31. Found: C: 51.87; H: 6.96; N: 17.96.

6.2: $N^9$-(2-phenethyl)-8-(1-(3-phosphono)propyl)adenine was also prepared in this manner as a solid. mp>250° C. Anal. calcd. for $C_{16}H_{20}N_5O_3P$+0.5 $H_2O$: C: 51.89; H: 5.71; N: 18.91. Found: C: 51.81; H: 5.49; N: 18.66.

Examples 7

Preparation of $N^9$-(2-phenethyl)-8-(2-(5-phosphono) thienyl)adenine

Step A. A solution of 2-thienyllithium in THF (1 mmol) was added to a solution of diethyl chlorophosphate (1 mmol) at −78° C. under nitrogen. After 2 h the reaction was warmed to room temperature and quenched with brine. Extraction and chromatography afforded 2-diethylphosphonothiophene as a yellow oil. TLC: $R_f$=0.37, 50% EtOAc-hexane.

Step B. A solution of 2-diethylphosphonothiophene (1 mmol) in THF was treated with nBuLi at −78° C. for 1 h. Tributyltin chloride was added and stirred at −78° C. for 2 h and the reaction was quenched with water and warmed to room temperature. Extraction and chromatography afforded diethyl 2-(5-tributylstannyl)thienylphosphonate as a yellow oil. TLC: $R_f$=0.65, 50% EtOAc -hexane.

Step C. A mixture of $N^9$-phenethyl-8-bromoadenine (1 mmol), tetrakis (triphenylphosphine)palladium (0.1 mmol), and diethyl 2-(5-tributylstannyl)-thienylphosphonate (5 mmol) in DMF was warmed at 80° C. under nitrogen. After 21 h the cooled reaction mixture was evaporated to dryness. The dark oil was triturated with hexane and the residue was dissolved in $CH_2Cl_2$ and filtered. The filtrate was evaporated to give $N^9$-(2-phenethyl)-8-(2-(5-diethylphosphono)-thienyl)adenine as a yellow solid. TLC: $R_f$=0.50, 10% MeOH—$CH_2Cl_2$.

$N^9$-(2-phenethyl)-8-(2-(5-diethylphosphono)thienyl)adenine was subjected to Step F in Example 2 to give $N^9$-(2-phenethyl)-8-(2-(5-phosphono)-thienyl)adenine (7.1) as a white solid. mp>250° C.; Anal. calcd. for $C_{17}H_{16}N_5O_3SP$+ $0.5H_2O$: C: 49.76; H: 4.17; N: 17.07. Found: C: 50.07; H: 4.02; N: 17.45.

$N^9$-(2-phenethyl)-8-(2-(5-phosphono)thienyl)adenine can also be made via a cyclization reaction between 5-diethylphosphono-2-thiophene-carboxaldehyde (prepared from 2-thienyllithium as described in Steps C and D of Example 1) as described in Example 2.

Example 8

Preparation of $N^9$-(2-cyclohexylethyl)-8-(phosphonomethylthio)-adenine

Step A. A mixture of $N^9$-(2-cyclohexylethyl)-8-bromoadenine (1 mmol), and $K_2S$ (4 mmol) in ethanol was warmed at 110° C. for 7 h, and at 85° C. for 12 h. The cooled reaction mixture was filtered, evaporated and purified through chromatography to give $N^9$-(2-cyclohexylethyl)-8-thiohydroxyadenine as a yellow solid. TLC: $R_f$=0.26, 5% MeOH—$CH_2Cl_2$.

Step B. A mixture of $N^9$-(2-cyclohexylethyl)-8-thiohydroxyadenine (1 mmol), $K_2CO_3$ (4 mmol), and diethyl chloromethylphosphonate (3 mmol) in DMF was stirred at room temperature for 48 h. Extraction and chromatography gave $N^9$-(2-cyclohexylethyl)-8-diethylphosphono-methylthioadenine. TLC: $R_f$=0.35, 10% MeOH-EtOAc.

$N^9$-(2-Cyclohexylethyl)-8-diethylphosphonomethylthioademine was subjected to Step F in Example 2 to give $N^9$-(2-cyclohexylethyl)-8-(phosphonomethylthio)adenine (8.1) as a white solid. mp 240-243° C.; Anal. Calcd. for $C_{14}H_{22}N_5O_3SP$+$1.25H_2O$: C: 42.69; H: 5.95; N: 17.54. Found: C: 42.62; H: 6.03; N: 17.80.

Example 9

Preparation of 6-chloro-9-phenethyl-8-(2-(5-phosphono)furanyl)purine

6-Chloro-$N^9$-phenethyl-8-(2-(5-diethylphosphono)furanyl)purine (Step C in Example 2) was subjected to procedure of Step F in Example 2 to give compound 9.1 as a yellow solid. mp>200° C.; Anal. calcd. for $C_{17}H_{14}N_4O_4PCl$+2 $H_2O$+0.28 HBr: C: 44.06; H: 3.98; N: 12.09. Found: C: 43.86; H: 3.59; N: 12.02.

Example 10

Preparation of $N^6,N^9$-substituted-8-(2-(5-phosphono)furanyl)adenines

A solution of 6-chloro-$N^9$-substituted-8-(2-(5-diethylphosphono)furanyl)-purine (1 mmol) in DMSO was treated with alkylamine at 100° C. for 12 h. Evaporation and chromatography gave $N^6,N^9$-substituted-8-(2-(5-diethylphosphono)furanyl)adenines.

The title compounds were obtained by subjecting $N^6,N^9$-substituted-8-(2-(5-diethylphosphono)furanyl)adenines to the procedure of Step F in Example 2.

The following compounds were prepared in this manner:

10.1: 6-Dimethylamino-$N^9$-phenethyl-8-(2-(5-phosphono)furanyl)purine as a white solid. mp>200° C.; Anal. calcd. for $C_{19}H_{20}N_5O_4P$: C: 55.2; H: 4.8; N: 16.9. Found: C: 54.9; H: 4.9; N: 16.6.

10.2: 6-Methylamino-$N^9$-phenethyl-8-(2-(5-phosphono)furanyl)purine as a white solid. mp 242° C.; Anal. calcd. for $C_{18}H_{188}N_5O_4P$+1 $H_2O$: C: 51.8; H: 4.8; N: 16.8. Found: C: 51.7; H: 4.8; N: 16.7.

Example 11

Preparation of 2-methylthio-6-amino-$N^9$-isobutyl-8-(2-(5-phosphono)furanyl)purine and 2-methylsulfonyl-6-amino-$N^9$-isobutyl-8-(2-(5-phosphono)furanyl)purine Step A: 2-Methylthio-4,5,6-triaminopyrimidine and 5-diethylphosphono-2-furaldehyde was subjected to the procedures of Step D in Example 2 to give 6-amino-2-methylthio-8-(2-(5-diethylphosphono)furanyl)purine as a yellow solid. TLC: $R_f$=0.27, 80% EtOAc-hexane.

Step B: 6-Amino-2-methylthio-8-(2-(5-diethylphosphono)furanyl)purine was alkylated with isobutyl bromide following the procedures of Step A in Example 3 to give 6-amino-$N^9$-isobutyl-2-methylthio-8-(2-(5-diethylphosphono)-furanyl)purine as a yellow solid. TLC: $R_f$=0.27, 80% EtOAc-hexane.

Step C: 6-Amino-$N^9$-isobutyl-2-methylthio-8-(2-(5-diethyl-phosphono)-furanyl)purine was subjected to Step F in Example 2 to give 6-amino-$N^9$-isobutyl-2-methylthio-8-(2-(5-phosphono)-furanyl)purine (11.1) as a white solid. mp 220° C.; Anal. calcd. for $C_{14}H_{18}N_5O_4PS$+0.25 HBr+0.25 EtOAc: C: 42.33; H: 4.8; N: 16.45. Found: C: 42.42; H: 4.53; N: 16.39.

Step D: A solution of 6-amino-$N^9$-isobutyl-2-methylthio-8-(2-(5-diethyl-phosphono)furanyl)purine (1 mmol) in 50 mL of methanol was cooled to 0° C. and treated with an acetone solution of Oxone (1.6 mmol). After stirring for 3 h at 25° C. the reaction was extracted and then chromatographed to give 6-amino-$N^9$-isobutyl-2-methylsulfonyl-8-(2-(5-diethylphosphono)furanyl)purine as a white solid. TLC: $R_f$=0.24, 100% EtOAc.

Step E: 6-Amino-$N^9$-isobutyl-2-methylsulfonyl-8-(2-(5-diethylphosphono)-furanyl)purine was subjected to Step F in Example 2 to give 6-amino-$N^9$-isobutyl-2-methylsulfonyl-8-(2-(5-phosphono)furanyl)purine (11.2) as a white solid. mp 240° C. (decomp); Anal. calcd. for $C_{14}H_{18}N_5O_6PS$ +0.5 $H_2O$: C: 39.62; H: 4.51; N: 16.5. Found: C: 39.77; H: 4.44; N: 16.12.

Example 12

Preparation of 6-amino-$N^9$-neopentyl-8-(2-(3,4-dichloro-5-phosphono)furanyl)purine Step A: A solution of 3,4-dichloro-2-furoic acid (1 mmol) in diethyl ether was treated with LDA (3 mmol) at −78° C. for 30 min and then treated with diethyl chlorophosphate (3.5 mmol) at −78° C. for 1 h. The reaction was quenched and extracted to give 5-diethylphosphono-3,4-dichloro-2-furoic acid as a yellow foam.

Step B: A solution of 5-diethylphosphono-3,4-dichloro-2-furoic acid (1 mmol) in methylene chloride was treated with oxalyl chloride and DMF at 25° C. for 1 h. The reaction mixture was evaporated and the residue was dissolved in diethyl ether and treated with a solution of 4-chloro-5-amino-6-neopentyl-aminopyrimidine (1 mmol) and pyridine (3 mmol) in diethyl ether at 25° C. for 16 h. Extraction and chromatography gave 4-chloro-5-(2-(3,4-dichloro-5-diethylphosphono)furoyl)amino-6-neopentylaminopyrimidine as a yellow solid. TLC: $R_f$=0.4, 50% EtOAc-hexane.

Step C: A solution of 4-chloro-5-(2-(3,4-dichloro-5-diethylphosphono)-furoyl)amino-6-neopentylaminopyrimidine (1 mmol) in dichloromethane was treated with silicone tetrachloride (2.5 mmol) and triethylamine (2.5 mmol) at 45° C. for 18 h. The cooled reaction mixture was subjected to extraction and chromatography to give 6-chloro-$N^9$-neopentyl-8-(2-(3,4-dichloro-5-diethyl-phosphono)furanyl)purine as a yellow solid. TLC: $R_f$=0.28, 50% EtOAc-hexane.

Step D: 6-Chloro-$N^9$-neopentyl-8-(2-(3,4-dichloro-5-diethylphosphono)-furanyl)purine was subjected to Steps E and F in Example 2 to give 6-amino-$N^9$-neopentyl-8-(2-(3,4-dichloro-5-phosphono)furanyl)purine (12.1) as a white solid. mp>250° C.; Anal. calcd. for $C_{14}H_{16}N_5O_4PCl_2$+0.5 $H_2O$+0.15 EtOAc: C: 39.64; H: 4.15; N: 15.83. Found: C: 39.82; H: 3.88; N: 15.46.

Example 13

Preparation of hydroxyethyldisulfidylethylphosphonate diester

A suspension of 8-(2-(5-phosphono)furanyl)-$N^9$-phenethyladenine (1 mmol) in thionyl chloride (5 mL) was warmed at reflux for 4 h. The cooled reaction mixture was evaporated to dryness and the resulting yellow residue was treated with a solution of 2-hydroxyethyl disulfide (4 mmol), pyridine (2.5 mmol) in methylene chloride. After stirring at 25° C. for 4 h the reaction was subjected to extraction and chromatography to give two compounds:

13.1: $N^9$-phenethyl-8-(bis(6'-hydroxy-3',4'-disulfide)hexylphosphono)furanyl)-adenine. Anal. calcd for $C_{25}H_{32}N_5O_6S_4P$+0.5 DMSO+1.5 $H_2O$: C: 43.15; H: 5.29; N: 9.68. Found: C: 43.38; H: 4.93; N: 9.34.

13.2: $N^9$-phenethyl-8-((3',4'-disulfide)nonacyclic-phosphono)furanyladenine Anal. calcd for $C_{21}H_{22}N_5O_4S_2P$+DMSO: C: 47.49; H: 4.85; N: 12.04. Found: C: 47.93; H: 4.60; N: 11.76.

Example 14

Preparation of substituted benzyl phosphonate diesters

A suspension of 8-(2-(5-phosphono)furanyl)-$N^9$-phenethyladenine (1 mmol) in thionyl chloride (5 mL) was warmed at refluxing 4 h. The cooled reaction mixture was evaporated to dryness and a solution of the resulting yellow residue was added to a solution of the corresponding benzyl alcohol (4 mmol), and pyridine (2.5 mmol) in methylene chloride. After stirring at 25° C. for 4 h the reaction mixture was subjected to extraction and chromatography to give the title compounds.

14.1: $N^9$-phenethyl-8-(2-(5-(bis-(3-bromo-4-methoxy)benzyl)phosphono)-furanyl)adenine. Molecular mass calculated for $C_{33}H_{30}N_5O_6Br_2P$+$H^+$: 784. Found: 784.

14.2: $N^9$-phenethyl-8-(2-(5-(bis-(3-cyano-4-methoxy)benzyl)phosphono)-furanyl)adenine. Anal. calcd. for $C_{35}H_{30}N_7O_6P$+0.5 $H_2O$: C: 61.40; H: 4.56; N: 14.32. Found: C: 61.45; H: 4.51; N: 14.18.

14.3: $N^9$-neopentyl-8-(2-(5-(bis-(4-acetoxy)benzyl) phosphono)furanyl)adenine. Anal. calcd. for $C_{32}H_{34}N_5O_8P$+0.6 $H_2O$: C: 58.37; H: 5.39; N: 10.64. Found: C: 58.11; H: 5.28; N: 10.42.

$N^9$-neopentyl-8-(2-(5-(bis-(3-phthalidyl-2-ethyl) phosphono)furanyl)-adenine is also prepared following the above described procedure using 2-(3-phthalidyl)ethanol which was prepared from phthalide-3-acetic acid in Example 27.

This reaction procedure can also be used to prepare diaryl ester prodrugs of phosphonates, such as substituted phenyl esters of phosphonate.

Example 15

Preparation of 6-amino-8-(2-(5-diphenylphosphono) furanyl)-$N^9$-(2-phenyl)ethylpurine Step A. A suspension of 6-chloro-8-(2-furanyl)-$N^9$-phenethylpurine (1 mmol) in THF at −78° C. was treated with LDA (1.3 mmol) for 1 h. Then a solution of diphenyl chlorophosphate in THF was added and the reaction was stirred at −78° C. for another hour. The reaction was warmed to 0° C. and quenched with aqueous saturated sodium bicarbonate. Extraction and chromatography gave 6-chloro-8-(2-(5-diphenylphosphono)furanyl)-$N^9$phenethylpurine as a white solid. mp 117-118° C.

Step B. A solution of 6-chloro-8-(2-(5-diphenylphosphono)furanyl)-$N^9$-phenethylpurine (1 mmol) in DMF was treated with sodium azide (4 mmol) and triphenylphosphine (4 mmol) at room temperature for 3 h. Filtration, evaporation of the filtrate followed by chromatography gave 6-triphenyl-phosphonoimino-8-(2-(5-diphenylphosphono)furanyl)-$N^9$-(2-phenyl)ethylpurine as a beige foam.

Step C. A solution of 6-triphenylphosphonoimino-8-(2-(5-diphenylphosphono)furanyl)-9-(2-phenyl)ethylpurine (1 mmol) in THF was treated with aqueous hydrogen chloride at room temperature for 24 h. Evaporation and chromatography gave 6-amino-8-(2-(5-diphenylphosphono)furanyl)-$N^9$-(2-phenyl)ethylpurine (15.1) as a pale yellow solid. mp 196-197° C.; Anal. calcd. for $C_{29}H_{24}N_5O_4P$: C: 64.80; H: 4.50; N: 13.03; P: 5.76. Found: C: 64.50; H: 4.47; N: 12.98; P: 5.46.

Example 16

Preparation of acyloxymethylphosphonate diesters

A solution of 8-(2-(5-phosphono)furanyl)-$N^9$-phenethyladenine (1 mmol) in acetonitrile and N,N,N-diisopropylethylamine (5 mmol) was treated with acyloxymethyl iodide (4 mmol) at 0° C. for 24 h. Extraction and chromatography gave the title compounds.

The following compounds were prepared according to this procedure: 16.1: 6-Amino-9-phenethyl-8-(2-(5-diisobutyrylmethylphosphono)furanyl)purine Anal. calcd for $C_{27}H_{32}N_5O_8P$: C: 55.40; H: 5.50; N: 12.00. Found: C: 55.60; H: 5.60; N: 11.80.

16.2: 6-Amino-9-(2-cyclohexylethyl)-8-(2-(5-diisobutyrylmethylphosphono)-furanyl)purine. Anal. calcd for $C_{27}H_{38}N_5O_8P+0.7\ H_2O$: C: 53.70; H: 6.60; N: 11.60. Found: C: 54.00; H: 6.50; N: 11.20.

16.3: 6-Amino-9-ethyl-8-(2-(5-diisobutyrylmethylphosphono)-furanyl)purine. Anal. calcd for $C_{21}H_{28}N_5O_8P$: C: 49.51; H: 5.54; N: 13.75. Found: C: 49.75; H: 5.37; N: 13.76.

16.4: 6-Amino-9-neopentyl-8-(2-(5-diisobutyrylmethylphosphono)furanyl)-purine. Anal. calcd for $C_{24}H_{34}N_5O_8P$: C: 52.27; H: 6.21; N: 12.70. Found: C: 52.40; H: 6.27; N: 12.41.

16.5: 6-Amino-9-neopentyl-8-(2-(5-dipivaloxymethylphosphono)furanyl)purine. Anal. calcd for $C_{26}H_{38}N_5O_8P+0.2\ EtOAc$: C: 53.90; H: 6.68; N: 11.73. Found: C: 54.10; H: 6.80; N: 11.42.

6-Amino-9-phenethyl-8-(2-(5-bis-(3-(5,6,7-trimethoxy)phthalidyl)-phosphono)furanyl)purine (16.6) was also synthesized following this procedure using 3-bromo-5,6,7-trimethoxyphthalide as the alkylating reagent to give the titled compound as a white solid after preparative HPLC purification. mp 155-160° C.; Anal. calcd. for $C_{39}H_{36}N_5O_{14}P+H_2O$: C: 55.26; H: 4.52; N: 8.26. Found: C: 54.89; H: 4.75; N: 8.21.

Example 17

Preparation of 5-methyl-4-hydroxymethyl-2-oxo-13-dioxolene

A solution of 4,5-dimethyl-2-oxo-1,3-dioxolene (1 mmol) and selenium dioxide (2.5 mmol) in dioxane was heated at reflux for 1 h. Evaporation, extraction and. chromatography gave 5-methyl-4-hydroxymethyl-2-oxo-1,3-dioxolene as a yellow oil. TLC: $R_f$=0.5, 5% MeOH-dichloromethane.

Example 18

Preparation of (5-substituted 2-oxo-1,3-dioxolen-4-yl)methyl phosphonate prodrugs A solution of $N^9$-neopentyl-8-(2-(5-phosphono)furanyl)adenine (1 mmol) in DMF and 2 mmol of sodium hydride is treated with 5-methyl-4-bromomethyl-2-oxo-1,3-dioxolene (4 mmol, prepared according to Chem. Pharm. Bull. 1984, 32(6), 2241) at 25° C. for 24 h. Extraction and chromatography gives $N^9$-neopentyl-8-(2-(5-bis(5-methyl-2-oxo-1,3-dioxolen-4-yl)methyl phosphono)-furanyl)adenine.

Alternatively, $N^9$-neopentyl-8-(2-(5-bis(5-methyl-2-oxo-1,3-dioxolen-4-yl)methyl phosphono)-furanyl)adenine is prepared from $N^9$-neopentyl-8-(2-(5-phosphono)furanyl)adenine and 5-methyl-4-hydroxymethyl-2-oxo-1,3-dioxolene (prepared from 4,5-dimethyl-2-oxo-1,3-dioxolene as described in Example 17) according to procedures of Example 14.

Example 19

Preparation of 2-(6-amino-$N^9$-neopentylpurin-8-yl)phenyl phosphonate:

Step A. Triethylamine (1.1 mmol) was added slowly to an ice-cooled solution of. 6-chloro-$N^9$-neopentyl-8-(2-hydroxyphenyl)purine (1 mmol) and diethyl phosphite (1 mmol) in carbontetrachloride. The reaction was stirred at room temperature overnight. Triethylamine hydrochloride was precipitated as a white solid mass. Extraction and chromatography gave diethyl 2-(6-Chloro-$N^9$-neopentylpurin-8-yl) phenyl phosphate.

Step B. Diethyl 2-(6-Chloro-$N^9$-neopentylpurin-8-yl)phenyl phosphate was subjected to Step E and F in Example 2 to give the title compound (19.1). mp>250° C.; Anal. calcd. for $C_{16}H_{20}N_5O_4P+1.25\ H_2O$: C: 48.06; H: 5.67; N: 17.51. Found: C: 48.42; H: 5.42; N: 17.15.

Example 20

Preparation of $N^9$-neopentyl-8-(1-(2-phosphono)imidazolemethyl)adenine

Step A. A solution of 1-benzylimidazole (1.1 mmol) in THF was treated with LDA (1.1 mmol) at −78° C. for 1 h, and followed by addition of diethyl chlorophosphate (2 mmol), and stirred for 2 h. Extraction and chromatography gave 1-benzyl-2-diethylphosphonoimidazole as a yellow oil. TLC: $R_f$=0.35, 80% EtOAc-hexane.

Step B. A solution of 1-benzyl-2-diethylphosphonoimidazole (1 mmol) in EtOH was treated with palladium on carbon (10%) at 25° C. under 1 atmosphere of hydrogen for 19 h. Filtration and evaporation gave 2-diethyl-phosphonoimidazole as a white solid. TLC: $R_f$=0.05, 80% EtOAc-hexane.

Step C. A solution of 8-bromomethyl-6-chloro-$N^9$-neopentylpurine (1 mmol, Step H of Example 5), 2-diethylphosphonoimidazole (2.5 mmol), and N,N,N-diisopropylethylamine (2.5 mmol) in acetonitrile was stirred at 25° C. for 48 h. Extraction and chromatography gave 6-chloro-$N^9$-neopentyl-8-(1-(2-diethylphosphono)imidazolemethyl)purine.

Step D. 6-Chloro-$N^9$-neopentyl-8-(1-(2-diethylphosphono)imidazole-methyl)purine was subjected to Steps E and F in Example 2 to give the title compound (20.1). mp>250° C.; MS (M+H) calcd. for $C_{14}H_{20}N_7O_3P$: 366; found: 366.

Example 21

Preparation of $N^9$-phenethyl-8-(phosphonomethylaminocarbonyl)adenine

Step A. $N^9$-phenethyl-8-(methoxycarbonyl)adenine (1 mmol, prepared as in Step A of Example 5) was treated with sodium hydroxide (1.2 mmol) in THF:MeOH:$H_2O$ (3:2:1) at 25° C. for 1.5 h. The reaction mixture was evaporated to dryness, and the residue was dissolved in DMF, treated with diethyl aminomethylphosphonate (1.5 mmol), EDCl (1-(3-dimethyl-aminopropyl)-3-ethylcarbodiimide hydrochloride, 1.3 mmol), HOBt (1-hydroxy-benzotriazole hydrate, 1.5 mmol), and stirred at 25° C. for 24 h. Extraction and chromatography gave $N^9$-phenethyl-8-(diethylphosphonomethyl-aminocarbonyl)adenine as a white solid. TLC: $R_f$=0.1, EtOAc.

Step B. N⁹-phenethyl-8-(diethylphosphonomethylaminocarbonyl)adenine (1 mmol) was subjected to Step F in Example 2 to give the title compound (21.1). mp>250° C.; Anal. calcd. for $C_{15}H_{17}N_6O_4P+0.17$ Toluene: C: 47.32; H: 4.50; N: 20.45. Found: C: 47.67; H: 4.57; N: 20.78.

Example 22

Preparation of 2-substituted N⁹-neopentyl-8-(2-(5-phosphono)furanyl)adenine

Step A. A solution of 2-amino-4,6-dichloropyrimidine (1 mmol), neopentylamine (1.05 mmol), and triethylamine (2 mmol) in n-butanol was stirred at 110° C. for 12 h. Extraction and chromatography gave 2-amino-4-chloro-6-neopentylpyrimidine as a yellow solid. TLC: $R_f$=0.2, 30% EtOAc-hexane.

Step B. A mixture of 2-amino-4-chloro-6-neopentylpyrimidine (1 mmol), sodium acetate (14 mmol), acetic acid (86 mmol), and 4-chlorobenzene-diazonium hexafluorophosphate (1.15 mmol) in water was stirred at 25° C. for 12 h. Extraction and evaporation gave a yellow solid which was treated with zinc dust (10 mmol) and acetic acid (5.54 mmol) in EtOH-H₂O at 80° C. for 1 h. Extraction and chromatography gave 4-chloro-2,5-diamino-6-neopentylpyrimidine as a yellow solid. TLC: $R_f$=0.25, 50% EtOAc-hexane.

Step C. 4-Chloro-2,5-diamino-6-neopentylpyrimidine was subjected to Step D, E, F in Example 2 to give 2,6-diamino-N⁹-neopentyl-8-(2-(5-phosphono)furanyl)purine (22.1) as a yellow solid. mp 240° C. (decomp); Anal. calcd. for $C_{14}H_{19}N_6O_4P+2.2$ HBr+0.5 acetone: C: 32.47; H: 4.25; N: 14.66. Found: C: 32.31; H: 4.51; N: 14.85.

Similarly, 2-methylthio-N⁹-neopentyl-8-(2-(5-phosphono)furanyl)adenine (22.2) was also prepared from 4-amino-6-chloro-2-methylthiopyrimidine as a yellow solid. mp>250; Anal. calcd. for $C_{15}H_{20}N_5O_4PS+0.2$ $CH_2Cl_2$+0.1 toluene: C: 45.08; H: 5.04; N: 16.53. Found: C: 45.27; H: 5.34; N: 16.24.

Example 23

Preparation of alkyloxycarbonyloxyalkyl phosphonate esters

A solution of N⁹-neopentyl-8-(2-(5-phosphono)furanyl)adenine (1 mmol) in 5 mL of anhydrous DMF is treated with N,N'-dicyclohexyl-4-morpholinecarboxamidine (5 mmol), and isopropyloxycarbonyloxymethyl iodide (5 mmol) which is prepared from the commercially available chloromethyl chloroformate according to the reported procedure, Nishimura et al. *J. Antibiotics,* 1987, 40(1), 81-90. The reaction mixture is stirred for 24 h at room temperature and the solvent is removed under reduced pressure. The resulting syrup is chromatographed on silica with 50%/50% EtOAc/Hexane to yield N⁹-neopentyl-8-(2-(5-diisopropyloxycarbonyloxymethyl phosphono)furanyl)adenine.

Other alkyloxycarbonyloxymethyl, aryloxycarbonyloxymethyl, alkyl- and arylthiocarbonyloxymethyl phosphonate esters can also be prepared following the above described procedure.

Example 24

Preparation of 1-substituted-1,3-propanediol cyclic esters of purine phosphonates Step A. (*J. Org. Chem.,* 1957, 22, 589)
To a solution of 2-pyridine propanol (72.9 mmol) in acetic acid (75 mL) was added 30% hydrogen peroxide slowly. The reaction mixture was heated to 80° C. for 16 h. The reaction was concentrated under vacuum and the residue was dissolved in acetic anhydride (100 mL) and heated at 110° C. overnight. Acetic anhydride was evaporated upon completion of reaction. Chromatography of the mixture by eluting with methanol-methylene chloride (1:9) resulted in 10.5 g of pure 2-(1-(1,3-diacetoxy)propyl)pyridine.

Step B. To a solution of 2-(1-(1,3-diacetoxy)propyl)pyridine (21.1 mmol) in methanol-water (3:1, 40 mL) was added potassium carbonate (105.5 mmol). After stirring for 3 h at room temperature, the reaction mixture was concentrated. The residue was chromatographed by eluting with methanol-methylene chloride (1:9) to give 2.2 g of crystalline 2-(1-(1,3-dihydroxy)propyl)pyridine.

Step C. A suspension of N⁹-neopentyl-8-(2-(5-phosphono)furanyl)adenine (1 mmol) in 5 mL of thionyl chloride was heated at reflux temperature for 4 h. The reaction mixture was cooled and evaporated to dryness. To the resulting residue was added a solution of 2-(1-(1,3-dihydroxy)propyl)pyridine (1 mmol) and pyridine (2.5 mmol) in 3 mL of methylene chloride. After stirring at 25°

C. for 4 h the reaction was subjected to work up and chromatography to give $N^9$-neopentyl-8-(2-(5-(1-(2-pyridyl)propan-1,3-yl)phosphono)furanyl)adenine (24.1) as a sticky solid. Anal. Calcd. for $C_{22}H_{25}N_6O_4P+0.75\ H_2O+1.0$ HCl: C: 50.97; H: 5.35; N: 16.21. Found: C: 51.19, H: 5.02; N: 15.91.

Following the above described procedures, other cyclic esters are also prepared, such as $N^9$-neopentyl-8-(2-(5-(1-(4-pyridyl)propan-1,3-yl)phosphono)furanyl)adenine, $N^9$-neopentyl-8-(2-(5-(1-(3-pyridyl)propan-1,3-yl) phosphono)furanyl)adenine, and $N^9$-neopentyl-8-(2-(5-(1-phenylpropan-1,3-yl)phosphono)furanyl)adenine.

Example 25

Preparation of 2-substituted-1,3-propanediol cyclic esters of purine phosphonates Step A. To a solution of 2-(hydroxymethyl)-1,3-propanediol (1 g, 9.4 mmol) in pyridine (7.5 mL) at 0° C. was added acetic anhydride (0.89 mL, 9.4 mmol) slowly. The resulting solution was warmed to room temperature and stirred for 16 h. The reaction was concentrated under reduced pressure and chromatographed by eluting with methanol-dichloromethane (1:9) to give 510 mg of pure 2-acetoxymethyl-1,3-propanediol.

Step B. 2-Acetoxymethyl-1,3-propanediol was coupled to $N^9$-neopentyl-8-(2-(5-phosphono)furanyl)adenine following Step C of Example 24 to give $N^9$-neopentyl-8-(2-(5-(2-(acetoxymethyl)propan-1,3-yl)phosphono)furanyl)adenine (25.1). mp=164-165° C.; Anal. Calcd. for $C_{20}H_{26}N_5O_6P$: C: 51.84; H: 5.65; N: 15.11. Found: C: 52.12; H: 5.77; N: 14.59.

Following the above described procedures, other cyclic esters are also prepared, such as $N^9$-neopentyl-8-(2-(5-(2-(methoxycarbonyloxymethyl)-propan-1,3-yl)phosphono) furanyl)adenine, $N^9$-neopentyl-8-(2-(5-(2-(hydroxymethyl)-propan-1,3-yl)phosphono)furanyl)adenine, $N^9$-neopentyl-8-(2-(5-(2,2-dihydroxymethylpropan-1,3-yl)phosphono) furanyl)adenine. $N^9$-neopentyl-8-(2-(5-(2-(methoxycarbonyloxymethyl)propan-1,3-yl)phosphono)-furanyl)adenine is prepared by coupling $N^9$-neopentyl-8-(2-(5-phosphono)-furanyl)adenine with 2-(methoxycarbonyloxymethyl)-1,3-propanediol which was prepared as follows:

To a solution of 2-(hydroxymethyl)-1,3-propanediol (9.4 mmol) in dichloromethane (20 mL) and pyridine (7.5 mL) at 0° C. was added methyl chloroformate (9.4 mmol) slowly. The resulting solution was warmed to room temperature and stirred for 16 h. The reaction was concentrated under reduced pressure and chromatographed by eluting with methanol-dichloromethane (1:4) to give 650 mg of 2-(methoxycarbonyloxymethyl)-1,3-propanediol.

Example 26

Preparation of 8-(2-(5-hydroxyl-1,3 cyclohexyl)phosphono)furanylpurines

A suspension of $N^9$-neopentyl-8-(2-(5-phosphono)furanyl)adenine (1 mmol) in 5 mL of thionyl chloride was heated at reflux temperature for 4 h. The reaction mixture was cooled and evaporated to dryness. To the resulting residue was added a solution of cis,cis-1,3,5-cyclohexanetriol (1 mmol) and pyridine (2.5 mmol) in 3 mL of methylene chloride. After stirring at 25° C. for 24 h the reaction was subjected to work up and chromatography to give $N^9$-neopentyl-8-(2-(5-(5-hydroxyl-1,3 cyclohexyl)phosphono)furanyl)adenine, minor isomer (26.1). mp 248-250° C.; Anal. Cald. for $C_{20}H_{26}N_5O_5P+0.5\ H_2O$: C: 52.63; H: 5.96; N: 15.34. Found: C: 52.62; H: 5.70; N: 15.32; major isomer (26.2). mp 225-230° C.; Anal. Cald. for $C_{20}H_{26}N_5O_5P+0.5\ H_2O$: C: 52.63; H: 5.96; N: 15.34. Found: C: 52.74; H: 5.80; N: 15.32.

Following the above described procedures, $N^9$-phenethyl-8-(2-(5-(5-hydroxyl-1,3 cyclohexyl)phosphono)furanyl)adenine (26.3) was also prepared. Anal. Cald. for $C_{23}H_{24}N_5O_5P+0.15\ H_2O$: C: 57.06; H: 5.06; N: 14.47. Found: C: 56.84; H: 4.83; N: 14.38.

Example 27

Preparation of 3-(2-hydroxyethyl)phthalide

A solution of phthalide-3-acetic acid (1 mmol) in THF was treated with borane dimethylsulfide (1.5 mmol) at 0° C. for 1 h, and 25° C. for 24 h. Extraction and chromatography gave 2-(3-phthalidyl)ethanol as a light yellow oil. TLC: $R_f$=0.25, 50 % EtOAc-hexane.

Example 28

Preparation of purine phosphonate amine salts

A mixture of $N^9$-neopentyl-8-(2-(5-phosphono)furanyl) adenine (1 mmol) and tris(hydroxymethyl)aminomethane (1.05 mmol) in methanol is stirred at 25° C. for 24 h. Evaporation give $N^9$-neopentyl-8-(2-(5-phosphono)furanyl) adenine tris(hydroxymethyl)aminomethane salt.

Examples of the methods of the present invention includes the following. It will be understood that these examples are exemplary and that the method of the invention is not limited solely to these examples.

For the purposes of clarity and brevity, chemical compounds in the following biological examples are referred to by synthetic example numbers.

Besides the following Examples, assays that may be useful for identifying compounds which inhibit gluconeogenesis include the following animal models of Diabetes:

i. Animals with pancreatic b-cells destroyed by specific chemical cytotoxins such as Alloxan or Streptozotocin (e.g. the Streptozotocin-treated mouse, -rat, -dog, and -monkey). Kodama, H., Fujita, M., Yamaguchi, I., *Japanese Journal of Pharmacology* 1994, 66, 331-336 (mouse); Youn, J. H., Kim, J. K., Buchanan, T. A., *Diabetes* 1994, 43, 564-571 (rat); Le Marchand, Y., Loten, E. G., Assimacopoulos-Jannet, F., et al., *Diabetes* 1978, 27, 1182-88 (dog); and Pitkin, R. M., Reynolds, W. A., *Diabetes* 1970, 19, 70-85 (monkey).

ii. Mutant mice such as the C57BL/Ks db/db, C57BL/Ks ob/ob, and C57BL/6J ob/ob strains from Jackson Laboratory, Bar Harbor, and others such as Yellow Obese, T-KK, and New Zealand Obese. Coleman, D. L., Hummel, K. P., *Diabetologia* 1967, 3, 238-248 (C57BL/Ks db/db); Coleman, D. L., *Diabetologia* 1978, 14, 141-148 (C57BL/6J ob/ob); Wolff, G. L., Pitot, H. C., *Genetics* 1973, 73, 109-123 (Yellow Obese); Dulin, W. E., Wyse, B. M., *Diabetologia* 1970, 6, 317-323 (T-KK); and Bielschowsky; M., Bielschowsky, F. *Proceedings of the University of Otago Medical School* 1953, 31, 29-31 (New Zealand Obese).

iii. Mutant rats such as the Zucker fa/fa Rat rendered diabetic with Streptozotocin or Dexamethasone, the Zucker Diabetic Fatty Rat, and the Wistar Kyoto Fatty Rat. Stolz, K. J., Martin, R. J. *Journal of Nutrition* 1982, 112, 997-1002

(Streptozotocin); Ogawa, A., Johnson, J. H., Ohnbeda, M., McAllister, C. T., Inman, L., Alam, T., Unger, R. H., *The Journal of Clinical Investigation* 1992, 90, 497-504 (Dexamethasone); Clark, J. B., Palmer, C. J., Shaw, W. N., *Proceedings of the Society for Experimental Biology and Medicine* 1983, 173, 68-75 (Zucker Diabetic Fatty Rat); and Idida, H., Shino, A., Matsuo, T., et al., *Diabetes* 1981, 30, 1045-1050 (Wistar Kyoto Fatty Rat).

iv. Animals with spontaneous diabetes such as the Chinese Hamster, the Guinea Pig, the New Zealand White Rabbit, and non-human primates such as the Rhesus monkey and Squirrel monkey. Gerritsen, G. C., Connel, M. A., Blanks, M. C., *Proceedings of the Nutrition Society* 1981, 40, 237 245 (Chinese Hamster); Lang, C. M., Munger, B. L., *Diabetes* 1976, 25, 434-443 (Guinea Pig); Conaway, H. H., Brown, C. J. Sanders, L. L. etal., *Journal of Heredity* 1980, 71, 179-186 (New Zealand White Rabbit); Hansen, B. C., Bodkin, M. L., *Diabetologia* 1986, 29, 713-719 (Rhesus monkey); and Davidson, I. W., Lang, C. M., Blackwell, W. L., *Diabetes* 1967, 16, 395-401 (Squirrel monkey).

v. Animals with nutritionally induced diabetes such as the Sand Rat, the Spiny Mouse, the Mongolian Gerbil, and the Cohen Sucrose-Induced Diabetic Rat. Schmidt-Nielsen, K., Hainess, H. B., Hackel, D. B., *Science* 1964, 143, 689-690 (Sand Rat); Gonet, A. E., Stauffacher, W., Pictet, R., et al., *Diabetologia* 1965, 1, 162-171 (Spiny Mouse); Boquist, L., *Diabetologia* 1972, 8, 274-282 (Mongolian Gerbil); and Cohen, A. M., Teitebaum, A., Saliternik, R., *Metabolism* 1972, 21, 235-240 (Cohen Sucrose-Induced Diabetic Rat).

vi. Any other animal with one of the following or a combination of the following characteristics resulting from a genetic predisposition, genetic engineering, selective breeding, or chemical or nutritional induction: impaired glucose tolerance, insulin resistance, hyperglycemia, obesity, accelerated gluconeogenesis, increased hepatic glucose output.

Example A

Inhibition of Human Liver FBPase

*E. coli* strain BL21 transformed with a human liver FBPase-encoding plasmid was obtained from Dr. M. R. El-Maghrabi at the State University of New York at Stony Brook. hlFBPase was typically purified from 10 liters of *E. coli* culture as described (M. Gidh-Jain et al., *The Journal of Biological Chemistry* 1994, 269, 27732-27738). Enzymatic activity was measured spectrophotometrically in reactions that coupled the formation of product (fructose 6-phosphate) to the reduction of dimethylthiazoldiphenyltetrazolium bromide (MTT) via NADP and phenazine methosulfate (PMS), using phosphoglucose isomerase and glucose 6-phosphate dehydrogenase as the coupling enzymes. Reaction mixtures (200 µL) were made up in 96-well microtitre plates, and consisted of 50 mM Tris-HCl, pH 7.4, 100 mM KCl, 5 mM EGTA, 2 mM $MgCl_2$, 0.2 mM NADP, 1 mg/mL BSA, 1 mM MTT, 0.6 mM PMS, 1 unit/mL phosphoglucose isomerase, 2 units/mL glucose 6-phosphate dehydrogenase, and 0.150 mM substrate (fructose 1,6-bisphosphate). Inhibitor concentrations were varied from 0.01 ,µM to 10 µM. Reactions were started by the addition of 0.002 units of pure hlFBPase and were monitored for 7 minutes at 590 nm in a Molecular Devices Plate Reader (37° C.).

The following Table depicts the $IC_{50}$ values for several compounds prepared in the Examples. AMP has an $IC_{50}$ value of 1.0 µM in this assay.

Example

| Compound Number | $IC_{50}$ (human liver FBPase |
| --- | --- |
| 2.1 | 5 µM |
| 2.2 | 1.4 µM |
| 2.3 | 3.3 µM |
| 2.7 | 0.8 µM |
| 2.10 | 2 µM |
| 2.13 | 4.5 µM |
| 2.14 | 0.9 µM |
| 2.16 | 1.4 µM |
| 4.1 | 100 µM |
| 5.5 | 10 µM |
| 8.1 | 23 µM |
| 10.1 | 50 µM |
| 11.1 | 0.7 µM |
| 12.1 | 13 µM |

Figure 2:
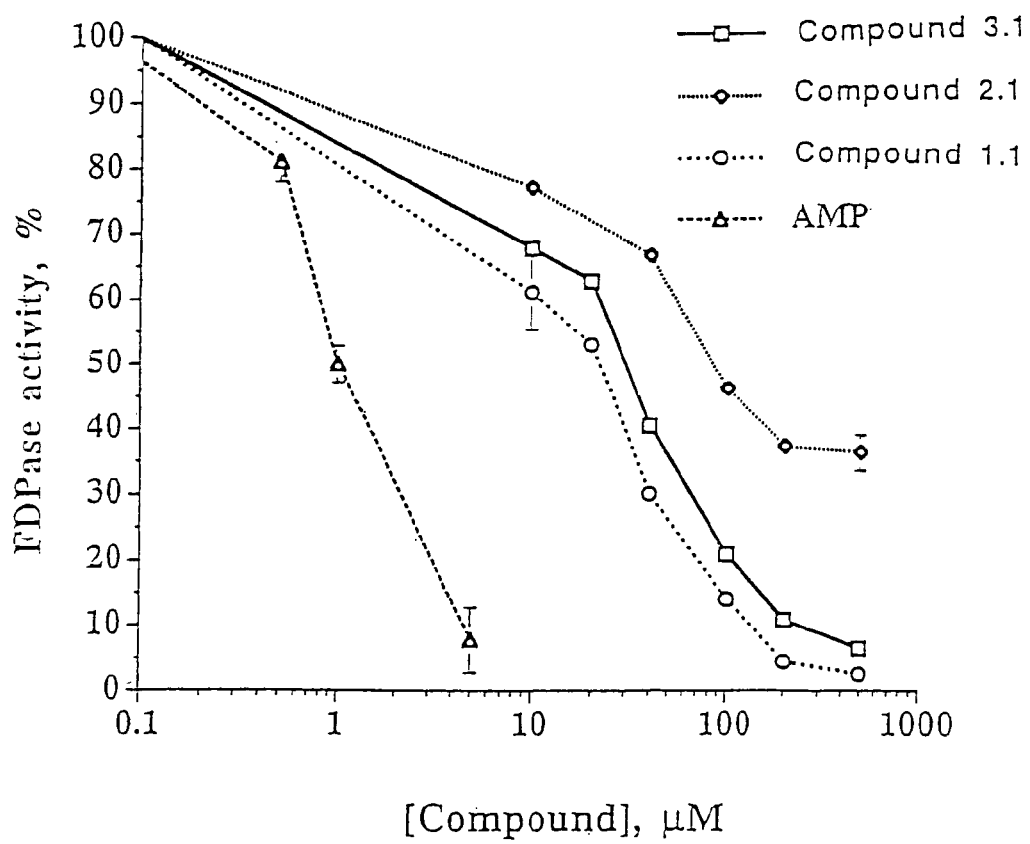
FIG. 2 shows the dose-dependent inhibition of hPFBPase AMP and compounds 2.7, 2.13, and 2.5.

FIG. 2 shows the dose-dependent inhibition of hlFBPase by AMP, compound 2.7, compound 2.13, and compound 2.5.

In Vitro Inhibition of Rat Liver and Mouse Liver FBPase was also Determined.

*E. coli* strain BL21 transformed with a rat liver FBPase-encoding plasmid was obtained from Dr. M. R. El-Maghrabi at the State University of New York at Stony Brook, and purified as described (El-Maghrabi, M. R., and Pilkis, S. J. *Biochem. Biophys. Res. Commun.* 1991, 176, 137-144). Mouse liver FBPase was obtained by homogenizing freshly isolated mouse liver in 100 mM Tris-HCl buffer, pH 7.4, containing 1 mM EGTA, and 10% glycerol. The homogenate was clarified by centrifugation, and the 45-75% ammonium sulfate fraction prepared. This fraction was redissolved in the homogenization buffer and desalted on a PD-10 gel filtration column (Biorad) eluted with same. This partially purified fraction was used for enzyme assays. Both rat liver and mouse liver FBPase were assayed as described for human liver FBPase. Generally, as reflected by the higher $IC_{50}$ values, the rat and mouse liver enzymes are less sensitive to inhibition by the compounds tested than the human liver enzyme.

The following Table depicts the $IC_{50}$ values for several compounds prepared in the Examples:

| Compound | $IC_{50}$ Rat Liver µM | $IC_{50}$ Mouse Liver µM |
| --- | --- | --- |
| 2.1 | 100 | >20 |
| 2.2 | >20 | >20 |
| 2.3 | >20 | >20 |
| 2.7 | 1.25 | 55 |
| 2.10 | >20 | >20 |
| 2.13 | >20 | >20 |
| 2.14 | >20 | >20 |
| 2.16 | >20 | >20 |
| 4.1 | >20 | >20 |
| 5.5 | >20 | >20 |
| 8.1 | >20 | >20 |
| 10.1 | >20 | >20 |
| 11.1 | >20 | >20 |
| 12.1 | 20 | >100 |

Example B

AMP Site Binding

To determine whether compounds bind to the allosteric AMP binding site of hlFBPase, the enzyme was incubated with radiolabeled AMP in the presence of a range of test compound concentrations. The reaction mixtures consisted of 25 mM $^3$H-AMP (54 mCi/mmol) and 0-1000 mM test compound in 25 mM Tris-HCl, pH 7.4, 100 mM KCl and 1 mM MgCl$_2$. 1.45 mg of homogeneous FBPase (±1 nmole) was added last. After a 1 minute incubation, AMP bound to FBPase was separated from unbound AMP by means of a centrifugal ultrafiltration unit ("Ultrafree-MC", Millipore) used according to the instructions of the manufacturer. The radioactivity in aliquots (100 µl) of the upper compartment of the unit (the retentate, which contains enzyme and label) and the lower compartment (the filtrate, which contains unbound label) were quantified using a Beckman liquid scintillation counter. The amount of AMP bound to the enzyme was estimated by comparing the counts in the filtrate (the unbound label) to the total counts in the retentate.

Figure 3:
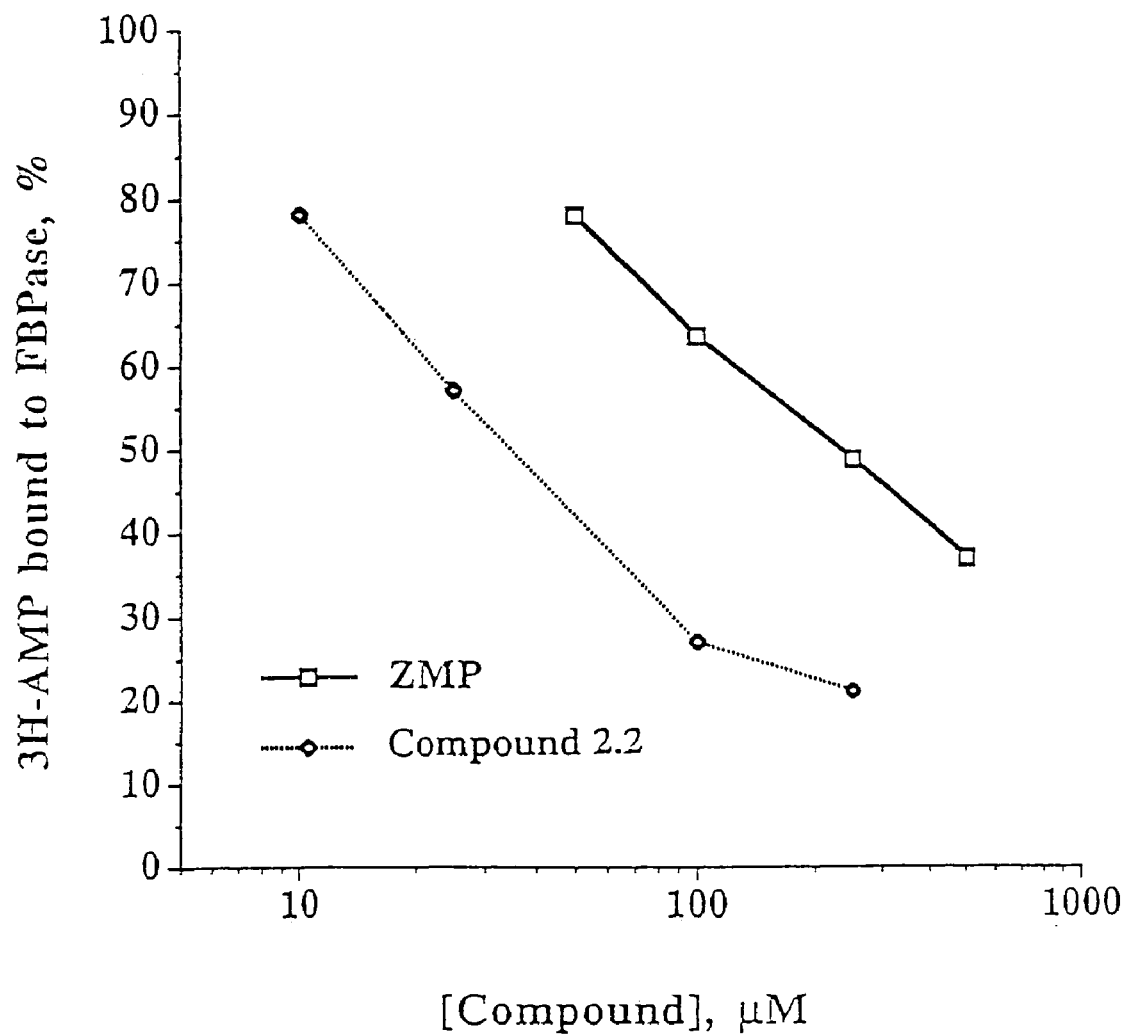
FIG. 3 shows the displacement of $^3$H-AMP from hPFBPase by ZMP and compound 2.2.

As evident from FIG. 3, both aminoimidazolecarboxamideriboside monophosphate (ZMP) and compound 2.2 displaced AMP from hlFBPase in a dose-dependent manner, indicating that they bind to the same site on the enzyme as AMP. As expected, compound 2.2, a more potent hlFBPase inhibitor than ZMP (IC$_{50}$'s=5 and 12 µM, respectively), had a lower ED$_{50}$ for AMP displacement than ZMP (35 vs 250 µM).

Example C

AMP Site/Enzyme Selectivity

To determine the selectivity of compounds towards FBPase, effects of FBPase inhibitors on 5 key AMP binding enzymes were measured using the assays described below:

*Adenosine Kinase*: Human adenosine kinase was purified from an *E. coli* expression system as described by Spychala et al. (Spychala, J., Datta, N. S., Takabayashi, K., Datta, M., Fox, I. H., Gribbin, T., and Mitchell, B. S. *Proc. Natl. Acad. Sci.* USA 1996, 93, 1232-1237). Activity was measured essentially as described by Yamada et al. (Yamada, Y., Goto, H., Ogasawara, N. *Biochim. Biophys. Acta* 1988, 660, 36-43.) with a few minor modifications. Assay mixtures contained 50 mM TRIS-maleate buffer, pH 7.0, 0.1% BSA, 1 mM ATP 1 mM MgCl$_2$, 1.0 µM [U-$^{14}$C] adenosine (400-600 mCi/mmol) and varying duplicate concentrations of inhibitor. $^{14}$C-AMP was separated from unreacted $^{14}$C-adenosine by absorption to anion exchange paper (Whatman) and quantified by scintillation counting.

*Adenosine Monophosphate Deaminase*: Porcine heart AMPDA was purified essentially as described by Smiley et al. (Smiley, K. L., Jr, Berry, A. J., and Suelter, C. H. *J. Biol. Chem.* 1967, 242, 2502-2506) through the phosphocellulose step. Inhibition of AMPDA activity was determined at 37° C. in a 0.1 mL assay mixture containing inhibitor, ~0.005U AMPDA, 0.1% bovine serum albumin, 10 mM ATP, 250 mM KCl, and 50 mM MOPS at pH 6.5. The concentration of the substrate AMP was varied from 0.125-10.0 mM. Catalysis was initiated by the addition of enzyme to the otherwise complete reaction mixture, and terminated after 5 minutes by injection into an HPLC system. Activities were determined from the amount of IMP formed during 5 minutes. IMP was separated from AMP by HPLC using a Beckman Ultrasil-SAX anion exchange column (4.6 mm×25 cm) with an isocratic buffer system (12.5 mM potassium phosphate, 30 mM KCl, pH 3.5) and detected spectrophotometrically by absorbance at 254 nm.

*Phosphofructokinase*: Enzyme (rabbit liver) was purchased from Sigma. Activity was measured at 30° C. in reactions in which the formation of fructose 1,6-bisphosphate was coupled to the oxidation of NADH via the action of aldolase, triosephosphate isomerase, and (α-glycerophosphate dehydrogenase. Reaction mixtures (200 µl) were made up in 96-well microtitre plates and were read at 340 nm in a Molecular Devices Microplate Reader. The mixtures consisted of 200 mM Tris-HCl pH 7.0, 2 mM DTT, 2 mM MgCl2, 0.2 mM NADH, 0.2 mM ATP, 0.5 mM Fructose 6-phosphate, 1 unit aldolase/mL, 3 units/mL triosephosphate isomerase, and 4 units/mL α-glycerophosphate dehydrogenase. Test compound concentrations ranged from 1 to 500 µM. Reactions were started by the addition of 0.0025 units of phosphofructokinase and were monitored for 15 minutes

*Glycogen Phosphorylase*: Enzyme (rabbit muscle) was purchased from Sigma. Activity was measured at 37° C. in reactions in which the formation of glucose 1-phosphate was coupled to the reduction of NADP via phosphoglucomutase and glucose 6-phosphate dehydrogenase. Assays were performed on 96-well microtitre plates and were read at 340 nm on a Molecular Devices Microplate Reader. Reaction mixtures consisted of 20 mM imidazole, pH 7.4, 20 mM MgCl$_2$, 150 mM potassium acetate, 5 mM potassium phosphate, 1 mM DTT, 1 mg/mL BSA, 0.1 mM NADP, 1 unit/mL phosphoglucomutase, 1 unit/mL glucose 6-phosphate dehydrogenase, 0.5% glycogen. Test compound concentrations ranged from 1 to, 500 µM. Reactions were started by the addition of 17 µg enzyme and were monitored for 20 minutes.

*Adenylate Kinase*: Enzyme (rabbit muscle) was purchased from Sigma. Activity was measured at 37° C. in reaction mixtures (100 µl) containing 100 mM Hepes, pH 7.4, 45 mM MgCl$_2$, 1 mM EGTA, 100 mM KCl, 2 mg/mL BSA, 1 mM AMP and 2 mM ATP. Reactions were started by addition of 4.4 ng enzyme and terminated after 5 minutes by addition of 17 µl perchloric acid. Precipitated protein was removed by centrifugation and the supernatant neutralized by addition of 33 µl 3 M KOH/3 M KH$_2$CO$_3$. The neutralized solution was clarified by centrifugation and filtration and analyzed for ADP content (enzyme activity) by HPLC using a YMC ODS AQ column (25×4.6 cm). A gradient was run from 0.1 M KH$_2$PO$_4$, pH 6, 8 mM tetrabutyl ammonium hydrogen sulfate to 75% acetonitrile. Absorbance was monitored at 254 nM.

Compound 2.1, a 5 µM hlFBPase inhibitor, was essentially inactive in all of the above described assays except for the AMP deaminase screen: half-maximal inhibition of AMP deaminase was observed at almost the same concentration as the IC$_{50}$ for FBPase. Compound 2.7 (hlFBPase IC$_{50}$=0.8 µM), in addition to being essentially without effect on adenosine kinase, adenylate kinase, glycogen phosphorylase, and phosphofructokinase, was only a weak inhibitor of AMP deaminase (IC$_{50}$=390 µM). The data suggest that compound 2.7 binds to hlFBPase in a highly selective manner. The following Table gives the selectivity data for compounds 2.1 and 2.7.

| SELECTIVITY | | |
| --- | --- | --- |
|  | Compound 2.1 | Compound 2.7 |
| FBPase (inh.) | 5.0 μM | 0.8 μM |
| Adenosine Kinase (inh.) | >>10 | >>100 |
| Adenylate Kinase (inh.) | >>500 | >>500 |
| AMP Deaminase (inh.) | 6.7 | 390 |
| Glycogen Phosphorylase (act.) | >>250 | >>100 |
| Phosphofructokinase (act.) | >>200 | >>100 |

Example D

Inhibition of Gluconeogenesis in Rat Hepatocytes

Hepatocytes were prepared from overnight fasted Sprague-Dawley rats (250-300 g) according to the procedure of Berry and Friend (Berry, M. N., Friend, D. S., *J. Cell. Biol.* 1969, 43, 506-520) as modified by Groen (Groen, A. K., Sips, H. J., Vervoorn, R. C., Tager, J. M., *Eur. J. Biochem.* 1982, 122, 87-93). Hepatocytes (75 mg wet weight/mL) were incubated in 1 mL Krebs-bicarbonate buffer containing 10 mM Lactate, 1 mM pyruvate, 1 mg/mL BSA, and test compound concentrations from 1 to 500 μM. Incubations were carried out in a 95% oxygen, 5% carbon dioxide atmosphere in closed, 50-mL Falcon tubes submerged in a rapidly shaking water bath (37° C.). After 1 hour, an aliquot (0.25 mL) was removed, transferred to an Eppendorf tube and centrifuged. 50 μl of supernatant was then assayed for glucose content using a Sigma Glucose Oxidase kit as per the manufacturer's instructions.

Figure 5:
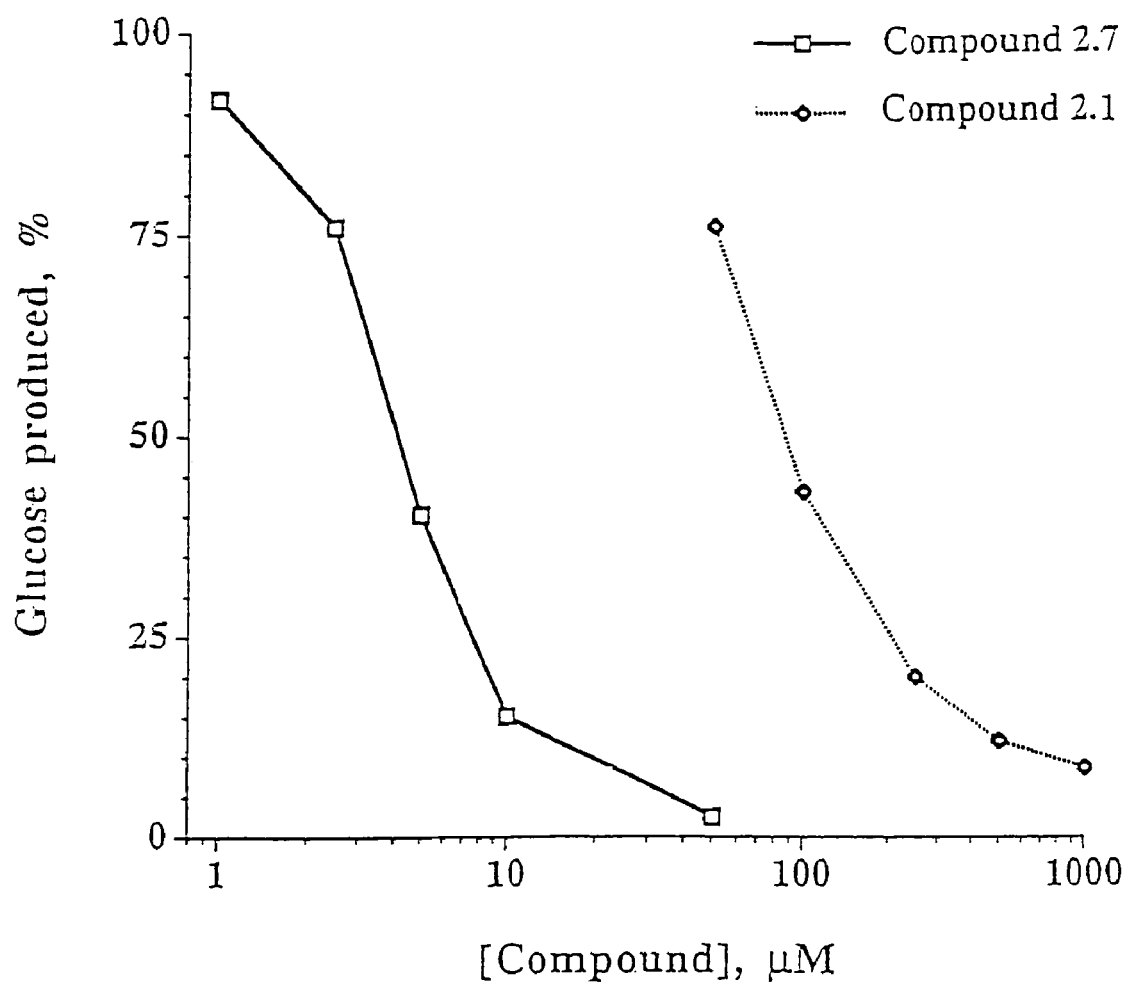
FIG. 5 depicts a dose-dependent inhibition of glucose production in rat hepatocytes exposed to lactate and pyruvate by compounds 2.7 and 2.1.

Compound 2.1 and compound 2.7 inhibited glucose production from lactate/pyruvate in isolated rat hepatocytes in a dose-dependent manner, with $IC_{50}$'s of 90 and 4.5 μM, respectively (FIG. 5). $IC_{50}$'s for other select compounds in this assay are shown in the Table below:

| Compound | $IC_{50}$ Glucose Production, μM |
| --- | --- |
| 2.2 | 90 |
| 2.6 | 18 |
| 2.10 | 24 |
| 2.13 | 50 |
| 2.14 | 7.5 |
| 2.16 | 12 |
| 16.4 | 3 |

FPBase from rat liver is less sensitive to AMP than that from human liver. $IC_{50}$ values are correspondingly higher in rat hepatocytes than would be expected in human hepatocytes.

Example E

Effect of Compound 2.7 on Gluconeogenesis from Dihydroxyacetone in Rat Hepatocytes: Glucose Production Inhibition and Fructose 1,6-bisphosphate Accumulation Isolated rat hepatocytes were prepared as described in Example D and incubated under the identical conditions described except that lactate/pyruvate was replaced by 10 mM dihydroxyacetone, a substrate which feeds into the gluconeogenic pathway at a step just prior to FBPase. Reactions were terminated by removing an aliquot (250 μL) of cell suspension and spinning it through a layer of oil (0.8 mL silicone/mineral oil, 4/1) into a 10% perchloric acid layer (100 μL). After removal of the oil layer, the acidic cell extract layer was neutralized by addition of ⅓rd volume of 3 M KOH/3 M $KH_2CO_3$. After thorough mixing and centrifugation, the supernatant was analyzed for glucose content as described in Example D, and also for fructose-1,6-bisphosphate. Fructose-1,6-bisphosphate was assayed spectrophotometrically by coupling its enzymatic conversion to glycerol 3-phosphate to the oxidation of NADH, which was monitored at 340 nm. Reaction mixtures (1 mL) consisted of 200 mM Tris-HCl, pH 7.4, 0.3 mM NADH, 2 units/mL glycerol 3-phosphate dehydrogenase, 2 units/mL triosephosphate isomerase, and 50-100 μl cell extract. After a 30 minute preincubation at 37° C., 1 unit/mL of aldolase was added and the change in absorbance measured until a stable value was obtained. 2 moles of NADH are oxidized in this reaction per mole of fructose-1,6-bisphosphate present in the cell extract.

Figure 4A:
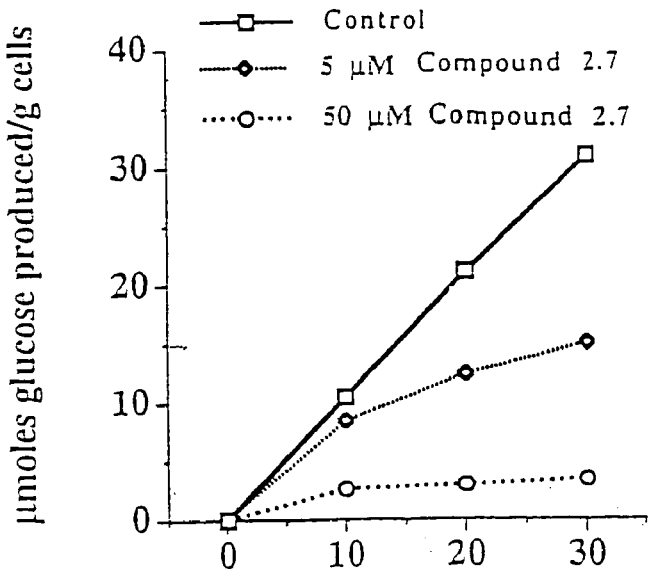
FIG. 4A depicts the reduction of glucose production from dihydroxyacetone in rat hepatocytes treated with compound 2.7.
Figure 4B:
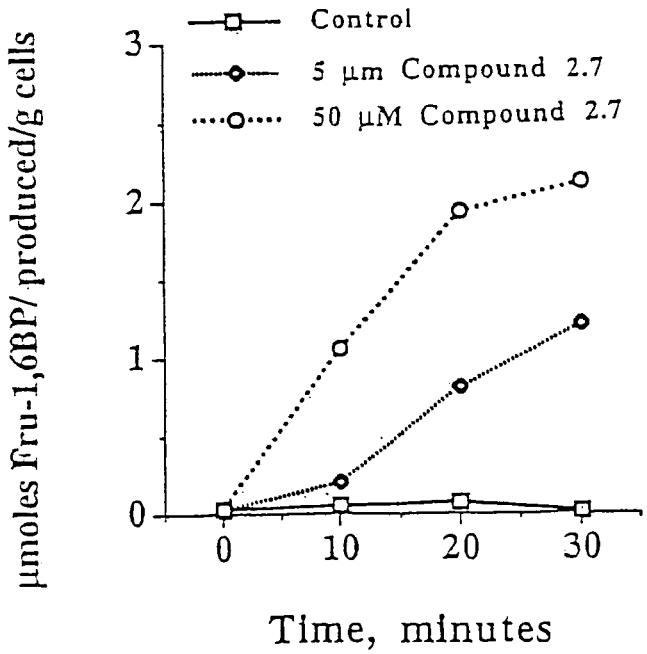
FIG. 4B depicts the increase in the amount of fructose-1,6-bisphosphate in rat hepatocytes exposed to dihydroxyacetone and treated with compound 2.7.

As shown in FIG. 4A, compound 2.7 inhibited glucose production from dihydroxyacetone in rat hepatocytes ($IC_{50}$ approx. 5 μM) as effectively as from lactate pyruvate ($IC_{50}$ 4.5 μM, FIG. 5). This data confirms that the site of action of the compound is in the last four steps of the gluconeogenic pathway. The dose-dependent accumulation of fructose-1,6-bisphosphate (the substrate of FBPase) that occurs upon cell exposure to compound 2.7 (FIG. 4B) is consistent with the inhibition of FBPase, the second to last enzyme in the pathway.

Example F

Blood Glucose Lowering in Fasted Rats

Sprague Dawley rats (250-300 g) were fasted for 18 hours and then dosed intraperitoneally either with saline or with 35, 45, and 60 mg/kg compound 16.4, a prodrug of compound 2.7. The vehicle used for drug administration was dimethylsulfoxide. Blood samples were obtained from the tail vein of conscious animals just prior to injection and then at half-hourly intervals. Blood glucose was measured using a HemoCue Inc. glucose analyzer according to the instructions of the manufacturer.

Figure 6:
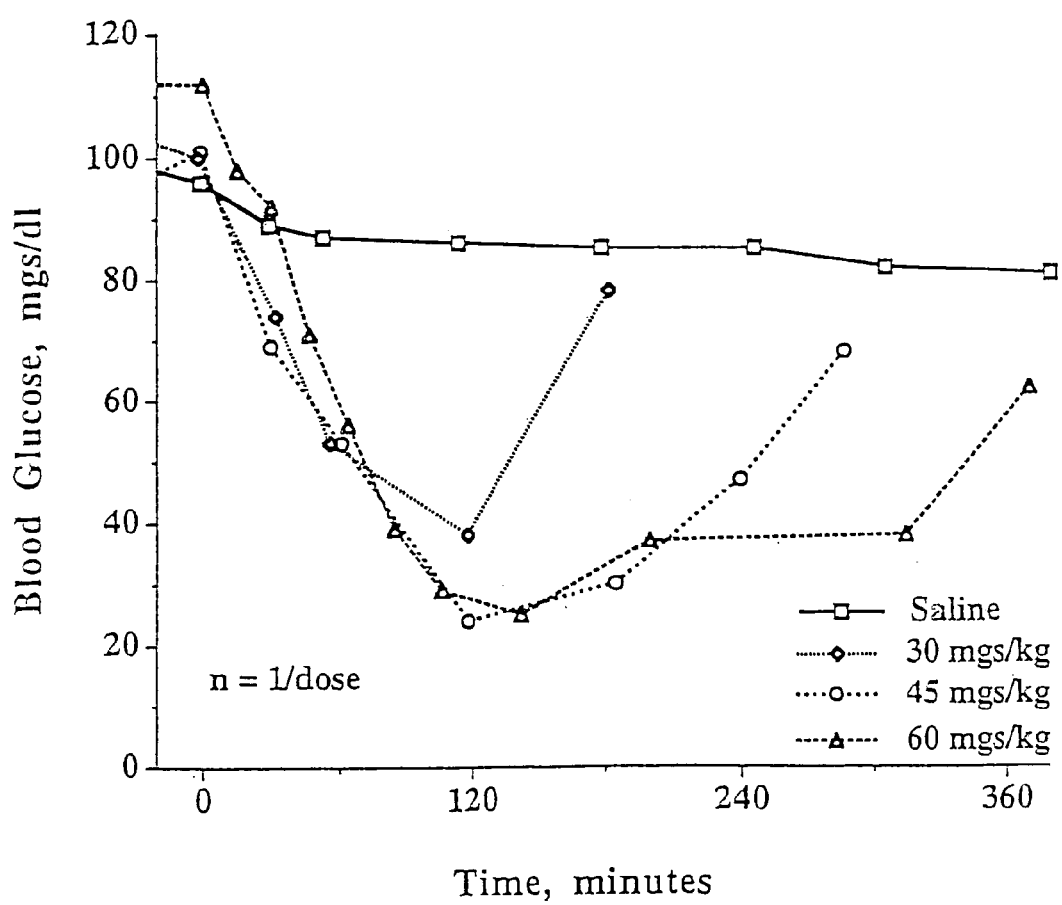
FIG. 6 shows the effect of various doses of compound 16.4 on blood glucose levels in 18 hour fasted, normal rats.

FIG. 6 shows the profound glucose lowering elicited by treatment with compound 16.4. The duration of action was dose-dependent and ranged from 2 to 6 hours.

Example G

Analysis of Drug Levels and Liver Fructose-1,6-bisphosphate Accumulation In Rats Sprague-Dawley rats (250-300 g) were fasted for 18 hours and then dosed intraperitoneally either with saline (n=3) or 20 mgs/kg compound 2.7 (n=4). The vehicle used for drug administration was 10 mM bicarbonate. One hour post injection rats were anesthetized with halothane and a liver biopsy (approx. 1 g) was taken as well as a blood sample (2 mL) from the posterior vena cava. A heparin flushed syringe and needle were used for blood collection. The liver sample was immediately homogenized in ice-cold 10% perchloric acid (3 mL), centrifuged, and the supernatant neutralized with ⅓rd volume of 3 M KOH/3 M $KH_2CO_3$. Following centrifugation and filtration, 50 μL of the neutralized extract was analyzed for compound 2.7 content by HPLC. A reverse phase YMC ODS AQ column (250×4.6 cm) was used and eluted with a gradient from 10 mM sodium phosphate pH 5.5 to 75% acetonitrile. Absorbance was monitored at 310 nm. The concentration of fructose-1,6-bisphosphate in liver was also quantified using the method described in Example E. Blood glucose was measured in the blood sample as described in Example F. Plasma was then quickly prepared by centrifugation and extracted by addition of methanol to 60% (v/v). The methanolic extract was clarified by centrifugation and filtration and then analyzed by HPLC as described above.

Figure 7:
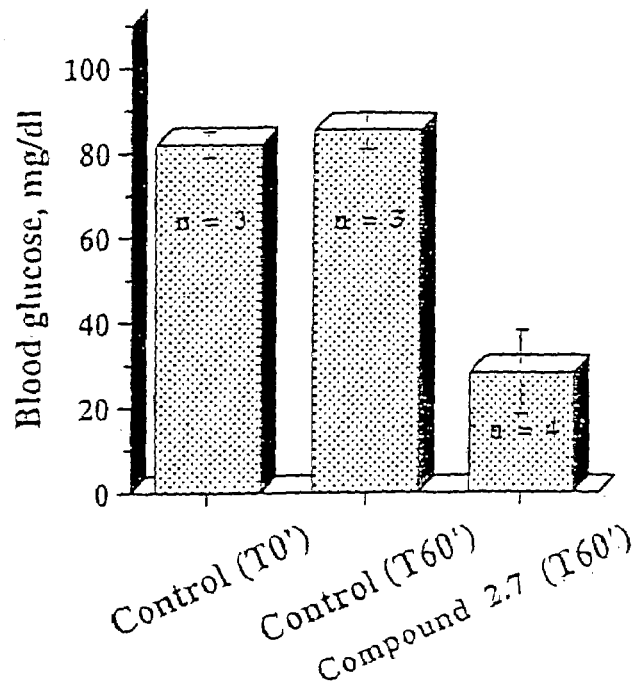
FIG. 7 is a bar graph depicting the reduction in blood glucose levels in 18 hour fasted normal rats treated with compound 2.7 given at a dose of 20 mg/kg i.p.
Figure 8:
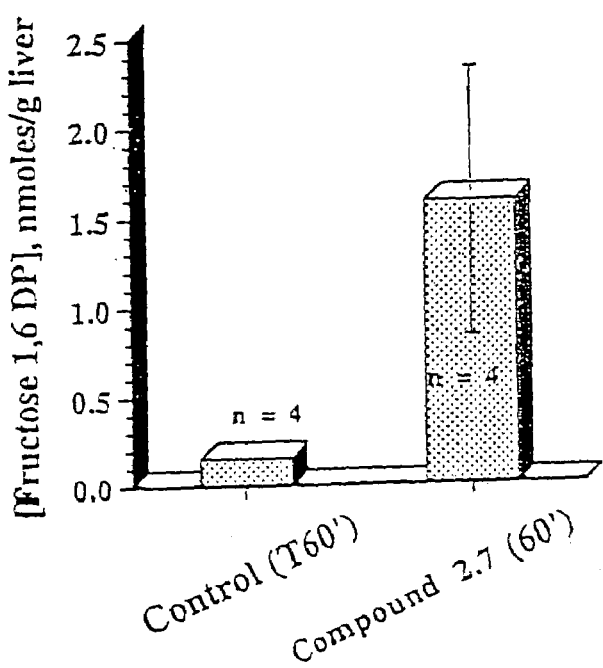
FIG. 8 is a bar graph depicting the increased accumulation of fructose-1,6-bisphosphate in the liver of 18-hour fasted rats treated with compound 2.7.

Compound 2.7 lowered blood glucose from 82±3 to 28±9.9 mg/dL within one hour (FIG. 7). Drug levels measured in plasma and liver were 38.5±7 μM and 51.3±10 nmoles/g, respectively. As shown in FIG. 8, a 10-fold elevation of fructose-1,6-bisphosphate levels was found in the livers from the drug-treated group, consistent with the inhibition of glucose production at the level of FBPase in the gluconeogenic pathway.

Example H

Blood Glucose Lowering in Zucker Diabetic Fatty Rats

Zucker Diabetic Fatty rats purchased at 7 weeks of age were used at age 16 weeks in the 24-hour fasted state. The rats were purchased from Genetics Models Inc. and fed the recommended Purina 5008 diet (6.5% fat). Their fasting hyperglycemia at 24 hours ranged from 150 mg/dL to 310 mg/dL blood glucose.

Compound 2.7 was administered at a dose of 50 mg/kg by intraperitoneal injection (n=6). The stock solution was made up at 25 mg/L in deionized water and adjusted to neutrality by dropwise, addition of 5 N NaOH. 5 control animals were dosed with saline. Blood glucose was measured at the time of dosing and 2 hours post dose as described in Example F.

Figure 9A:
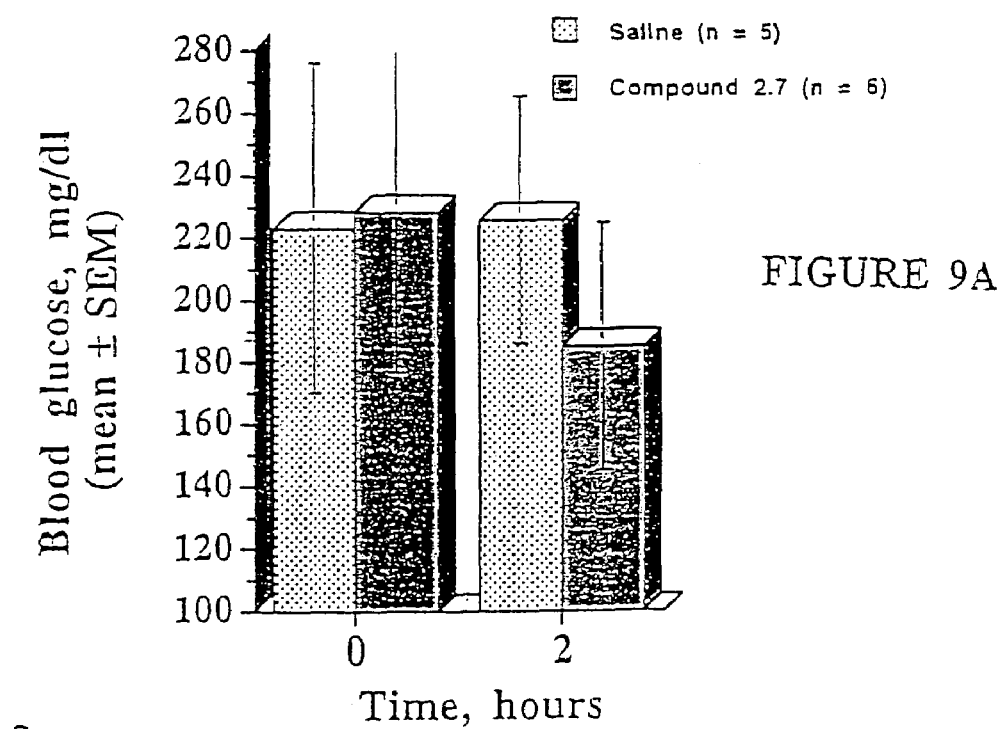
FIG. 9A is a bar graph depicting a reduction in blood glucose levels in 24 hour fasted Zucker Diabetic Fatty rats treated with compound 2.7.
Figure 9B:
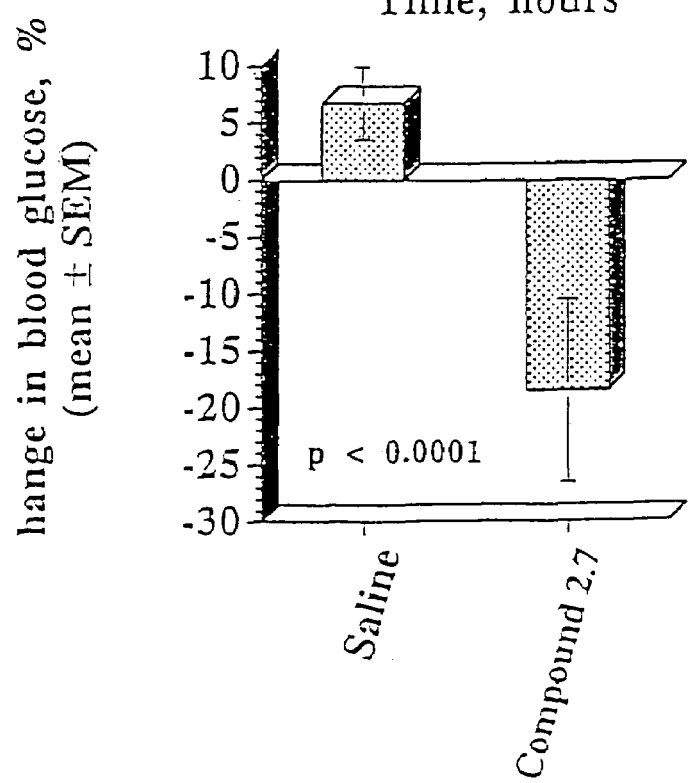
FIG. 9B is a bar graph depicting the percentage change in blood glucose levels in 24 hour fasted Zucker Diabetic Fatty rats treated with compound 2.7.

As shown in FIGS. 9A and 9B, blood glucose was lowered in the drug-treated group by an average of almost 20% (p<0.0001 relative to the control animals).

Example I

Inhibition of Gluconeogenesis in Zucker Diabetic Fatty Rats

Three 20-week old Zucker Diabetic Fatty rats were dosed with compound 2.7 and three with saline as described in Example H. Fifteen minutes post-injection, the animals were anesthetized with sodium pentobarbitol (30 mgs, i.p.) and $^{14}C$-bicarbonate (20 μCi/100 g of body weight) was administered via the tail vein. Blood samples (0.6 mL) were obtained by cardiac puncture 10 and 20 minutes post tracer injection. Blood (0.5 mL) was diluted into 6 mL deionized water and protein precipitated by addition of 1 mL zinc sulfate (0.3 N) and 1 mL barium hydroxide (0.3 N). The mixture was centrifuged (20 minutes, 1000×g) and 5 mL of the resulting supernatant was then combined with 1 g of a mixed bed ion exchange resin (1 part AG 50W-X8, 100-200 mesh, hydrogen form and 2 parts of AG 1-X8, 100-200 mesh, acetate form) to separate $^{14}C$-bicarbonate from $^{14}C$-glucose. The slurry was shaken at room temperature for four hours and then allowed to settle. An aliquot of the supernatant (0.5 mL) was then counted in 5 mL scintillation cocktail.

Figure 10:
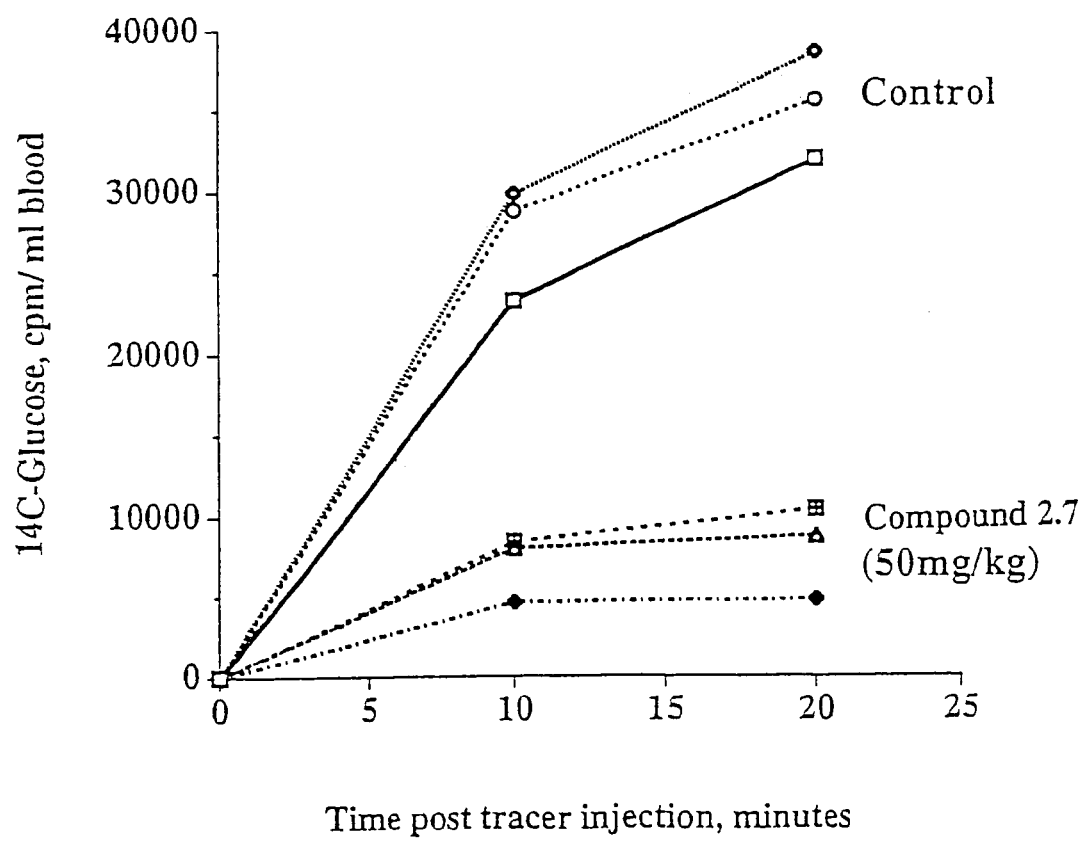
FIG. 10 depicts the inhibition of gluconeogenesis from $^4$C-bicarbonate in 24 hour fasted Diabetic Fatty rats treated with compound 2.7.

As shown in FIG. 10, compound 2.7 reduced the incorporation of $^{14}C$-bicarbonate into glucose by 75%; therefore gluconeogenesis was clearly inhibited by the drug.

Example J

Blood Glucose Lowering in Streptozotocin-treated Rats

Diabetes is induced in male Sprague-Dawley rats (250-300 g) by intraperitoneal injection of 55 mg/kg streptozotocin (Sigma Chemical Co.). Six days later, 24 animals are selected with fed blood glucose values (8 am) between 350 and 600 mg/dL and divided into two statistically equivalent groups. Blood glucose is measured in blood obtained from a tail vein nick by means of a HemoCue Inc. (Mission Viejo, Calif.) glucose analyzer. One group of 12 will subsequently receive inhibitor (100 mg/kg intraperitoneally) and the other 12 ("controls") an equivalent volume of saline. Food is removed from the animals. Blood glucose is measured in each animal four hours after dosing, and a second dose of drug or saline is then administered. Four hours later, a final blood glucose measurement is made.

Example K

Evaluation of Compound 16.4 as a Prodrug in Rat Hepatocytes—Intracellular Delivery of Compound 2.7

Figures 11A, 11B:
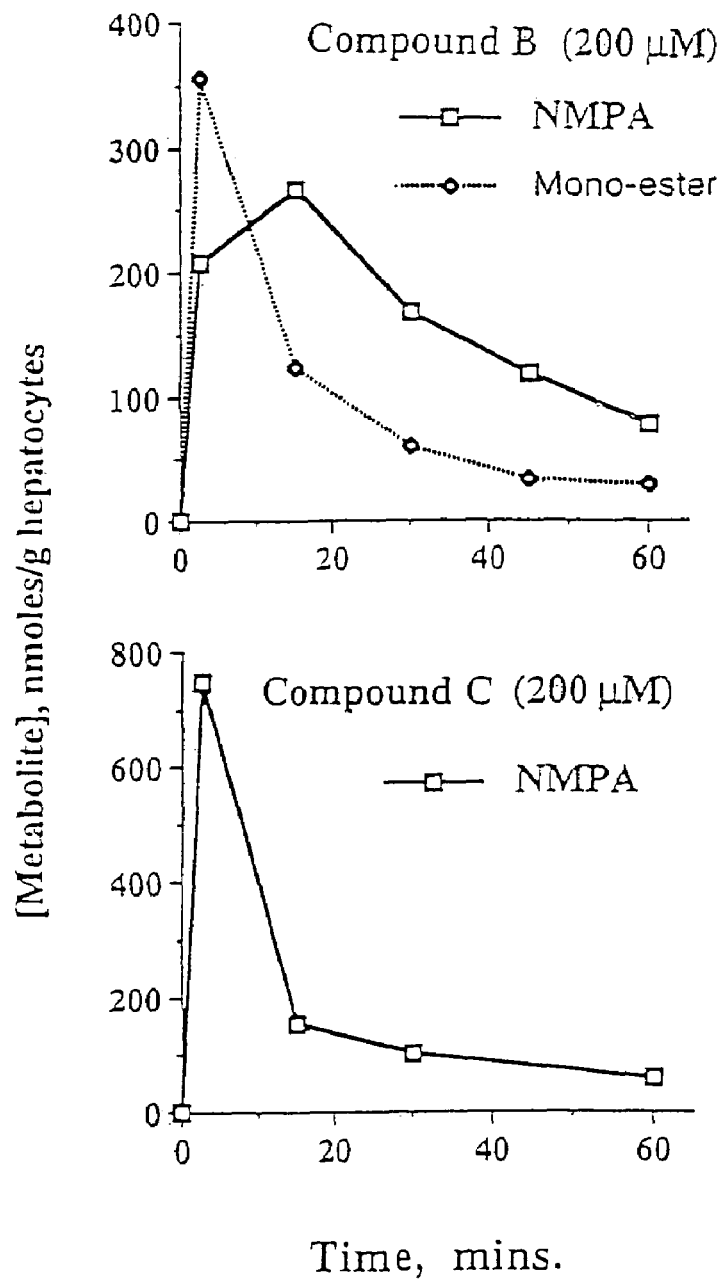
FIG. 11A depicts the dose-dependent inhibition of glucose production in rat hepatocytes by compound 16.4, a prodrug of compound 2.7.
FIG. 11B shows the intracellular generation of compound 2.7 in rat hepatocytes treated with compound 16.4, a prodrug, to inhibit glucose production in rat hepatocytes.

Rat hepatocytes were prepared and incubated as in Example D, except that the test compound, 16.4, was added to yield a final concentration of 10 μM. Aliquots of the cell suspension were taken at 0, 5, 10, 20, 30, 45, and 60 minutes after drug exposure. The cells were extracted and analyzed for compound 2.7 content by HPLC as described in Example L. Absorbance of the HPLC column eluate was monitored at 310 nm. Quantitation of intracellular compound 2.7 was done by comparison to authentic standards of known concentration. As shown in FIG. 11A, compound 16.4 rapidly delivered high levels of compound 2.7 into the hepatocytes; a concentration of approximately 80 nmoles/g was achieved within 10 minutes. These data indicate that compound 16.4 readily penetrates cells and is efficiently de-esterified to the parent compound, 2.7, intracellularly. Furthermore, as shown in FIG. 11B, compound 16.4 inhibited glucose production in rat hepatocytes.

Example L

Estimation of the Oral Bioavailability of Prodrugs of Phosphonic acids

Prodrugs were dissolved in 10% ethanol/90% polyethylene glycol (mw 400) and administered by oral gavage at doses of approximately 20 or 40 mg/kg parent compound equivalents to 6-hour fasted, Sprague Dawley rats (220-240 g). The rats were subsequently placed in metabolic cages and urine was collected for 24 hours. The quantity of parent compound excreted into urine was determined by HPLC analysis. An ODS column eluted with a gradient from potassium phosphate buffer, pH 5.5 to acetonitrile was employed for these measurements. Detection was at 310-325 nm. The percentage oral bioavailability was estimated by comparison of the recovery in urine of the parent compound generated from the prodrug, to that recovered in urine 24 hours after intravenous administration of unsubstituted parent compound at approximately 10 mg/kg. Parent compounds were typically dissolved in dimethyl sulfoxide, and administered via the tail vein in animals that were briefly anesthetized with halothane.

For compound 16.4, a prodrug of compound 2.7, 6.2% of an oral dose of approximately 20 mg/kg was recovered in urine. For compound 2.7, 76.8% of an intravenous dose of approximately 10 mg/kg was recovered. The oral bioavailability of compound 16.4 was therefore calculated to be 6.2/76.8, or approximately 8%. The oral bioavailability of compound 16.5 was also estimated following the above described protocol to be 5.3%

Example M

Glucose Lowering Following Oral Administration Of FBPase Inhibitors

FBPase inhibitor was administered by oral gavage at doses of 30, 100 and 250 mg/kg to 18-hour fasted, Sprague Dawley rats (250-300 g; n=4-5/group). The compound was prepared in deionized water, adjusted to neutrality with sodium hydroxide, and brought into solution by sonication prior to administration. Blood glucose was measured immediately prior to dosing, and at 1 hour intervals thereafter. Blood samples were obtained from the tail vein; and measurements made by means of a Hemocue glucose analyzer (Hemocue Inc, Mission Viejo, Calif.) used according to the manufacturer's instructions.

We claimed:

1. A method of preventing type II diabetes in animals comprising administering to animals at risk of developing type II diabetes a pharmaceutically effective amount of a compound of formula 1:

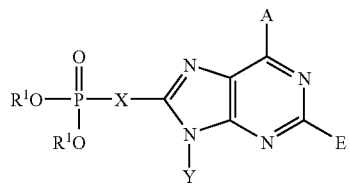

wherein
A is selected from the group consisting of —NR$^8$$_2$, —NHSO$_2$R$^3$, —OR$^5$, —SR$^5$, halo, lower alkyl, —CON(R$^4$)$_2$, guanidino, amidino, —H, and perhaloalkyl;

E is selected from the group consisting of —H, halo, lower alkylthio, lower perhaloalkyl, lower alkyl, lower alkenyl, lower alkynyl, lower alkoxy, —CN, and —NR$^7$$_2$;

X, C, N together with Y form a substituted or unsubstituted heterocyclic group of 4 to about 20 carbon atoms and from 1 to 5 heteroatoms, said heteroatoms being independently selected from N, O, P or S and wherein said substituted heterocyclic group contains from one to four substituents independently selected from lower alkyl, lower aryl, lower aralkyl, lower alicyclic hydroxy, lower alkoxy, lower aryloxy, perhaloalkoxy, aralkoxy, heteroaryl, heteroaryloxy, heteroarylalkyl, heteroaralkoxy, azido, amino, guanidino, halogen, lower alkylthio, —C(O)OR, wherein R is a substituted or unsubstituted alkyl, aryl, aralkyl or alicyclic group, carboxyl, carboxamido, nitro, acyloxy, alkylamino, aminoalkyl, alkylaminoaryl, alkylaryl, alkylaminoalkyl, alkoxyaryl, arylamino, aralkylamino, phosphonate, sulfonate, carboxamidoalkylaryl, carboxamidoaryl, hydroxyalkyl, haloalkyl, alkylaminoalkylcarboxy, aminocarboxamidoalkyl, cyano, lower alkoxyalkyl, and lower perhaloalkyl;

R$^1$ is independently selected from the group consisting of —H, alkyl, aryl, heteroalicyclic where the cyclic moiety contains a carbonate or thiocarbonate, —C(R$^2$)$_2$-aryl, -alk-aryl, —C(R$^2$)$_2$OC(O)NR$^2$$_2$, —NR$^2$—C(O)—R$^3$, —C(R$^2$)$_2$—OC(O)R$^3$, —C(R$^2$)$_2$—O—C(O)OR$^3$, —C(R$_2$)$_2$ OC(O)SR$^3$, -alk-S—C(O)R$^3$, -alk-S—S-alkylhydroxy, and -alk-S—S—S-alkylhydroxy, or together R$^1$ and R$^1$ are -alk-S—S-alk- to form a cyclic group, wherein each "alk" is an independently selected alkylene, or together R$^1$ and R$^1$ are

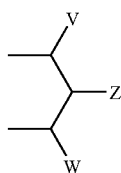

wherein
V and W are independently selected from the group consisting of hydrogen, aryl, substituted aryl, heteroaryl, substituted heteroaryl, 1-alkenyl, 1-alkynyl, and —R$^9$; or together V and Z are connected via a chain of 3-5 atoms, only one of which can be a heteroatom, to form part of a cyclic group substituted with hydroxy, acyloxy, alkoxycarboxy, or aryloxycarboxy attached to a carbon atom that is three atoms from an oxygen attached to the phosphorus; or together V and W are connected via a chain of 3 carbon atoms to form part of a cyclic group substituted with hydroxy, acyloxy, alkoxycarboxy, alkylthiocarboxy, hydroxymethyl, or aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2$$_2$, —CH$_2$Ar, —CH(Ar)OH, —CH(CH=CR$^2$R$^2$)OH, —CH(C≡CR$^2$)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;
R$^3$ is selected from the group consisting of alkyl, aryl, alicyclic, heteroalicyclic, and aralkyl;
R$^4$ is independently selected from the group consisting of —H, lower alkyl, lower alicyclic, lower heteroalicyclic, lower aralkyl, and lower aryl;
R$^5$ is selected from the group consisting of lower alkyl, lower aryl, lower aralkyl, lower alicyclic, and lower heteroalicyclic;
R$^6$ is independently selected from the group consisting of —H, and lower alkyl;
R$^7$ is independently selected from the group consisting of —H, lower alkyl, lower alicyclic, lower heteroalicyclic, lower aralkyl, lower aryl, and —C(O)R$^{10}$;
R$^8$ is independently selected from the group consisting of —H, lower alkyl, lower aralkyl, lower aryl, lower alicyclic, —C(O)R$^{10}$, or together said R$^8$ groups form a bidendate alkylene;

R⁹ is selected from the group consisting of alkyl, aralkyl, alicyclic, and heteroalicyclic;

R¹⁰ is selected from the group consisting of —H, lower alkyl, —NH₂, lower aryl, and lower perhaloalkyl;

R¹¹ is selected from the group consisting of alkyl, aryl, —OH, —NH₂ and —OR³; and pharmaceutically acceptable prodrugs and salts thereof.

2. A method of treating impaired glucose tolerance comprising administering to patients a pharmaceutically effective amount of an FBPase inhibitor of formula 1:

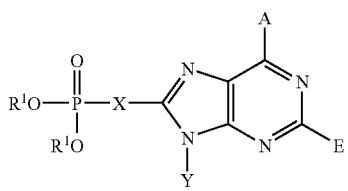

wherein

A is selected from the group consisting of —NR⁸₂, —NHSO₂R³, —OR⁵, —SR⁵, halo, lower alkyl, —CON(R⁴)₂, guanidino, amidino, —H, and perhaloalkyl;

E is selected from the group consisting of —H, halo, lower alkylthio, lower perhaloalkyl, lower alkyl, lower alkenyl, lower alkynyl, lower alkoxy, —CN, and —NR⁷₂;

X, C, N together with Y form a substituted or unsubstituted heterocyclic group of 4 to about 20 carbon atoms and from 1 to 5 heteroatoms, said heteroatoms being independently selected from N, O, P or S and wherein said substituted heterocyclic group contains from one to four substituents independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, halogen, lower alkylthio, —C(O)OR, wherein R is a substituted or unsubstituted aklyl, aryl, aralkyl or alicyclic group, carboxyl, carboxamido, nitro, acyloxy, alkylamino, aminoalkyl, alkylaminoaryl, allylaryl, alkylaminoalkyl, alkoxyaryl, arylamino, aralkylamino, phosphonate, sulfonate, carboxamidoalkylaryl, carboxamidoaryl, hydroxyalkyl, haloalkyl, alkylaminoalkylcarboxy, aminocarboxamidoalkyl, cyano, lower alkoxyalkyl, and lower perhaloalkyl;

R¹ is independently selected from the group consisting of —H, alkyl, aryl, heteroalicyclic where the cyclic moiety contains a carbonate or thiocarbonate, —C(R²)₂-aryl, -alk-aryl, —C(R²)₂OC(O)NR²₂, —NR²—C(O)—R³, —C(R²)₂—OC(O)R³, —C(R²)₂—O—C(O)OR³, —C(R²)₂OC(O)SR³, -alk-S—C(O)R³, -alk-S—S-alkylhydroxy, and -alk-S—S—S-alkylhydroxy, or together R¹ and R¹ are -alk-S—S-alk- to form a cyclic group, wherein each "alk" is an independently selected alkylene, or together R¹ and R¹ are

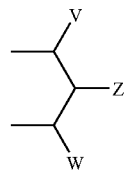

wherein

V and W are independently selected from the group consisting of hydrogen, aryl, substituted aryl, heteroaryl, substituted heteroaryl, 1-alkenyl, 1-alkynyl, and —R⁹; or together V and Z are connected via a chain of 3-5 atoms, only one of which can be a heteroatom, to form part of a cyclic group substituted with hydroxy, acyloxy, alkoxycarboxy, or aryloxycarboxy attached to a carbon atom that is three atoms from an oxygen attached to the phosphorus; or together V and W are connected via a chain of 3 carbon atoms to form part of a cyclic group substituted with hydroxy, acyloxy, alkoxycarboxy, alkylthiocarboxy, hydroxymethyl, or aryloxycarboxy attached to a carbon atom that is three atoms from an oxygen attached to the phosphorus;

Z is selected from the group consisting of —CH₂OH, —CH₂OCOR³, —CH₂OC(O)SR³, —CH₂OCO₂R³, —SR³, —S(O)R³, —CH₂N₃, —CH₂NR²₂, —CH₂Ar, —CH(Ar)OH, —CH(CH=CR²R²)OH, —CH(C≡CR²)OH, and —R²;

with the provisos that:
a) V, Z, W are not all —H; and
b) when Z is —R², then at least one of V and W is not —H or —R⁹;

R² is selected from the group consisting of R³ and —H;

R³ is selected from the group consisting of alkyl, aryl, alicyclic, heteroalicyclic, and aralkyl;

R⁴ is independently selected from the group consisting of —H, lower alkyl, lower alicyclic, lower heteroalicyclic, lower aralkyl, and lower aryl;

R⁵ is selected from the group consisting of lower alkyl, lower aryl, lower aralkyl, lower alicyclic, and lower heteroalicyclic;

R⁶ is independently selected from the group consisting of —H, and lower alkyl;

R⁷ is independently selected from the group consisting of —H, lower alkyl, lower alicyclic, lower heteroalicyclic, lower aralkyl, lower aryl, and —C(O)R¹⁰;

R⁸ is independently selected from the group consisting of —H, lower alkyl, lower aralkyl, lower aryl, lower alicyclic, —C(O)R¹⁰, or together said R⁸ groups form a bidendate alkylene;

R⁹ is selected from the group consisting of alkyl, aralkyl, alicyclic, and heteroalicyclic;

R¹⁰ is selected from the group consisting of —H, lower alkyl, —NH₂, lower aryl, and lower perhaloalkyl;

R¹¹ is selected from the group consisting of alkyl, aryl, —OH, —NH₂ and —OR³; and pharmaceutically acceptable prodrugs and salts thereof.

3. A method of treating insulin resistance comprising administering to patients a pharmaceutically effective amount of an FBPase inhibitor of formula 1:

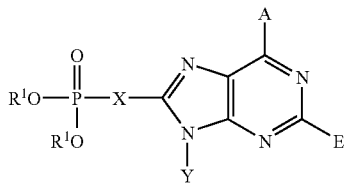

wherein
A is selected from the group consisting of —NR$^8_2$, —NHSO$_2$R$^3$, —OR$^5$, —SR$^5$, halo, lower alkyl, —CON(R$^4$)$_2$, guanidino, amidino, —H, and perhaloalkyl;

E is selected from the group consisting of —H, halo, lower alkylthio, lower perhaloalkyl, lower alkyl, lower alkenyl, lower alkynyl, lower alkoxy, —CN, and —NR$^7_2$;

X, C, N together with Y form a substituted or unsubstituted heterocyclic group of 4 to about 20 carbon atoms and from 1 to 5 heteroatoms, said heteroatoms being independently selected from N, O, P or S and wherein said substituted heterocyclic group contains from one to four substituents independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, halogen, lower alkylthio, —C(O)OR, wherein R is a substituted or unsubstituted aklyl, aryl, aralkyl or alicyclic group, carboxyl, carboxamido, nitro, acyloxy, alkylamino, aminoalkyl, alkylaminoaryl, allylaryl, alkylaminoalkyl, alkoxyaryl, arylamino, aralkylamino, phosphonate, sulfonate, carboxamidoalkylaryl, carboxamidoaryl, hydroxyalkyl, haloalkyl, alkylaminoalkylcarboxy, aminocarboxamidoalkyl, cyano, lower alkoxyalkyl, and lower perhaloalkyl;

R$^1$ is independently selected from the group consisting of —H, alkyl, aryl, heteroalicyclic where the cyclic moiety contains a carbonate or thiocarbonate, —C(R$^2$)$_2$-aryl, -alk-aryl, —C(R$^2$)$_2$OC(O)NR$^2_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alk-S—C(O)R$^3$, -alk-S—S-alkylhydroxy, and -alk-S—S—S-alkylhydroxy, or together R$^1$ and R$^1$ are -alk-S—S-alk- to form a cyclic group, wherein each "alk" is an independently selected alkylene, or together R$^1$ and R$^1$ are

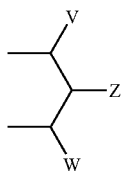

wherein
V and W are independently selected from the group consisting of hydrogen, aryl, substituted aryl, heteroaryl, substituted heteroaryl, 1-alkenyl, 1-alkynyl, and —R$^9$; or
together V and Z are connected via a chain of 3-5 atoms, only one of which can be a heteroatom, to form part of a cyclic group substituted with hydroxy, acyloxy, alkoxycarboxy, or aryloxycarboxy attached to a carbon atom that is three atoms from an oxygen attached to the phosphorus; or
together V and W are connected via a chain of 3 carbon atoms to form part of a cyclic group substituted with hydroxy, acyloxy, alkoxycarboxy, alkylthiocarboxy, hydroxymethyl, or aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2_2$, —CH$_2$Ar, —CH(Ar)OH, —CH(CH═CR$^2$ R$^2$)OH, —CH(C≡CR$^2$)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;

R$^3$ is selected from the group consisting of alkyl, aryl, alicyclic, heteroalicyclic, and aralkyl;

R$^4$ is independently selected from the group consisting of —H, lower alkyl, lower alicyclic, lower heteroalicyclic, lower aralkyl, and lower aryl;

R$^5$ is selected from the group consisting of lower alkyl, lower aryl, lower aralkyl, lower alicyclic, and lower heteroalicyclic;

R$^6$ is independently selected from the group consisting of —H, and lower alkyl;

R$^7$ is independently selected from the group consisting of —H, lower alkyl lower alicyclic, lower heteroalicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together said R$^8$ groups form a bidendate alkylene;

R$^9$ is selected from the group consisting of alkyl, aralkyl, alicyclic, and heteroalicyclic;

R$^{10}$ is selected from the group consisting of —H, lower alkyl, —NH$_2$, lower aryl, and lower perhaloalkyl;

R$^{11}$ is selected from the group consisting of alkyl, aryl, —OH, —NH$_2$ and —OR$^3$; and pharmaceutically acceptable prodrugs and salts thereof.

4. The method of claim 1 wherein said animals at risk of developing diabetes have a disease or condition selected from the group consisting of impaired glucose tolerance, insulin resistance, hyperglycemia, obesity, accelerated gluconeogenesis, and increased hepatic glucose output.

5. A method of treating or preventing a disease or condition associated with increased insulin levels selected from the group consisting of hyperlipidemia, atherosclerosis, ischemic injury, and hypercholesterolemia which comprises administering to an animal in need thereof a pharmaceutically effective amount of an FBPase inhibitor of formula 1:

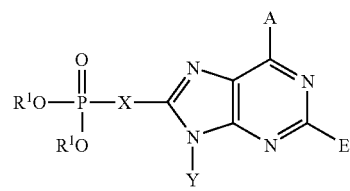

wherein

A is selected from the group consisting of —NR$^8_2$, —NHSO$_2$R$^3$, —OR$^5$, —SR$^5$, halo, lower alkyl, —CON(R$^4$)$_2$, guanidino, amidino, —H, and perhaloalkyl;

E is selected from the group consisting of —H, halo, lower alkylthio, lower perhaloalkyl, lower alkyl, lower alkenyl, lower alkynyl, lower alkoxy, —CN, and —NR$^7_2$;

X, C, N together with Y form a substituted or unsubstituted heterocyclic group of 4 to about 20 carbon atoms and from 1 to 5 heteroatoms, said heteroatoms being independently selected from N, O, P or S and wherein said substituted heterocyclic group contains from one to four substituents independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, halogen, lower alkylthio, —C(O)OR, wherein R is a substituted or unsubstituted aklyl, aryl, aralkyl or alicyclic group, carboxyl, carboxamido, nitro, acyloxy, alkylamino, aminoalkyl, alkylaminoaryl, allylaryl, alkylaminoalkyl, alkoxyaryl, arylamino, aralkylamino, phosphonate, sulfonate, carboxamidoalkylaryl, carboxamidoaryl, hydroxyalkyl, haloalkyl, alkylaminoalkylcarboxy, aminocarboxamidoalkyl, cyano, lower alkoxyalkyl, and lower perhaloalkyl;

R$^1$ is independently selected from the group consisting of —H, alkyl, aryl, heteroalicyclic where the cyclic moiety contains a carbonate or thiocarbonate, —C(R$^2$)$_2$-aryl, -alk-aryl, —C(R$^2$)$_2$OC(O)NR$^2_2$, —NR$^2$—C(O)—R$^3$, —C(R$^2$)$_2$—OC(O)R$^3$, —C(R$^2$)$_2$—O—C(O)OR$^3$, —C(R$_2$)$_2$ OC(O)SR$^3$, -alk-S—C(O)R$^3$, -alk-S—S-alkylhydroxy, and -alk-S—S-alkylhydroxy, or together R$^1$ and R$^1$ are -alk-S—S-alk- to form a cyclic group, wherein each "alk" is an independently selected alkylene, or together R$^1$ and R$^1$ are

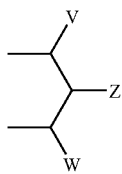

wherein

V and W are independently selected from the group consisting of hydrogen, aryl, substituted aryl, heteroaryl, substituted heteroaryl, 1-alkenyl, 1-alkynyl, and —R$^9$; or together V and Z are connected via a chain of 3-5 atoms, only one of which can be a heteroatom, to form part of a cyclic group substituted with hydroxy, acyloxy, alkoxycarboxy, or aryloxycarboxy attached to a carbon atom that is three atoms from an oxygen attached to the phosphorus; or together V and W are connected via a chain of 3 carbon atoms to form part of a cyclic group substituted with hydroxy, acyloxy, alkoxycarboxy, alkylthiocarboxy, hydroxymethyl, or aryloxycarboxy attached to a carbon atom that is three atoms from an oxygen attached to the phosphorus;

Z is selected from the group consisting of —CH$_2$OH, —CH$_2$OCOR$^3$, —CH$_2$OC(O)SR$^3$, —CH$_2$OCO$_2$R$^3$, —SR$^3$, —S(O)R$^3$, —CH$_2$N$_3$, —CH$_2$NR$^2_2$, —CH$_2$Ar, —CH(Ar)OH, —CH(CH═CR$^2$ R$^2$)OH, —CH(C≡CR$^2$)OH, and —R$^2$;

with the provisos that:
a) V, Z, W are not all —H; and
b) when Z is —R$^2$, then at least one of V and W is not —H or —R$^9$;

R$^2$ is selected from the group consisting of R$^3$ and —H;

R$^3$ is selected from the group consisting of alkyl, aryl, alicyclic, heteroalicyclic, and aralkyl;

R$^4$ is independently selected from the group consisting of —H, lower alkyl, lower alicyclic, lower heteroalicyclic, lower aralkyl, and lower aryl;

R$^5$ is selected from the group consisting of lower alkyl, lower aryl, lower aralkyl, lower alicyclic, and lower heteroalicyclic;

R$^6$ is independently selected from the group consisting of —H, and lower alkyl;

R$^7$ is independently selected from the group consisting of —H, lower alkyl, lower alicyclic, lower heteroalicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together said R$^8$ groups form a bidendate alkylene;

R$^9$ is selected from the group consisting of alkyl, aralkyl, alicyclic, and heteroalicyclic;

R$^{10}$ is selected from the group consisting of —H, lower alkyl, —NH$_2$, lower aryl, and lower perhaloalkyl;

R$^{11}$ is selected from the group consisting of alkyl, aryl, —OH, —NH$_2$ and —OR$^3$; and pharmaceutically acceptable prodrugs and salts thereof.

6. A pharmaceutical composition comprising a pharmaceutically effective amount of an FBPase inhibitor of formula 1:

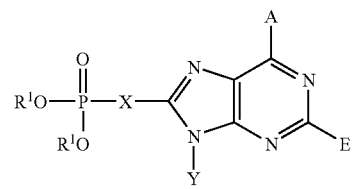

wherein

A is selected from the group consisting of —NR$^8_2$, —NHSO$_2$R$^3$, —OR$^5$, —SR$^5$, halo, lower alkyl, —CON(R$^4$)$_2$, guanidino, amidino, —H, and perhaloalkyl;

E is selected from the group consisting of —H, halo, lower alkylthio, lower perhaloalkyl, lower alkyl, lower alkenyl, lower alkynyl, lower alkoxy, —CN, and —NR$^7_2$;

X, C, N together with Y form a substituted or unsubstituted heterocyclic group of 4 to about 20 carbon atoms and from 1 to 5 heteroatoms, said heteroatoms being independently selected from N, O, P or S and wherein said substituted heterocyclic group contains from one to four substituents independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, halogen, lower alkylthio, —C(O)OR, wherein R is a substituted or unsubstituted aklyl, aryl, aralkyl or alicyclic group, carboxyl, carboxamido, nitro, acyloxy, alkylamino, aminoalkyl, alkylaminoaryl, allylaryl, alkylaminoalkyl, alkoxyaryl, arylamino, aralkylamino, phosphonate, sulfonate, carboxamidoalkylaryl, carboxamidoaryl, hydroxyalkyl, haloalkyl, alkylaminoalkylcarboxy, aminocarboxamidoalkyl, cyano, lower alkoxyalkyl, and lower perhaloalkyl;

$R^1$ is independently selected from the group consisting of —H, alkyl, aryl, heteroalicyclic where the cyclic moiety contains a carbonate or thiocarbonate, —C($R^2$)$_2$-aryl, -alk-aryl, —C($R^2$)$_2$OC(O)N$R^2_2$, —N$R^2$—C(O)—$R^3$, —C($R^2$)$_2$—OC(O)$R^3$, —C($R^2$)$_2$—O—C(O)O$R^3$, —C($R^2$)$_2$ OC(O)S$R^3$, -alk-S—C(O)$R^3$, -alk-S—S-alkylhydroxy, and -alk-S—S—S-alkylhydroxy, or together $R^1$ and $R^1$ are -alk-S—S-alk- to form a cyclic group, wherein each "alk" is an independently selected alkylene, or together $R^1$ and $R^1$ are

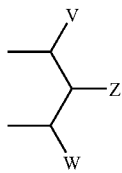

wherein

V and W are independently selected from the group consisting of hydrogen, aryl, substituted aryl, heteroaryl, substituted heteroaryl, 1-alkenyl, 1-alkynyl, and —$R^9$; or together V and Z are connected via a chain of 3-5 atoms, only one of which can be a heteroatom, to form part of a cyclic group substituted with hydroxy, acyloxy, alkoxycarboxy, or aryloxycarboxy attached to a carbon atom that is three atoms from an oxygen attached to the phosphorus; or together V and W are connected via a chain of 3 carbon atoms to form part of a cyclic group substituted with hydroxy, acyloxy, alkoxycarboxy, alkylthiocarboxy, hydroxymethyl, or aryloxycarboxy attached to a carbon atom that is three atoms from an oxygen attached to the phosphorus;

Z is selected from the group consisting of —CH$_2$OH, —CH$_2$OCO$R^3$, —CH$_2$OC(O)S$R^3$, —CH$_2$OCO$_2R^3$, —S$R^3$, —S(O)$R^3$, —CH$_2$N$_3$, —CH$_2$NR$^2_2$, —CH$_2$Ar, —CH(Ar)OH, —CH(CH=C$R^2R^2$)OH, —CH(C≡C$R^2$)OH, and —$R^2$;

with the provisos that:
a) V, Z, W are not all —H; and
b) when Z is —$R^2$, then at least one of V and W is not —H or —$R^9$;

$R^2$ is selected from the group consisting of $R^3$ and —H;

$R^3$ is selected from the group consisting of alkyl, aryl, alicyclic, heteroalicyclic, and aralkyl;

$R^4$ is independently selected from the group consisting of —H, lower alkyl, lower alicyclic, lower heteroalicyclic, lower aralkyl, and lower aryl;

$R^5$ is selected from the group consisting of lower alkyl, lower aryl, lower aralkyl, lower alicyclic, and lower heteroalicyclic;

$R^6$ is independently selected from the group consisting of —H, and lower alkyl;

$R^7$ is independently selected from the group consisting of —H, lower alkyl, lower alicyclic, lower heteroalicyclic, lower aralkyl, lower aryl, and —C(O)$R^{10}$;

$R^8$ is independently selected from the group consisting of —H, lower alkyl, lower aralkyl, lower aryl, lower alicyclic, —C(O)$R^{10}$, or together said $R^8$ groups form a bidendate alkylene;

$R^9$ is selected from the group consisting of alkyl, aralkyl, alicyclic, and heteroalicyclic;

$R^{10}$ is selected from the group consisting of —H, lower alkyl, —NH$_2$, lower aryl, and lower perhaloalkyl;

$R^{11}$ is selected from the group consisting of alkyl, aryl, —OH, —NH$_2$ and —O$R^3$; and pharmaceutically acceptable prodrugs and salts thereof; and a pharmaceutically acceptable carrier.

* * * * *

UNITED STATES PATENT AND TRADEMARK OFFICE
CERTIFICATE OF CORRECTION

PATENT NO. : 7,285,543 B2
APPLICATION NO. : 11/101807
DATED : October 23, 2007
INVENTOR(S) : Qun Dang et al.

It is certified that error appears in the above-identified patent and that said Letters Patent is hereby corrected as shown below:

Column 4,
Line 15, "$^4$C-bicarbonate" should read -- $^{14}$C-bicarbonate --.

Columns 25-26,
Table Compound No. 206, "2-cyclohexylerhyl" should read --2-cyclohexylethyl--.

Column 65,
Lines 57-58, "lower alicyclic hydroxy," should read --lower alicyclic, hydroxy,--.

Column 66,
Line 8, "—C($R_2$)$_2$" should read -- —C($R^2$)$_2$ --.

Column 67,
Line 6, "—$NH_2$and" should read -- —$NH_2$ and--.
Line 46, "unsubstituted aklyl" should read --unsubstituted alkyl--.
Line 49, "allylaryl" should read --alkylaryl--.

Column 68,
Line 63, "—$NH_2$and" should read -- —$NH_2$ and--.

Column 69,
Line 34, "allylaryl" should read --alkylaryl--.

Column 70,
Line 32, "lower alkyl lower" should read --lower alkyl, lower--.

Column 71,
Line 21, "aklyl" should read --alkyl--.
Line 23, "allylaryl" should read --alkylaryl--.
Line 34, "—C($R_2$)$_2$" should read -- —C($R^2$)$_2$ --.

Column 72,
Line 31, "—$NH_2$and" should read -- —$NH_2$ and--.
Line 67, "aklyl" should read --alkyl--.

UNITED STATES PATENT AND TRADEMARK OFFICE
CERTIFICATE OF CORRECTION

PATENT NO.        : 7,285,543 B2
APPLICATION NO.   : 11/101807
DATED             : October 23, 2007
INVENTOR(S)       : Qun Dang et al.

It is certified that error appears in the above-identified patent and that said Letters Patent is hereby corrected as shown below:

Column 73,
Line 2, "allylaryl" should read --alkylaryl--.
Line 13, "—C(R$_2$)$_2$" should read -- —C(R$^2$)$_2$--.

Column 74,
Line 13, "R$^2$is" should read --R$^2$ is--.
Line 37, "—NH$_2$and" should read -- —NH$_2$ and--.

Signed and Sealed this

Seventeenth Day of June, 2008

JON W. DUDAS
*Director of the United States Patent and Trademark Office*